United States Patent
Bernick et al.

(10) Patent No.: US 10,675,288 B2
(45) Date of Patent: Jun. 9, 2020

(54) NATURAL COMBINATION HORMONE REPLACEMENT FORMULATIONS AND THERAPIES

(71) Applicant: TherapeuticsMD, Inc., Boca Raton, FL (US)

(72) Inventors: Brian A. Bernick, Boca Raton, FL (US); Janice Louise Cacace, Miami, FL (US); Peter H. R. Persicaner, Boca Raton, FL (US); Neda Irani, Palm Beach Gardens, FL (US); Julia M. Amadio, Boca Raton, FL (US)

(73) Assignee: TherapeuticsMD, Inc., Boca Raton, FL (US)

( * ) Notice: Subject to any disclaimer, the term of this patent is extended or adjusted under 35 U.S.C. 154(b) by 0 days.

(21) Appl. No.: 15/090,493

(22) Filed: Apr. 4, 2016

(65) Prior Publication Data

US 2016/0213685 A1  Jul. 28, 2016

Related U.S. Application Data

(63) Continuation of application No. 13/843,428, filed on Mar. 15, 2013, now Pat. No. 9,301,920, which is a continuation-in-part of application No. 13/684,002, filed on Nov. 21, 2012, now Pat. No. 8,633,178.

(60) Provisional application No. 61/662,265, filed on Jun. 20, 2012, provisional application No. 61/661,302, filed on Jun. 18, 2012, provisional application No. 61/563,408, filed on Nov. 23, 2011.

(51) Int. Cl.
| | |
|---|---|
| *A61K 31/57* | (2006.01) |
| *A61K 31/565* | (2006.01) |
| *A61K 47/44* | (2017.01) |
| *A61K 47/10* | (2017.01) |
| *A61K 47/14* | (2017.01) |
| *A61K 9/107* | (2006.01) |
| *A61K 9/48* | (2006.01) |
| *A61K 9/00* | (2006.01) |
| *A61K 9/02* | (2006.01) |

(52) U.S. Cl.
CPC ............ *A61K 31/57* (2013.01); *A61K 9/0034* (2013.01); *A61K 9/02* (2013.01); *A61K 9/1075* (2013.01); *A61K 9/48* (2013.01); *A61K 9/4858* (2013.01); *A61K 9/4866* (2013.01); *A61K 31/565* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| | | |
|---|---|---|
| 1,967,351 A | 1/1934 | Doisy |
| 2,232,438 A | 2/1941 | Butenandt |
| 2,379,832 A | 7/1945 | Serini et al. |
| 2,649,399 A | 8/1953 | Beall et al. |
| 3,198,707 A | 8/1965 | Nomine et al. |
| 3,478,070 A | 11/1969 | Stein et al. |
| 3,526,648 A | 9/1970 | Bertin et al. |
| 3,710,795 A | 1/1973 | Higuchi et al. |
| 3,729,560 A | 4/1973 | Hagerman |
| 3,729,566 A | 4/1973 | Ericsson et al. |
| 3,755,573 A | 8/1973 | Berman |
| 3,755,575 A | 8/1973 | Lerner |
| 3,903,880 A | 9/1975 | Higuchi et al. |
| 3,916,898 A | 11/1975 | Robinson |
| 3,916,899 A | 11/1975 | Theeuwes et al. |
| 3,921,636 A | 11/1975 | Zaffaroni |
| 3,923,997 A | 12/1975 | Meuly |
| 3,948,254 A | 4/1976 | Zaffaroni |
| 3,971,367 A | 6/1976 | Zaffaroni |
| 3,977,404 A | 8/1976 | Theeuwes |
| 3,993,072 A | 11/1976 | Zaffaroni |
| 4,008,719 A | 2/1977 | Theeuwes et al. |
| 4,012,496 A | 3/1977 | Schopflin et al. |
| 4,014,334 A | 3/1977 | Theeuwes et al. |
| 4,014,987 A | 3/1977 | Heller et al. |
| 4,016,251 A | 8/1977 | Higuchi et al. |
| 4,071,623 A | 1/1978 | van der Vies |
| 4,093,709 A | 6/1978 | Choi et al. |
| 4,154,820 A | 5/1979 | Simoons |
| 4,155,991 A | 5/1979 | Schopflin et al. |
| 4,196,188 A | 4/1980 | Besins |

(Continued)

FOREIGN PATENT DOCUMENTS

| | | |
|---|---|---|
| BR | PI1001367-9 A2 | 7/2012 |
| CA | 2044371 A1 | 12/1991 |

(Continued)

OTHER PUBLICATIONS

US 6,214,374 B1, 04/2001, Schmirler et al. (withdrawn)

(Continued)

*Primary Examiner* — Dennis J Parad

(74) *Attorney, Agent, or Firm* — Kilpatrick Townsend & Stockton LLP

(57) ABSTRACT

Estrogen and progesterone replacement therapies are provided herein. Among others, the following formulations are provided herein: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone.

16 Claims, 5 Drawing Sheets

(56) References Cited

U.S. PATENT DOCUMENTS

| | | |
|---|---|---|
| 4,215,691 A | 8/1980 | Wong |
| 4,237,885 A | 12/1980 | Wong et al. |
| 4,310,510 A | 1/1982 | Sherman et al. |
| 4,327,725 A | 5/1982 | Cortese et al. |
| 4,372,951 A | 2/1983 | Vorys |
| 4,384,096 A | 5/1983 | Sonnabend |
| 4,393,871 A | 7/1983 | Vorhauer et al. |
| 4,402,695 A | 9/1983 | Wong |
| 4,423,151 A | 12/1983 | Baranczuk |
| 4,449,980 A | 5/1984 | Millar et al. |
| 4,610,687 A | 9/1986 | Fogwell |
| 4,629,449 A | 12/1986 | Wong |
| 4,732,763 A | 3/1988 | Beck et al. |
| 4,738,957 A | 4/1988 | Laurent et al. |
| 4,756,907 A | 7/1988 | Beck et al. |
| 4,762,717 A | 8/1988 | Crowley, Jr. |
| 4,788,062 A | 11/1988 | Gale et al. |
| 4,816,257 A | 3/1989 | Buster et al. |
| 4,822,616 A | 4/1989 | Zimmermann et al. |
| 4,865,848 A | 9/1989 | Cheng et al. |
| 4,900,734 A * | 2/1990 | Maxson ............... A61K 9/4858 514/171 |
| 4,906,475 A | 3/1990 | Kim |
| 4,942,158 A | 7/1990 | Sarpotdar et al. |
| 4,961,931 A | 10/1990 | Wong |
| 5,030,629 A | 7/1991 | Rajadhyaksha |
| 5,043,331 A | 8/1991 | Hirvonen et al. |
| 5,059,426 A | 10/1991 | Chiang |
| 5,064,654 A | 11/1991 | Berner et al. |
| 5,108,995 A | 4/1992 | Casper |
| 5,128,138 A | 7/1992 | Blank |
| 5,130,137 A | 7/1992 | Crowley, Jr. |
| 5,140,021 A | 8/1992 | Maxson et al. |
| 5,164,416 A | 11/1992 | Nagai et al. |
| 5,208,225 A | 5/1993 | Boissonneault et al. |
| 5,211,952 A | 5/1993 | Spicer et al. |
| 5,252,334 A | 10/1993 | Chiang et al. |
| 5,280,023 A | 1/1994 | Ehrlich et al. |
| 5,288,496 A | 2/1994 | Lewis |
| 5,340,584 A | 8/1994 | Spicer et al. |
| 5,340,585 A | 8/1994 | Pike et al. |
| 5,340,586 A | 8/1994 | Pike et al. |
| 5,362,497 A | 8/1994 | Yamada et al. |
| 5,382,573 A | 1/1995 | Casper |
| 5,393,528 A | 2/1995 | Staab |
| 5,393,529 A | 2/1995 | Hoffmann et al. |
| 5,419,910 A | 5/1995 | Lewis |
| 5,453,279 A | 9/1995 | Lee et al. |
| 5,468,736 A | 11/1995 | Hodgen |
| 5,474,783 A | 12/1995 | Miranda et al. |
| 5,480,776 A | 1/1996 | Dullien |
| 5,514,673 A | 5/1996 | Heckenmueller et al. |
| 5,516,528 A | 5/1996 | Hughes et al. |
| 5,527,534 A | 6/1996 | Myhling |
| 5,529,782 A | 6/1996 | Staab |
| 5,538,736 A | 7/1996 | Barth et al. |
| 5,543,150 A | 8/1996 | Bologna et al. |
| 5,547,948 A | 8/1996 | Barcomb |
| 5,556,635 A | 9/1996 | Grognet et al. |
| 5,565,199 A | 10/1996 | Page et al. |
| 5,567,831 A | 10/1996 | Li |
| 5,569,652 A | 10/1996 | Beier et al. |
| 5,580,572 A | 12/1996 | Liorzou et al. |
| 5,582,592 A | 12/1996 | Kendrick |
| 5,585,370 A | 12/1996 | Casper |
| 5,595,759 A | 1/1997 | Wright et al. |
| 5,595,970 A | 1/1997 | Garfield et al. |
| 5,605,702 A | 2/1997 | Math et al. |
| 5,607,691 A | 3/1997 | Solas et al. |
| 5,607,693 A | 3/1997 | Bonte et al. |
| 5,609,617 A | 3/1997 | Cady et al. |
| 5,620,705 A | 4/1997 | Dong et al. |
| 5,626,866 A | 5/1997 | Heiber et al. |
| 5,629,021 A | 5/1997 | Wright |
| 5,633,011 A | 5/1997 | Dong et al. |
| 5,633,242 A | 5/1997 | Oettel et al. |
| 5,639,743 A | 6/1997 | Kaswan et al. |
| 5,645,856 A | 6/1997 | Lacy et al. |
| 5,653,983 A | 8/1997 | Bonte et al. |
| 5,656,286 A | 8/1997 | Miranda et al. |
| 5,660,839 A | 8/1997 | Allec et al. |
| 5,662,927 A | 9/1997 | Ehrlich et al. |
| 5,663,160 A | 9/1997 | Dumas et al. |
| 5,676,968 A | 10/1997 | Lipp et al. |
| 5,677,292 A | 10/1997 | Li et al. |
| 5,686,097 A | 11/1997 | Crisologo et al. |
| 5,693,335 A | 12/1997 | Xia et al. |
| 5,694,947 A | 12/1997 | Lehtinen et al. |
| 5,700,480 A | 12/1997 | Hille et al. |
| 5,709,844 A | 1/1998 | Arbeit et al. |
| 5,719,197 A | 2/1998 | Mantelle et al. |
| 5,735,801 A | 4/1998 | Caillouette |
| 5,739,176 A | 4/1998 | Dunn et al. |
| 5,744,463 A | 4/1998 | Bair |
| 5,747,058 A | 5/1998 | Tipton et al. |
| 5,762,614 A | 6/1998 | Caillouette |
| 5,770,176 A | 6/1998 | Nargessi |
| 5,770,219 A | 6/1998 | Chiang et al. |
| 5,770,220 A | 6/1998 | Meconi et al. |
| 5,770,227 A | 6/1998 | Dong et al. |
| 5,776,495 A | 7/1998 | Duclos et al. |
| 5,780,044 A | 7/1998 | Tipton et al. |
| 5,780,050 A | 7/1998 | Jain et al. |
| 5,788,980 A | 8/1998 | Nabahi |
| 5,788,984 A | 8/1998 | Schmidt et al. |
| 5,789,442 A | 8/1998 | Garfield et al. |
| 5,811,416 A | 9/1998 | Chwalisz et al. |
| 5,811,547 A | 9/1998 | Nakamichi et al. |
| 5,814,329 A | 9/1998 | Shah |
| 5,820,878 A | 10/1998 | Shinmura et al. |
| 5,827,200 A | 10/1998 | Caillouette |
| 5,840,327 A | 11/1998 | Gale et al. |
| 5,843,468 A | 12/1998 | Yum et al. |
| 5,843,979 A | 12/1998 | Wille et al. |
| 5,858,394 A | 1/1999 | Lipp et al. |
| 5,863,552 A | 1/1999 | Yue |
| 5,866,603 A | 2/1999 | Li et al. |
| 5,869,084 A | 2/1999 | Paradissis et al. |
| 5,882,676 A | 3/1999 | Yum et al. |
| 5,885,612 A | 3/1999 | Meconi et al. |
| 5,888,533 A | 3/1999 | Dunn |
| 5,891,462 A | 4/1999 | Carrara |
| 5,891,868 A | 4/1999 | Cummings et al. |
| 5,898,038 A | 4/1999 | Yallampalli et al. |
| 5,902,603 A | 5/1999 | Chen et al. |
| 5,904,931 A | 5/1999 | Gunther et al. |
| 5,906,830 A | 5/1999 | Farinas et al. |
| 5,912,010 A | 6/1999 | Wille et al. |
| 5,916,176 A | 6/1999 | Caillouette |
| RE36,247 E | 7/1999 | Plunkett et al. |
| 5,919,477 A | 7/1999 | Bevan et al. |
| 5,922,349 A | 7/1999 | Elliesen et al. |
| 5,928,666 A | 7/1999 | Farinas et al. |
| 5,942,243 A | 8/1999 | Shah |
| 5,942,531 A | 8/1999 | Diaz et al. |
| 5,952,000 A | 9/1999 | Fikstad et al. |
| 5,958,446 A | 9/1999 | Miranda et al. |
| 5,962,445 A | 10/1999 | Stewart |
| 5,968,919 A | 10/1999 | Gyurik et al. |
| 5,972,372 A | 10/1999 | Saleh et al. |
| 5,985,311 A | 11/1999 | Cordes et al. |
| 5,985,850 A | 11/1999 | Falk et al. |
| 5,985,861 A | 11/1999 | Levine et al. |
| 5,993,856 A | 11/1999 | Ragavan et al. |
| 5,989,568 A | 12/1999 | de Lacharriere et al. |
| 6,001,846 A | 12/1999 | Edwards et al. |
| 6,007,835 A | 12/1999 | Bon Lapillonne et al. |
| 6,010,715 A | 1/2000 | Pollock et al. |
| 6,013,276 A | 1/2000 | Teillaud et al. |
| 6,022,562 A | 2/2000 | Autant et al. |
| 6,024,974 A | 2/2000 | Li |
| 6,024,976 A | 2/2000 | Miranda et al. |
| 6,028,057 A | 2/2000 | Burns |
| 6,030,948 A | 2/2000 | Mann et al. |

(56) References Cited

U.S. PATENT DOCUMENTS

| | | |
|---|---|---|
| 6,039,968 A | 3/2000 | Nabahi |
| 6,040,340 A | 3/2000 | Garfield et al. |
| 6,056,972 A | 5/2000 | Hermsmeyer |
| 6,060,077 A | 5/2000 | Meignant |
| 6,068,853 A | 5/2000 | Berner et al. |
| 6,074,625 A | 6/2000 | Hawthorne et al. |
| 6,077,531 A | 6/2000 | Salin-Drouin |
| 6,080,118 A | 6/2000 | Blythe |
| 6,083,178 A | 7/2000 | Caillouette |
| 6,086,916 A | 7/2000 | Agnus et al. |
| 6,087,352 A | 7/2000 | Trout |
| 6,090,404 A | 7/2000 | Meconi et al. |
| 6,096,338 A | 7/2000 | Lacy et al. |
| 6,106,848 A | 8/2000 | Willcox et al. |
| 6,117,446 A | 9/2000 | Place |
| 6,117,450 A | 9/2000 | Dittgen et al. |
| 6,124,362 A | 9/2000 | Bradbury et al. |
| 6,133,251 A | 10/2000 | Dittgen et al. |
| 6,133,320 A | 10/2000 | Yallampalli et al. |
| 6,139,868 A | 10/2000 | Hoffmann |
| 6,139,873 A | 10/2000 | Hughes, Jr. et al. |
| 6,149,935 A | 11/2000 | Tenzel et al. |
| 6,153,216 A | 11/2000 | Cordes et al. |
| 6,165,491 A | 12/2000 | Grasset et al. |
| 6,165,975 A | 12/2000 | Adams et al. |
| 6,187,323 B1 | 2/2001 | Aiache et al. |
| 6,187,339 B1 | 2/2001 | de Haan et al. |
| 6,190,331 B1 | 2/2001 | Caillouette |
| 6,201,072 B1 | 3/2001 | Rathi et al. |
| 6,217,886 B1 | 4/2001 | Rubinstein et al. |
| 6,225,297 B1 | 5/2001 | Stockemann et al. |
| 6,227,202 B1 | 5/2001 | Matapurkar |
| 6,228,383 B1 | 5/2001 | Hansen et al. |
| 6,228,852 B1 | 5/2001 | Shaak |
| 6,242,509 B1 | 6/2001 | Macqueen et al. |
| 6,245,811 B1 | 6/2001 | Horrobin et al. |
| 6,262,115 B1 | 7/2001 | Guittard et al. |
| 6,267,984 B1 | 7/2001 | Hamlin et al. |
| 6,274,165 B1 | 8/2001 | Meconi et al. |
| 6,277,418 B1 | 8/2001 | Marakverich et al. |
| 6,283,927 B1 | 9/2001 | Caillouette |
| 6,284,263 B1 | 9/2001 | Place |
| 6,287,588 B1 | 9/2001 | Shih et al. |
| 6,287,693 B1 | 9/2001 | Savoir et al. |
| 6,294,188 B1 | 9/2001 | Ragavan et al. |
| 6,294,192 B1 | 9/2001 | Patel et al. |
| 6,294,550 B1 | 9/2001 | Place et al. |
| 6,299,900 B1 | 10/2001 | Reed et al. |
| 6,303,132 B1 | 10/2001 | Nelson |
| 6,303,588 B1 | 10/2001 | Danielov |
| 6,306,841 B1 | 10/2001 | Place et al. |
| 6,306,914 B1 | 10/2001 | de Ziegler et al. |
| 6,309,669 B1 | 10/2001 | Setterstrom et al. |
| 6,309,848 B1 | 10/2001 | Howett et al. |
| 6,312,703 B1 | 11/2001 | Orthoefer et al. |
| 6,328,987 B1 | 12/2001 | Marini |
| 6,342,491 B1 | 1/2002 | Dey et al. |
| 6,344,211 B1 | 2/2002 | Hille |
| 6,372,209 B1 | 4/2002 | Chrisope |
| 6,372,245 B1 | 4/2002 | Vo et al. |
| 6,372,246 B1 | 4/2002 | Wei et al. |
| 6,387,390 B1 | 5/2002 | Deaver et al. |
| 6,402,705 B1 | 6/2002 | Caillouette |
| 6,416,778 B1 | 7/2002 | Ragavan et al. |
| 6,420,352 B1 | 7/2002 | Knowles |
| 6,423,039 B1 | 7/2002 | Rathbone et al. |
| 6,423,683 B1 | 7/2002 | Heaton et al. |
| 6,432,438 B1 | 8/2002 | Shukla |
| 6,436,633 B1 | 8/2002 | Kreider et al. |
| 6,440,454 B1 | 8/2002 | Santoro et al. |
| 6,444,224 B1 | 9/2002 | Rathbone et al. |
| 6,444,234 B1 | 9/2002 | Kirby et al. |
| 6,451,300 B1 | 9/2002 | Leyba et al. |
| 6,451,339 B2 | 9/2002 | Patel et al. |
| 6,451,779 B1 | 9/2002 | Hesch |
| 6,455,246 B1 | 9/2002 | Howett et al. |
| 6,455,517 B1 | 9/2002 | Tanabe et al. |
| 6,465,004 B1 | 10/2002 | Houze et al. |
| 6,465,005 B1 | 10/2002 | Biali et al. |
| 6,465,006 B1 | 10/2002 | Zhang et al. |
| 6,468,526 B2 | 10/2002 | Chrisope |
| 6,469,016 B1 | 10/2002 | Place et al. |
| 6,472,434 B1 | 10/2002 | Place et al. |
| 6,479,232 B1 | 11/2002 | Howett et al. |
| 6,495,160 B2 | 12/2002 | Esposito et al. |
| 6,500,814 B1 | 12/2002 | Hesch |
| 6,503,896 B1 | 1/2003 | Tanabe et al. |
| 6,511,969 B1 | 1/2003 | Hermsmeyer |
| 6,521,250 B2 | 2/2003 | Seibertz et al. |
| 6,526,980 B1 | 3/2003 | Tracy et al. |
| 6,528,094 B1 | 3/2003 | Savoir et al. |
| 6,531,149 B1 | 3/2003 | Meconi et al. |
| 6,537,580 B1 | 3/2003 | Savoir et al. |
| 6,538,039 B2 | 3/2003 | Laurent |
| 6,544,196 B2 | 4/2003 | Caillouette |
| 6,544,553 B1 | 4/2003 | Hsia et al. |
| 6,548,053 B1 | 4/2003 | Murray et al. |
| 6,548,491 B2 | 4/2003 | Tanabe et al. |
| 6,551,611 B2 | 4/2003 | Elliesen et al. |
| 6,555,131 B1 | 4/2003 | Wolff et al. |
| 6,562,367 B1 | 5/2003 | Wolff et al. |
| 6,562,370 B2 | 5/2003 | Luo et al. |
| 6,562,790 B2 | 5/2003 | Chein |
| 6,569,463 B2 | 5/2003 | Patel et al. |
| 6,583,129 B1 | 6/2003 | Mazer et al. |
| 6,586,006 B2 | 7/2003 | Roser et al. |
| 6,589,549 B2 | 7/2003 | Shih et al. |
| 6,593,317 B1 | 7/2003 | de Ziegler et al. |
| 6,599,519 B1 | 7/2003 | Seo et al. |
| 6,610,325 B1 | 8/2003 | Meignant |
| 6,610,652 B2 | 8/2003 | Adams et al. |
| 6,610,670 B2 | 8/2003 | Bickensfeld et al. |
| 6,610,674 B1 | 8/2003 | Schreiber |
| 6,635,274 B1 | 10/2003 | Carter et al. |
| 6,638,528 B1 | 10/2003 | Kanios |
| 6,638,536 B2 | 10/2003 | Savoir et al. |
| 6,645,528 B1 | 11/2003 | Straub et al. |
| 6,649,155 B1 | 11/2003 | Dunlop et al. |
| 6,653,298 B1 | 11/2003 | Potter et al. |
| 6,656,929 B1 | 12/2003 | Agnus et al. |
| 6,660,726 B2 | 12/2003 | Hill et al. |
| 6,663,608 B2 | 12/2003 | Rathbone et al. |
| 6,663,895 B2 | 12/2003 | Savoir et al. |
| 6,664,296 B1 | 12/2003 | Meignant |
| 6,682,757 B1 | 1/2004 | Wright |
| 6,692,763 B1 | 2/2004 | Cummings et al. |
| 6,708,822 B1 | 3/2004 | Muni |
| 6,716,454 B2 | 4/2004 | Meignant |
| 6,720,001 B2 | 4/2004 | Chen et al. |
| 6,737,081 B2 | 5/2004 | Savoir et al. |
| 6,740,333 B2 | 5/2004 | Beckett et al. |
| 6,743,448 B2 | 6/2004 | Kryger |
| 6,743,815 B2 | 6/2004 | Huebner et al. |
| 6,747,018 B2 | 6/2004 | Tanabe et al. |
| 6,750,291 B2 | 6/2004 | Kim et al. |
| 6,756,208 B2 | 6/2004 | Griffin et al. |
| 6,776,164 B2 | 8/2004 | Bunt et al. |
| 6,787,152 B2 | 9/2004 | Kirby et al. |
| 6,787,531 B1 | 9/2004 | Hilman et al. |
| 6,805,877 B2 | 10/2004 | Massara et al. |
| 6,809,085 B1 | 10/2004 | Elson et al. |
| 6,818,226 B2 | 11/2004 | Reed et al. |
| 6,821,524 B2 | 11/2004 | Marini |
| 6,841,716 B1 | 1/2005 | Tsutsumi |
| 6,844,334 B2 | 1/2005 | Hill et al. |
| 6,855,703 B1 | 2/2005 | Hill et al. |
| 6,860,859 B2 | 3/2005 | Mehrotra et al. |
| 6,866,865 B2 | 3/2005 | Hsia et al. |
| 6,869,969 B2 | 3/2005 | Heubner et al. |
| 6,878,518 B2 | 4/2005 | Whitehead |
| 6,901,278 B1 | 5/2005 | Notelovitz |
| 6,905,705 B2 | 6/2005 | Palm et al. |
| 6,911,211 B2 | 6/2005 | Tamarkin et al. |
| 6,911,438 B2 | 6/2005 | Wright |

(56) References Cited

U.S. PATENT DOCUMENTS

| | | |
|---|---|---|
| 6,923,988 B2 | 8/2005 | Patel et al. |
| 6,924,274 B2 | 8/2005 | Lardy et al. |
| 6,932,983 B1 | 8/2005 | Straub et al. |
| 6,939,558 B2 | 9/2005 | Massara et al. |
| 6,943,021 B2 | 9/2005 | Klausner et al. |
| 6,958,327 B1 | 10/2005 | Hillisch et al. |
| 6,960,337 B2 | 11/2005 | Pike et al. |
| 6,962,691 B1 | 11/2005 | Lulla et al. |
| 6,962,908 B2 | 11/2005 | Aloba et al. |
| 6,967,194 B1 | 11/2005 | Matsuo et al. |
| 6,974,569 B2 | 12/2005 | Boyd et al. |
| 6,977,250 B2 | 12/2005 | Rodriguez |
| 6,978,945 B2 | 12/2005 | Wong et al. |
| 6,987,129 B2 | 1/2006 | Mak et al. |
| 6,995,149 B1 | 2/2006 | Reilhac et al. |
| 7,004,321 B1 | 2/2006 | Hackbarth et al. |
| 7,005,429 B2 | 2/2006 | Dey et al. |
| 7,011,846 B2 | 3/2006 | Shojaei et al. |
| 7,018,992 B2 | 3/2006 | Koch et al. |
| 7,030,104 B2 | 4/2006 | Paris et al. |
| 7,030,157 B2 | 4/2006 | Ke et al. |
| RE39,104 E | 5/2006 | Duclos et al. |
| 7,074,779 B2 | 7/2006 | Sui et al. |
| 7,083,590 B1 | 8/2006 | Bunt et al. |
| 7,091,213 B2 | 8/2006 | Metcalf, III et al. |
| 7,094,228 B2 | 8/2006 | Zhang et al. |
| 7,097,853 B1 | 8/2006 | Keister et al. |
| 7,101,342 B1 | 9/2006 | Caillouette |
| 7,105,573 B2 | 9/2006 | Krajcik et al. |
| 7,135,190 B2 | 11/2006 | Piao et al. |
| 7,153,522 B1 | 12/2006 | Ikeura et al. |
| 7,163,681 B2 | 1/2007 | Giles-Komar et al. |
| 7,163,699 B2 | 1/2007 | Besse |
| 7,175,850 B2 | 2/2007 | Cevc |
| 7,179,799 B2 | 2/2007 | Hill et al. |
| 7,196,074 B2 | 3/2007 | Blye et al. |
| 7,198,800 B1 | 4/2007 | Ko |
| 7,198,801 B2 | 4/2007 | Carrara et al. |
| 7,226,910 B2 | 6/2007 | Wilson et al. |
| 7,247,625 B2 | 7/2007 | Zhang et al. |
| 7,250,446 B2 | 7/2007 | Sangita et al. |
| 7,267,829 B2 | 9/2007 | Kirby et al. |
| 7,300,926 B2 | 11/2007 | Prokai et al. |
| 7,303,763 B2 | 12/2007 | Ho |
| 7,317,037 B2 | 1/2008 | Fensome et al. |
| 7,329,654 B2 | 2/2008 | Kanojia et al. |
| 7,335,650 B2 | 2/2008 | Potter et al. |
| 7,374,779 B2 | 5/2008 | Chen et al. |
| 7,378,404 B2 | 5/2008 | Peters et al. |
| 7,381,427 B2 | 6/2008 | Ancira et al. |
| 7,387,789 B2 | 6/2008 | Klose et al. |
| 7,388,006 B2 | 6/2008 | Schmees et al. |
| 7,414,043 B2 | 8/2008 | Kosemund et al. |
| 7,427,413 B2 | 9/2008 | Savoir et al. |
| 7,427,609 B2 | 9/2008 | Leonard |
| 7,429,576 B2 | 9/2008 | Labrie |
| 7,431,941 B2 | 10/2008 | Besins et al. |
| 7,456,159 B2 | 11/2008 | Houze et al. |
| 7,459,445 B2 | 12/2008 | Hill et al. |
| 7,465,587 B2 | 12/2008 | Imrich |
| 7,470,433 B2 | 12/2008 | Carrara et al. |
| 7,485,666 B2 | 2/2009 | Villaneuva et al. |
| 7,497,855 B2 | 3/2009 | Ausiello et al. |
| 7,498,303 B2 | 3/2009 | Arnold et al. |
| 7,534,765 B2 | 5/2009 | Gregg et al. |
| 7,534,780 B2 | 5/2009 | Ring et al. |
| 7,550,142 B2 | 6/2009 | Giles-Komar et al. |
| 7,563,565 B1 | 7/2009 | Matsuo et al. |
| 7,569,274 B2 | 8/2009 | Alphonse et al. |
| 7,572,779 B2 | 8/2009 | Aloba et al. |
| 7,572,780 B2 | 8/2009 | Hermsmeyer |
| 7,589,082 B2 | 9/2009 | Savoir et al. |
| 7,671,027 B2 | 3/2010 | Loumaye |
| 7,674,783 B2 | 3/2010 | Hermsmeyer |
| 7,687,281 B2 | 3/2010 | Roth et al. |
| 7,687,485 B2 | 3/2010 | Levinson et al. |
| 7,694,683 B2 | 4/2010 | Callister et al. |
| 7,704,983 B1 | 4/2010 | Hodgen et al. |
| 7,727,720 B2 | 6/2010 | Dhallan |
| 7,732,408 B2 | 6/2010 | Josephson et al. |
| 7,749,989 B2 | 7/2010 | Hill et al. |
| 7,767,656 B2 | 8/2010 | Shoichet et al. |
| 7,799,769 B2 | 9/2010 | White et al. |
| 7,815,936 B2 | 10/2010 | Hasenzahl et al. |
| 7,815,949 B2 | 10/2010 | Cohen |
| 7,829,115 B2 | 11/2010 | Besins et al. |
| 7,829,116 B2 | 11/2010 | Frye et al. |
| RE42,012 E | 12/2010 | Deaver et al. |
| 7,850,992 B2 | 12/2010 | Hwang et al. |
| 7,854,753 B2 | 12/2010 | Kraft et al. |
| 7,858,607 B2 | 12/2010 | Mamchur |
| RE42,072 E | 1/2011 | Deaver et al. |
| 7,862,552 B2 | 1/2011 | McIntyre et al. |
| 7,867,990 B2 | 1/2011 | Schultz et al. |
| 7,871,643 B2 | 1/2011 | Lizio et al. |
| 7,879,830 B2 | 2/2011 | Wiley |
| 7,884,093 B2 | 2/2011 | Creasy et al. |
| 7,925,519 B2 | 4/2011 | Greene |
| 7,939,104 B2 | 5/2011 | Barbera et al. |
| 7,943,602 B2 | 5/2011 | Bunschoten et al. |
| 7,943,604 B2 | 5/2011 | Coelingh Bennink et al. |
| 7,945,459 B2 | 5/2011 | Grace et al. |
| 7,960,368 B2 | 6/2011 | Rao et al. |
| 7,989,436 B2 | 8/2011 | Hill et al. |
| 7,989,487 B2 | 8/2011 | Welsh et al. |
| 8,022,053 B2 | 9/2011 | Mueller et al. |
| 8,048,017 B2 | 11/2011 | Xu |
| 8,048,869 B2 | 11/2011 | Bunschoten et al. |
| 8,063,030 B2 | 11/2011 | Ellman |
| 8,071,576 B2 | 12/2011 | Visser et al. |
| 8,071,729 B2 | 12/2011 | Giles-Komar et al. |
| 8,075,916 B2 | 12/2011 | Park et al. |
| 8,075,917 B2 | 12/2011 | Park et al. |
| 8,076,317 B2 | 12/2011 | Kulmann |
| 8,076,319 B2 | 12/2011 | Leonard |
| 8,080,553 B2 | 12/2011 | Auspitz et al. |
| 8,088,605 B2 | 1/2012 | Beudet et al. |
| 8,096,940 B2 | 1/2012 | Iverson et al. |
| 8,101,209 B2 | 1/2012 | Legrand et al. |
| 8,101,773 B2 | 1/2012 | Smith et al. |
| 8,114,152 B2 | 2/2012 | Furst |
| 8,114,434 B2 | 2/2012 | Sasaki et al. |
| 8,114,442 B2 | 2/2012 | Tucker et al. |
| 8,119,741 B2 | 2/2012 | Pavlin |
| 8,121,886 B2 | 2/2012 | Azar |
| 8,124,118 B2 | 2/2012 | Lennernaes et al. |
| 8,124,595 B2 | 2/2012 | Boissonneault |
| 8,147,561 B2 | 4/2012 | Binmoeller |
| 8,148,546 B2 | 4/2012 | Baasner et al. |
| 8,158,613 B2 | 4/2012 | Staniforth et al. |
| 8,158,614 B2 | 4/2012 | Lambert et al. |
| 8,163,722 B2 | 4/2012 | Savoir et al. |
| 8,177,449 B2 | 5/2012 | Watkinson et al. |
| 8,182,833 B2 | 5/2012 | Hermsmeyer |
| 8,187,615 B2 | 5/2012 | Friedman |
| 8,187,640 B2 | 5/2012 | Dunn |
| 8,195,403 B2 | 6/2012 | Wood, Jr. et al. |
| 8,202,736 B2 | 6/2012 | Mousa et al. |
| 8,217,024 B2 | 7/2012 | Ahmed et al. |
| 8,221,785 B2 | 7/2012 | Chien |
| 8,222,008 B2 | 7/2012 | Thoene |
| 8,222,237 B2 | 7/2012 | Narkunan et al. |
| 8,227,454 B2 | 7/2012 | Hill et al. |
| 8,227,509 B2 | 7/2012 | Castro et al. |
| 8,241,664 B2 | 8/2012 | Dudley et al. |
| 8,247,393 B2 | 8/2012 | Ahmed et al. |
| 8,257,724 B2 | 9/2012 | Cromack et al. |
| 8,257,725 B2 | 9/2012 | Cromack et al. |
| 8,268,352 B2 | 9/2012 | Karan et al. |
| 8,268,806 B2 | 9/2012 | Labrie |
| 8,268,878 B2 | 9/2012 | Johnson et al. |
| 8,273,730 B2 | 9/2012 | Fernandez et al. |
| 8,287,888 B2 | 10/2012 | Song et al. |
| 8,288,366 B2 | 10/2012 | Gonzalez et al. |

(56) References Cited

U.S. PATENT DOCUMENTS

| | | |
|---|---|---|
| 8,318,898 B2 | 11/2012 | Fasel et al. |
| 8,324,193 B2 | 12/2012 | Lee et al. |
| 8,329,680 B2 | 12/2012 | Evans et al. |
| 8,337,814 B2 | 12/2012 | Osbakken et al. |
| 8,344,007 B2 | 1/2013 | Chui et al. |
| 8,349,820 B2 | 1/2013 | Zeun et al. |
| 8,353,863 B2 | 1/2013 | Imran |
| 8,357,723 B2 | 1/2013 | Satyam |
| 8,361,995 B2 | 1/2013 | Schramm |
| 8,362,091 B2 | 1/2013 | Besonov et al. |
| 8,372,424 B2 | 2/2013 | Berry et al. |
| 8,372,806 B2 | 2/2013 | Bragagna et al. |
| 8,377,482 B2 | 2/2013 | Laurie et al. |
| 8,377,994 B2 | 2/2013 | Drechsler et al. |
| 8,394,759 B2 | 3/2013 | Barathur et al. |
| 8,415,332 B2 | 4/2013 | Reape et al. |
| 8,420,111 B2 | 4/2013 | Hermsmeyer |
| 8,435,561 B2 | 5/2013 | Besins et al. |
| 8,435,972 B2 | 5/2013 | Sayeed et al. |
| 8,449,879 B2 | 5/2013 | Laurent et al. |
| 8,450,108 B2 | 5/2013 | Boyce |
| 8,454,945 B2 | 6/2013 | Narain et al. |
| 8,455,468 B2 | 6/2013 | Kellermann et al. |
| 8,461,138 B2 | 6/2013 | Boissonneault |
| 8,476,252 B2 | 7/2013 | Pickersgill et al. |
| 8,481,488 B2 | 7/2013 | Carter |
| 8,486,374 B2 | 7/2013 | Zlatkis et al. |
| 8,486,442 B2 | 7/2013 | Yamaji et al. |
| 8,492,368 B2 | 7/2013 | Lewandowski et al. |
| 8,507,467 B2 | 8/2013 | Ueda et al. |
| 8,512,693 B2 | 8/2013 | Azevedo et al. |
| 8,512,754 B2 | 8/2013 | Needham |
| 8,518,376 B2 | 8/2013 | Schuz et al. |
| 8,536,159 B2 | 9/2013 | Zeng et al. |
| 8,540,967 B2 | 9/2013 | Trivedi et al. |
| 8,541,400 B2 | 9/2013 | Joabsson et al. |
| 8,551,462 B2 | 10/2013 | Marenus et al. |
| 8,551,508 B2 | 10/2013 | Lee et al. |
| 8,557,281 B2 | 10/2013 | Tuominen et al. |
| 8,568,374 B2 | 10/2013 | de Graaff et al. |
| 8,591,951 B2 | 11/2013 | Kohn et al. |
| 8,613,951 B2 | 12/2013 | Troiano et al. |
| 8,633,178 B2 * | 1/2014 | Bernick .................. A61K 9/16 424/452 |
| 8,633,180 B2 | 1/2014 | Zeng et al. |
| 8,636,787 B2 | 1/2014 | Sabaria |
| 8,636,982 B2 | 1/2014 | Schuz et al. |
| 8,653,129 B2 | 2/2014 | Fein et al. |
| 8,658,627 B2 | 2/2014 | Voskuhl |
| 8,658,628 B2 | 2/2014 | Baucom |
| 8,663,681 B2 | 3/2014 | Ahmed et al. |
| 8,663,692 B1 | 3/2014 | Mueller et al. |
| 8,663,703 B2 | 3/2014 | Moldavski et al. |
| 8,664,207 B2 | 3/2014 | Zheng et al. |
| 8,669,293 B2 | 3/2014 | Sharoni et al. |
| 8,679,552 B2 | 3/2014 | Guthery |
| 8,694,358 B2 | 4/2014 | Tryfon |
| 8,697,127 B2 | 4/2014 | Sah |
| 8,697,710 B2 | 4/2014 | Zeng et al. |
| 8,703,105 B2 | 4/2014 | Besonov et al. |
| 8,709,385 B2 | 4/2014 | Schuz et al. |
| 8,709,451 B2 | 4/2014 | Rapoport et al. |
| 8,715,735 B2 | 5/2014 | Funke et al. |
| 8,721,331 B2 | 5/2014 | Raghuprasad |
| 8,722,021 B2 | 5/2014 | Eini et al. |
| 8,734,846 B2 | 5/2014 | Hrkach et al. |
| 8,735,381 B2 | 5/2014 | Podolski |
| 8,741,336 B2 | 6/2014 | Dipierro et al. |
| 8,741,373 B2 | 6/2014 | Rao et al. |
| 8,753,661 B2 | 6/2014 | Gassner et al. |
| 8,784,882 B2 | 7/2014 | Mattern |
| 8,846,648 B2 * | 9/2014 | Bernick .................. A61K 9/16 424/452 |
| 8,846,649 B2 * | 9/2014 | Bernick .................. A61K 9/16 424/452 |
| 8,933,059 B2 * | 1/2015 | Bernick .................. A61K 31/57 424/452 |
| 8,987,237 B2 * | 3/2015 | Bernick .................. A61K 9/16 424/452 |
| 8,987,238 B2 * | 3/2015 | Bernick .................. A61K 31/57 424/452 |
| 8,993,548 B2 * | 3/2015 | Bernick .................. A61K 9/16 424/452 |
| 8,993,549 B2 * | 3/2015 | Bernick .................. A61K 9/16 424/452 |
| 9,006,222 B2 * | 4/2015 | Bernick .................. A61K 31/57 424/452 |
| 9,012,434 B2 * | 4/2015 | Bernick .................. A61K 31/57 424/452 |
| 9,114,145 B2 * | 8/2015 | Bernick .................. A61K 9/16 |
| 9,114,146 B2 * | 8/2015 | Bernick .................. A61K 9/16 |
| 9,180,091 B2 | 11/2015 | Bernick et al. |
| 9,248,136 B2 * | 2/2016 | Bernick .................. A61K 9/16 |
| 9,289,382 B2 | 3/2016 | Bernick et al. |
| 9,301,920 B2 * | 4/2016 | Bernick .................. A61K 31/57 |
| 9,931,349 B2 | 4/2018 | Shadiack et al. |
| 10,052,386 B2 | 8/2018 | Bernick et al. |
| 10,258,630 B2 | 4/2019 | Mirkin et al. |
| 2001/0005728 A1 | 2/2001 | Guittard et al. |
| 2001/0009673 A1 | 7/2001 | Gunther et al. |
| 2001/0021816 A1 | 9/2001 | Caillouette |
| 2001/0023261 A1 | 9/2001 | Ryoo et al. |
| 2001/0027189 A1 | 10/2001 | Bennink et al. |
| 2001/0029357 A1 | 10/2001 | Bunt et al. |
| 2001/0031747 A1 | 10/2001 | de Ziegler et al. |
| 2001/0032125 A1 | 10/2001 | Bhan et al. |
| 2001/0034340 A1 | 10/2001 | Pickar |
| 2012/0269878 A2 | 10/2001 | Cantor et al. |
| 2001/0053383 A1 | 12/2001 | Sablotsky et al. |
| 2001/0056068 A1 | 12/2001 | Chwalisz et al. |
| 2002/0012710 A1 | 1/2002 | Lansky |
| 2002/0026158 A1 | 2/2002 | Rathbone et al. |
| 2002/0028788 A1 | 3/2002 | Bunt et al. |
| 2002/0035070 A1 | 3/2002 | Gardlik et al. |
| 2002/0058648 A1 | 5/2002 | Hammerly |
| 2002/0058926 A1 | 5/2002 | Rathbone et al. |
| 2002/0064541 A1 | 5/2002 | Lapidot et al. |
| 2002/0076441 A1 | 6/2002 | Shih et al. |
| 2002/0102308 A1 | 8/2002 | Wei et al. |
| 2002/0107230 A1 | 8/2002 | Waldon et al. |
| 2002/0114803 A1 | 8/2002 | Deaver et al. |
| 2002/0119174 A1 | 8/2002 | Gardlik et al. |
| 2002/0119198 A1 | 8/2002 | Gao et al. |
| 2002/0132801 A1 | 9/2002 | Heil et al. |
| 2002/0137749 A1 | 9/2002 | Levinson et al. |
| 2002/0142017 A1 | 10/2002 | Simonnet |
| 2002/0151530 A1 | 10/2002 | Leonard et al. |
| 2002/0156394 A1 | 10/2002 | Mehrotra et al. |
| 2002/0169150 A1 | 11/2002 | Pickar |
| 2002/0169205 A1 | 11/2002 | Garfield et al. |
| 2002/0173510 A1 | 11/2002 | Levinson et al. |
| 2002/0193356 A1 | 12/2002 | Van Beek et al. |
| 2002/0193758 A1 | 12/2002 | Sandberg |
| 2002/0197286 A1 | 12/2002 | Brandman et al. |
| 2003/0003139 A1 | 1/2003 | Gunther et al. |
| 2003/0004145 A1 | 1/2003 | Leonard |
| 2003/0007994 A1 | 1/2003 | Bunt et al. |
| 2003/0027772 A1 | 2/2003 | Breton |
| 2003/0091620 A1 | 2/2003 | Venkateshwaran et al. |
| 2003/0044453 A1 | 3/2003 | Volkel et al. |
| 2003/0049307 A1 | 3/2003 | Gyurik |
| 2003/0064097 A1 | 4/2003 | Patel et al. |
| 2003/0064975 A1 | 4/2003 | Koch et al. |
| 2003/0072760 A1 | 4/2003 | Sirbasku |
| 2003/0073248 A1 | 4/2003 | Roth et al. |
| 2003/0073673 A1 | 4/2003 | Hesch |
| 2003/0077297 A1 | 4/2003 | Chen et al. |
| 2003/0078245 A1 | 4/2003 | Bennink et al. |
| 2003/0091640 A1 | 5/2003 | Ramanathan et al. |
| 2003/0092691 A1 | 5/2003 | Besse et al. |
| 2003/0096012 A1 | 5/2003 | Besse et al. |
| 2003/0104048 A1 | 6/2003 | Patel et al. |
| 2003/0109507 A1 | 6/2003 | Beckmann et al. |
| 2003/0113268 A1 | 6/2003 | Buenafae et al. |

(56) References Cited

U.S. PATENT DOCUMENTS

| | | |
|---|---|---|
| 2003/0114420 A1 | 6/2003 | Salvati et al. |
| 2003/0114430 A1 | 6/2003 | MacLeod et al. |
| 2003/0124182 A1 | 7/2003 | Shojaei et al. |
| 2003/0124191 A1 | 7/2003 | Besse et al. |
| 2003/0130558 A1 | 7/2003 | Massara et al. |
| 2003/0144258 A1 | 7/2003 | Heil et al. |
| 2003/0157157 A1 | 8/2003 | Luo et al. |
| 2003/0166509 A1 | 9/2003 | Edwards et al. |
| 2003/0170295 A1 | 9/2003 | Yoon et al. |
| 2003/0175329 A1 | 9/2003 | Mak et al. |
| 2003/0175333 A1 | 9/2003 | Shefer et al. |
| 2003/0180352 A1 | 9/2003 | Patel et al. |
| 2003/0181353 A1 | 9/2003 | Nyce |
| 2003/0181728 A1 | 9/2003 | Salvati et al. |
| 2003/0191096 A1 | 10/2003 | Leonard et al. |
| 2003/0195177 A1 | 10/2003 | Leonard et al. |
| 2003/0215496 A1 | 11/2003 | Patel et al. |
| 2003/0219402 A1 | 11/2003 | Rutter |
| 2003/0220297 A1 | 11/2003 | Berstein et al. |
| 2003/0224057 A1 | 12/2003 | Martin-Letellier et al. |
| 2003/0224059 A1 | 12/2003 | Lerner et al. |
| 2003/0225047 A1 | 12/2003 | Friedman et al. |
| 2003/0225048 A1 | 12/2003 | Friedman et al. |
| 2003/0225050 A1 | 12/2003 | Eichardt et al. |
| 2003/0228686 A1 | 12/2003 | Klausner et al. |
| 2003/0229057 A1 | 12/2003 | Caubel et al. |
| 2003/0235596 A1 | 12/2003 | Gao et al. |
| 2003/0236236 A1* | 12/2003 | Chen .................. A61B 17/0483 514/171 |
| 2004/0009960 A1 | 1/2004 | Heil et al. |
| 2004/0022820 A1 | 2/2004 | Anderson |
| 2004/0034001 A1 | 2/2004 | Karara |
| 2004/0037881 A1 | 2/2004 | Guittard et al. |
| 2004/0039356 A1 | 2/2004 | Maki et al. |
| 2004/0043043 A1 | 3/2004 | Schlyter et al. |
| 2004/0043943 A1 | 3/2004 | Guittard et al. |
| 2004/0044080 A1 | 3/2004 | Place et al. |
| 2004/0048900 A1 | 3/2004 | Flood |
| 2004/0052824 A1 | 3/2004 | Abou Chacra-Vernet et al. |
| 2004/0073024 A1 | 4/2004 | Metcalf, III et al. |
| 2004/0077605 A1 | 4/2004 | Salvati et al. |
| 2004/0077606 A1 | 4/2004 | Salvati et al. |
| 2004/0087548 A1 | 5/2004 | Salvati et al. |
| 2004/0087564 A1 | 5/2004 | Wright et al. |
| 2004/0089308 A1 | 5/2004 | Welch |
| 2004/0092494 A9 | 5/2004 | Dudley |
| 2004/0092583 A1 | 5/2004 | Shanahan-Prendergast |
| 2004/0093261 A1 | 5/2004 | Jain et al. |
| 2004/0097468 A1 | 5/2004 | Wimalawansa |
| 2004/0101557 A1 | 5/2004 | Gibson et al. |
| 2004/0106542 A1 | 6/2004 | Deaver et al. |
| 2004/0110732 A1 | 6/2004 | Masini et al. |
| 2004/0131670 A1 | 7/2004 | Gao |
| 2004/0138103 A1 | 7/2004 | Patt |
| 2004/0142012 A1 | 7/2004 | Bunt et al. |
| 2004/0146539 A1 | 7/2004 | Gupta |
| 2004/0146894 A1 | 7/2004 | Warrington et al. |
| 2004/0147578 A1 | 7/2004 | Calvet |
| 2004/0161435 A1 | 8/2004 | Gupta |
| 2004/0176324 A1 | 9/2004 | Salvati et al. |
| 2004/0176336 A1 | 9/2004 | Rodriguez |
| 2004/0185104 A1 | 9/2004 | Piao et al. |
| 2004/0191207 A1 | 9/2004 | Lipari et al. |
| 2004/0191276 A1 | 9/2004 | Muni |
| 2004/0198706 A1 | 10/2004 | Carrara et al. |
| 2004/0210280 A1 | 10/2004 | Liedtke |
| 2004/0213744 A1 | 10/2004 | Lulla et al. |
| 2004/0219124 A1 | 11/2004 | Gupta |
| 2004/0225140 A1 | 11/2004 | Sciano et al. |
| 2004/0234606 A1 | 11/2004 | Levine et al. |
| 2004/0241219 A1 | 12/2004 | Hille et al. |
| 2004/0243437 A1 | 12/2004 | Grace et al. |
| 2004/0253319 A1 | 12/2004 | Netke et al. |
| 2004/0259817 A1 | 12/2004 | Waldon et al. |
| 2004/0266745 A1 | 12/2004 | Schwanitz et al. |
| 2005/0003003 A1 | 1/2005 | Basu et al. |
| 2005/0004088 A1 | 1/2005 | Hesch |
| 2005/0009800 A1 | 1/2005 | Thumbeck et al. |
| 2005/0014729 A1 | 1/2005 | Pulaski |
| 2005/0020550 A1 | 1/2005 | Latif et al. |
| 2005/0020552 A1 | 1/2005 | Aschkenasay et al. |
| 2005/0021009 A1 | 1/2005 | Massara et al. |
| 2005/0025833 A1 | 2/2005 | Aschkenasay et al. |
| 2005/0031651 A1 | 2/2005 | Gervais et al. |
| 2005/0042173 A1 | 2/2005 | Besse et al. |
| 2005/0042268 A1 | 2/2005 | Aschkenasay et al. |
| 2005/0048116 A1 | 3/2005 | Straub et al. |
| 2005/0054991 A1 | 3/2005 | Paterson et al. |
| 2005/0079138 A1 | 4/2005 | Chickering, III et al. |
| 2005/0085453 A1 | 4/2005 | Govindarajan |
| 2005/0101579 A1 | 5/2005 | Shippen |
| 2005/0113350 A1 | 5/2005 | Duesterberg et al. |
| 2005/0118244 A1 | 6/2005 | Theobild et al. |
| 2005/0118272 A1 | 6/2005 | Besse et al. |
| 2005/0129756 A1 | 6/2005 | Podhaisky et al. |
| 2005/0152956 A1 | 7/2005 | Dudley |
| 2005/0153946 A1 | 7/2005 | Hirsh et al. |
| 2005/0164977 A1 | 7/2005 | Coelingh Bennink |
| 2005/0182105 A1 | 8/2005 | Nirschl et al. |
| 2005/0186141 A1 | 8/2005 | Gonda et al. |
| 2005/0187267 A1 | 8/2005 | Hamann et al. |
| 2005/0192253 A1 | 9/2005 | Salvati et al. |
| 2005/0192310 A1 | 9/2005 | Gavai et al. |
| 2005/0196434 A1 | 9/2005 | Brierre |
| 2005/0207990 A1 | 9/2005 | Funke et al. |
| 2005/0209209 A1 | 9/2005 | Koch et al. |
| 2005/0214384 A1 | 9/2005 | Juturu et al. |
| 2005/0220825 A1 | 10/2005 | Funke et al. |
| 2005/0220900 A1 | 10/2005 | Wuttke et al. |
| 2005/0222106 A1 | 10/2005 | Bracht |
| 2005/0228692 A1 | 10/2005 | Hodgdon |
| 2005/0228718 A1 | 10/2005 | Austin |
| 2005/0239747 A1 | 10/2005 | Le et al. |
| 2005/0239758 A1 | 10/2005 | Roby |
| 2005/0244360 A1 | 11/2005 | Billoni |
| 2005/0244522 A1 | 11/2005 | Carrara et al. |
| 2005/0245902 A1 | 11/2005 | Cornish et al. |
| 2005/0250746 A1 | 11/2005 | Iammatteo |
| 2005/0250750 A1 | 11/2005 | Cummings et al. |
| 2005/0250753 A1 | 11/2005 | Fink et al. |
| 2005/0256028 A1 | 11/2005 | Yun et al. |
| 2005/0266078 A1 | 11/2005 | Jorda et al. |
| 2005/0266088 A1 | 12/2005 | Frijlink et al. |
| 2005/0271597 A1 | 12/2005 | Keith |
| 2005/0271598 A1 | 12/2005 | Friedman et al. |
| 2005/0272685 A1 | 12/2005 | Hung |
| 2005/0272712 A1 | 12/2005 | Grubb et al. |
| 2006/0009428 A1 | 1/2006 | Grubb et al. |
| 2006/0014728 A1 | 1/2006 | Chwalisz et al. |
| 2006/0018937 A1 | 1/2006 | Friedman et al. |
| 2006/0019978 A1 | 1/2006 | Balog |
| 2006/0020002 A1 | 1/2006 | Salvati et al. |
| 2006/0030615 A1 | 2/2006 | Fensome et al. |
| 2006/0034889 A1 | 2/2006 | Jo et al. |
| 2006/0034904 A1 | 2/2006 | Weimann |
| 2006/0040904 A1 | 2/2006 | Ahmed et al. |
| 2006/0051391 A1 | 3/2006 | Dvoskin et al. |
| 2006/0052341 A1 | 3/2006 | Cornish et al. |
| 2006/0069031 A1 | 3/2006 | Loumaye |
| 2006/0078618 A1 | 4/2006 | Constantinides et al. |
| 2006/0083778 A1 | 4/2006 | Allison et al. |
| 2006/0084704 A1 | 4/2006 | Shih et al. |
| 2006/0088580 A1 | 4/2006 | Seibertz et al. |
| 2006/0089337 A1 | 4/2006 | Casper et al. |
| 2006/0093678 A1 | 5/2006 | Chickering, III et al. |
| 2006/0100180 A1 | 5/2006 | Bohlmann et al. |
| 2006/0106004 A1 | 5/2006 | Brody et al. |
| 2006/0110415 A1 | 5/2006 | Gupta |
| 2006/0111424 A1 | 5/2006 | Salvati et al. |
| 2006/0121102 A1 | 6/2006 | Chiang |
| 2006/0121626 A1 | 6/2006 | Imrich |
| 2006/0134188 A1 | 6/2006 | Podhaisky et al. |
| 2006/0135619 A1 | 6/2006 | Kick et al. |
| 2006/0165744 A1 | 7/2006 | Anyarambhatla et al. |

(56) References Cited

U.S. PATENT DOCUMENTS

| | | |
|---|---|---|
| 2006/0193789 A1 | 8/2006 | Tamarkin et al. |
| 2006/0194775 A1 | 8/2006 | Tofovic et al. |
| 2006/0204557 A1 | 9/2006 | Gupta et al. |
| 2006/0233743 A1 | 10/2006 | Kelly |
| 2006/0233841 A1 | 10/2006 | Pushpala et al. |
| 2006/0235037 A1 | 10/2006 | Purandare et al. |
| 2006/0240111 A1 | 10/2006 | Fernandez et al. |
| 2006/0246122 A1 | 11/2006 | Langguth et al. |
| 2006/0247216 A1 | 11/2006 | Haj-Yehia |
| 2006/0247221 A1 | 11/2006 | Coelingh et al. |
| 2006/0251581 A1 | 11/2006 | Madenjian et al. |
| 2006/0252049 A1 | 11/2006 | Shuler et al. |
| 2006/0257472 A1 | 11/2006 | Neilsen |
| 2006/0275218 A1 | 12/2006 | Besonov et al. |
| 2006/0275360 A1 | 12/2006 | Ahmed et al. |
| 2006/0276414 A1 | 12/2006 | Coelingh et al. |
| 2006/0280771 A1 | 12/2006 | Groenewegen et al. |
| 2006/0280797 A1 | 12/2006 | Shoichet et al. |
| 2006/0280800 A1 | 12/2006 | Nagi et al. |
| 2006/0292223 A1 | 12/2006 | Mc Ilroy et al. |
| 2007/0004693 A1 | 1/2007 | Woolfson et al. |
| 2007/0004694 A1 | 1/2007 | Woolfson et al. |
| 2007/0009559 A1 | 1/2007 | Alosio et al. |
| 2007/0009594 A1 | 1/2007 | Grubb et al. |
| 2007/0010550 A1 | 1/2007 | Mckenzie |
| 2007/0014839 A1 | 1/2007 | Bracht |
| 2007/0015698 A1 | 1/2007 | Goldstein et al. |
| 2007/0021360 A1 | 1/2007 | Nyce et al. |
| 2007/0027201 A1 | 2/2007 | McComas et al. |
| 2007/0031491 A1 | 2/2007 | Levine et al. |
| 2007/0036843 A1 | 2/2007 | Hirsh et al. |
| 2007/0037780 A1 | 2/2007 | Anigbogu et al. |
| 2007/0037782 A1 | 2/2007 | Suzuki et al. |
| 2007/0042038 A1 | 2/2007 | Besse |
| 2007/0060589 A1 | 3/2007 | Purandare et al. |
| 2007/0066628 A1 | 3/2007 | Zhang et al. |
| 2007/0066637 A1 | 3/2007 | Zhang et al. |
| 2007/0066675 A1 | 3/2007 | Zhang et al. |
| 2007/0071777 A1 | 3/2007 | Bromer et al. |
| 2007/0078091 A1 | 4/2007 | Hubler et al. |
| 2007/0088029 A1 | 4/2007 | Balog et al. |
| 2007/0093548 A1 | 4/2007 | Diffendal et al. |
| 2007/0116729 A1 | 5/2007 | Palepu |
| 2007/0116829 A1 | 5/2007 | Prakash et al. |
| 2007/0128263 A1 | 6/2007 | Wall et al. |
| 2007/0154533 A1 | 7/2007 | Dudley |
| 2007/0167418 A1 | 7/2007 | Ferguson |
| 2007/0178166 A1 | 8/2007 | Bernstein et al. |
| 2007/0184558 A1 | 8/2007 | Roth et al. |
| 2007/0185068 A1 | 8/2007 | Ferguson et al. |
| 2007/0190022 A1 | 8/2007 | Chiao et al. |
| 2007/0191319 A1 | 8/2007 | Ke et al. |
| 2007/0191321 A1 | 8/2007 | Ahmed et al. |
| 2007/0196415 A1 | 8/2007 | Houston et al. |
| 2007/0196433 A1 | 8/2007 | Ron et al. |
| 2007/0207225 A1 | 9/2007 | Squadrito |
| 2007/0225281 A1 | 9/2007 | Zhang et al. |
| 2007/0232574 A1 | 10/2007 | Bernard et al. |
| 2007/0238713 A1 | 10/2007 | Gast et al. |
| 2007/0243229 A1 | 10/2007 | Smith et al. |
| 2007/0248658 A1 | 10/2007 | Bracht et al. |
| 2007/0254858 A1 | 11/2007 | Cronk |
| 2007/0255197 A1 | 11/2007 | Wilkins et al. |
| 2007/0264309 A1 | 11/2007 | Chollet et al. |
| 2007/0264345 A1 | 11/2007 | Eros et al. |
| 2007/0264349 A1 | 11/2007 | Lee et al. |
| 2007/0270394 A1 | 11/2007 | El-Alfy et al. |
| 2007/0286819 A1 | 12/2007 | DeVries et al. |
| 2007/0287688 A1 | 12/2007 | Chan et al. |
| 2007/0287789 A1 | 12/2007 | Jones et al. |
| 2007/0292359 A1 | 12/2007 | Schuz et al. |
| 2007/0292387 A1 | 12/2007 | Jon et al. |
| 2007/0292461 A1 | 12/2007 | Danziger et al. |
| 2007/0292493 A1 | 12/2007 | Brierre |
| 2007/0298089 A1 | 12/2007 | Yoshinaga et al. |
| 2008/0026035 A1 | 1/2008 | Chollet et al. |
| 2008/0026040 A1 | 1/2008 | Rivera et al. |
| 2008/0026062 A1 | 1/2008 | Farr et al. |
| 2008/0038219 A1 | 2/2008 | Carlson et al. |
| 2008/0038350 A1 | 2/2008 | Gerecke et al. |
| 2008/0039405 A1 | 2/2008 | Joseph et al. |
| 2008/0050317 A1 | 2/2008 | Besonov et al. |
| 2008/0051351 A1 | 2/2008 | Ghisalberti |
| 2008/0063607 A1 | 3/2008 | Berman et al. |
| 2008/0069779 A1 | 3/2008 | Schuz et al. |
| 2008/0069791 A1 | 3/2008 | Beissert |
| 2008/0085877 A1 | 4/2008 | Bortz |
| 2008/0095831 A1 | 4/2008 | Mc Graw |
| 2008/0095838 A1 | 4/2008 | Abou Chacra-Vernet |
| 2008/0119537 A1 | 5/2008 | Zhang et al. |
| 2008/0125402 A1 | 5/2008 | Dilberti |
| 2008/0138379 A1 | 6/2008 | Jennings-Spring |
| 2008/0138390 A1 | 6/2008 | Gricenko et al. |
| 2008/0139392 A1 | 6/2008 | Yuan et al. |
| 2008/0145423 A1 | 6/2008 | Khan et al. |
| 2008/0153789 A1 | 6/2008 | Dmowski et al. |
| 2008/0175814 A1 | 7/2008 | Phiasivongsa et al. |
| 2008/0175905 A1 | 7/2008 | Biksh et al. |
| 2008/0175908 A1 | 7/2008 | Biksh et al. |
| 2008/0188829 A1 | 8/2008 | Creasy |
| 2008/0206156 A1 | 8/2008 | Cronk |
| 2008/0206159 A1 | 8/2008 | Schuz et al. |
| 2008/0206161 A1 | 8/2008 | Tamarkin et al. |
| 2008/0214512 A1 | 9/2008 | Seitz et al. |
| 2008/0220069 A1 | 9/2008 | Allison |
| 2008/0226698 A1 | 9/2008 | Beste et al. |
| 2008/0227763 A1 | 9/2008 | Paris et al. |
| 2008/0234199 A1 | 9/2008 | Katamreddy |
| 2008/0234240 A1 | 9/2008 | Duesterberg et al. |
| 2008/0255078 A1 | 10/2008 | Katamreddy |
| 2008/0255089 A1 | 10/2008 | Katamreddy |
| 2008/0261931 A1 | 10/2008 | Stenlof et al. |
| 2008/0113953 A1 | 12/2008 | DeVries et al. |
| 2008/0114050 A1 | 12/2008 | Fensome et al. |
| 2008/0299220 A1 | 12/2008 | Tamarkin et al. |
| 2008/0306036 A1 | 12/2008 | Katamreddy |
| 2008/0312197 A1 | 12/2008 | Rodriguez |
| 2008/0312198 A1 | 12/2008 | Rodriguez |
| 2008/0319078 A1 | 12/2008 | Katamreddy |
| 2009/0004246 A1 | 1/2009 | Woolfson et al. |
| 2009/0010968 A1 | 1/2009 | Peyrot et al. |
| 2009/0011041 A1 | 1/2009 | Musaeva et al. |
| 2009/0017120 A1 | 1/2009 | Brisco et al. |
| 2009/0022683 A1 | 1/2009 | Park et al. |
| 2009/0047357 A1 | 2/2009 | Tomohira et al. |
| 2009/0053294 A1 | 2/2009 | Prendergast |
| 2009/0060982 A1 | 3/2009 | Ron et al. |
| 2009/0060997 A1 | 3/2009 | Seitz et al. |
| 2009/0068118 A1 | 3/2009 | Eini et al. |
| 2009/0074859 A1 | 3/2009 | Patel |
| 2009/0081206 A1 | 3/2009 | Leibovitz |
| 2009/0081278 A1 | 3/2009 | De Graaff et al. |
| 2009/0081303 A1 | 3/2009 | Savoir et al. |
| 2009/0092656 A1 | 4/2009 | Klamerus et al. |
| 2009/0093440 A1 | 4/2009 | Murad |
| 2009/0098069 A1 | 4/2009 | Vacca |
| 2009/0099106 A1 | 4/2009 | Phiasivongsa et al. |
| 2009/0099149 A1 | 4/2009 | Kresevic |
| 2009/0130029 A1 | 5/2009 | Tamarkin et al. |
| 2009/0131385 A1 | 5/2009 | Voskuhl |
| 2009/0136574 A1 | 5/2009 | Diaz-Astruc et al. |
| 2009/0137478 A1 | 5/2009 | Bernstein et al. |
| 2009/0137538 A1 | 5/2009 | Klamerus et al. |
| 2009/0143344 A1 | 6/2009 | Chang |
| 2009/0164341 A1 | 6/2009 | Sunvold et al. |
| 2009/0175799 A1 | 7/2009 | Tamarkin et al. |
| 2009/0181088 A1 | 7/2009 | Song et al. |
| 2009/0186081 A1 | 7/2009 | Slot et al. |
| 2009/0197843 A1 | 8/2009 | Notelovitz et al. |
| 2009/0203658 A1 | 8/2009 | Rose et al. |
| 2009/0214474 A1 | 8/2009 | Jennings |
| 2009/0227025 A1 | 9/2009 | Nichols et al. |
| 2009/0227550 A1 | 9/2009 | Mattern |
| 2009/0232897 A1 | 9/2009 | Sahoo et al. |

(56) References Cited

U.S. PATENT DOCUMENTS

| | | |
|---|---|---|
| 2009/0258096 A1 | 10/2009 | Cohen |
| 2009/0264395 A1 | 10/2009 | Creasy |
| 2009/0269403 A1 | 10/2009 | Shaked et al. |
| 2009/0285772 A1 | 11/2009 | Phiasivongsa et al. |
| 2009/0285869 A1 | 11/2009 | Trimble |
| 2009/0318558 A1 | 12/2009 | Kim et al. |
| 2009/0324714 A1 | 12/2009 | Kresevic et al. |
| 2009/0325916 A1 | 12/2009 | Zhang et al. |
| 2010/0008985 A1 | 1/2010 | Vermeulen et al. |
| 2010/0028360 A1 | 2/2010 | Atwood |
| 2010/0034838 A1 | 2/2010 | Staniforth et al. |
| 2010/0034880 A1 | 2/2010 | Sintov |
| 2010/0040671 A1 | 2/2010 | Ahmed et al. |
| 2010/0048523 A1 | 2/2010 | Bachman et al. |
| 2010/0055138 A1 | 3/2010 | Jacobs et al. |
| 2010/0074959 A1 | 3/2010 | Hansom et al. |
| 2010/0086501 A1 | 4/2010 | Chang et al. |
| 2010/0086599 A1 | 4/2010 | Huempel et al. |
| 2010/0092568 A1 | 4/2010 | Lerner et al. |
| 2010/0105071 A1 | 4/2010 | Laufer et al. |
| 2010/0119585 A1 | 5/2010 | Hille et al. |
| 2010/0129320 A1 | 5/2010 | Phiasivongsa et al. |
| 2010/0136105 A1 | 6/2010 | Chen et al. |
| 2010/0137265 A1 | 6/2010 | Leonard |
| 2010/0137271 A1 | 6/2010 | Chen et al. |
| 2010/0143420 A1 | 6/2010 | Lee et al. |
| 2010/0143481 A1 | 6/2010 | Shenoy et al. |
| 2010/0150993 A1 | 6/2010 | Theobald et al. |
| 2010/0152144 A1 | 6/2010 | Hermsmeyer |
| 2010/0168228 A1 | 7/2010 | Bose et al. |
| 2010/0183723 A1 | 7/2010 | Laurent-Applegate et al. |
| 2010/0184736 A1 | 7/2010 | Coelingh Bennink et al. |
| 2010/0190758 A1 | 7/2010 | Fauser et al. |
| 2010/0204326 A1 | 8/2010 | D Souza |
| 2010/0210994 A1 | 8/2010 | Zarif |
| 2010/0221195 A1 | 9/2010 | Ziv et al. |
| 2010/0227797 A1 | 9/2010 | Danielsson et al. |
| 2010/0240626 A1 | 9/2010 | Kulkarni et al. |
| 2010/0247482 A1 | 9/2010 | Chen et al. |
| 2010/0247632 A1 | 9/2010 | Dong et al. |
| 2010/0247635 A1 | 9/2010 | Schmidt et al. |
| 2010/0255085 A1* | 10/2010 | Liu .................. A61K 9/4858 424/456 |
| 2010/0273730 A1 | 10/2010 | Hsu et al. |
| 2010/0278759 A1 | 11/2010 | Murad |
| 2010/0279988 A1 | 11/2010 | Setiawan et al. |
| 2010/0291191 A1 | 11/2010 | Lapitsky et al. |
| 2010/0292199 A1 | 11/2010 | Leverd et al. |
| 2010/0303825 A9 | 12/2010 | Sirbasku |
| 2010/0312137 A1 | 12/2010 | Gilmour et al. |
| 2010/0316724 A1 | 12/2010 | Whitfield et al. |
| 2010/0322884 A1 | 12/2010 | Wilkins et al. |
| 2010/0330168 A1 | 12/2010 | Gicquel et al. |
| 2011/0028439 A1 | 2/2011 | Witt-Enderby et al. |
| 2011/0039814 A1 | 2/2011 | Ross et al. |
| 2011/0053845 A1 | 3/2011 | Levine et al. |
| 2011/0066473 A1 | 3/2011 | Bernick et al. |
| 2011/0076775 A1 | 3/2011 | Stewart et al. |
| 2011/0076776 A1 | 3/2011 | Stewart et al. |
| 2011/0086825 A1 | 4/2011 | Chatroux |
| 2011/0087192 A1 | 4/2011 | Uhland et al. |
| 2011/0091555 A1 | 4/2011 | De Luigi Bruschi et al. |
| 2011/0098258 A1 | 4/2011 | Canet et al. |
| 2011/0098631 A1 | 4/2011 | McIntyre et al. |
| 2011/0104268 A1 | 5/2011 | Segot et al. |
| 2011/0104289 A1 | 5/2011 | Savoir Vilboeuf et al. |
| 2011/0130372 A1 | 6/2011 | Marliani et al. |
| 2011/0135719 A1 | 6/2011 | Besins et al. |
| 2011/0142945 A1 | 6/2011 | Chen et al. |
| 2011/0152840 A1 | 6/2011 | Lee et al. |
| 2011/0158920 A1 | 6/2011 | Fisher et al. |
| 2011/0171140 A1 | 7/2011 | Illum et al. |
| 2011/0182997 A1 | 7/2011 | Lewis et al. |
| 2011/0190201 A1 | 8/2011 | Wood, Jr. et al. |
| 2011/0195031 A1 | 8/2011 | Du |
| 2011/0195114 A1 | 8/2011 | Carrara et al. |
| 2011/0195944 A1 | 8/2011 | Mura et al. |
| 2011/0217341 A1 | 9/2011 | Sah |
| 2011/0238003 A1 | 9/2011 | Karabelas et al. |
| 2011/0244043 A1 | 10/2011 | Wang et al. |
| 2011/0250256 A1 | 10/2011 | Hyun et al. |
| 2011/0250259 A1 | 10/2011 | Buckman |
| 2011/0250274 A1 | 10/2011 | Shaked et al. |
| 2011/0256092 A1 | 10/2011 | Phiasivongsa |
| 2011/0262373 A1 | 10/2011 | Umbert |
| 2011/0262494 A1 | 10/2011 | Achleitner et al. |
| 2011/0268665 A1 | 11/2011 | Tamarkin et al. |
| 2011/0275584 A1 | 11/2011 | Volkmann et al. |
| 2011/0281832 A1 | 11/2011 | Wennogle et al. |
| 2011/0287094 A1 | 11/2011 | Penhasi et al. |
| 2011/0293720 A1 | 12/2011 | General et al. |
| 2011/0294738 A1 | 12/2011 | Kuliopulos et al. |
| 2011/0300167 A1 | 12/2011 | Covic et al. |
| 2011/0301087 A1 | 12/2011 | Mcbride et al. |
| 2011/0306579 A1 | 12/2011 | Stein |
| 2011/0311592 A1 | 12/2011 | Birbara |
| 2011/0312927 A1 | 12/2011 | Nachaegari et al. |
| 2011/0312928 A1 | 12/2011 | Nachaegari et al. |
| 2011/0318405 A1 | 12/2011 | Erwin |
| 2011/0318431 A1 | 12/2011 | Gulati |
| 2012/0009276 A1 | 1/2012 | De Groote |
| 2012/0015350 A1 | 1/2012 | Nabatiyan et al. |
| 2012/0021041 A1 | 1/2012 | Rossi et al. |
| 2012/0028888 A1 | 2/2012 | Janz et al. |
| 2012/0028910 A1 | 2/2012 | Takruri et al. |
| 2012/0028936 A1 | 2/2012 | Popova et al. |
| 2012/0045532 A1 | 2/2012 | Cohen |
| 2012/0046264 A1 | 2/2012 | Lieb et al. |
| 2012/0046518 A1 | 2/2012 | Yoakum et al. |
| 2012/0052077 A1 | 3/2012 | Truitt, III et al. |
| 2012/0058171 A1 | 3/2012 | Zeeman et al. |
| 2012/0058962 A1 | 3/2012 | Sparrow et al. |
| 2012/0058979 A1 | 3/2012 | Auspitz et al. |
| 2012/0064135 A1 | 3/2012 | Harms et al. |
| 2012/0065179 A1 | 3/2012 | Andersson |
| 2012/0065221 A1 | 3/2012 | Babul |
| 2012/0087872 A1 | 4/2012 | Schuz et al. |
| 2012/0101073 A1 | 4/2012 | Mannion |
| 2012/0121517 A1 | 5/2012 | Kim et al. |
| 2012/0121692 A1 | 5/2012 | Fang et al. |
| 2012/0122829 A1 | 5/2012 | Masini et al. |
| 2012/0128625 A1 | 5/2012 | Shalwitz et al. |
| 2012/0128654 A1 | 5/2012 | Terpstra et al. |
| 2012/0128683 A1 | 5/2012 | Shantha |
| 2012/0128733 A1 | 5/2012 | Perrin et al. |
| 2012/0128777 A1 | 5/2012 | Keck et al. |
| 2012/0129773 A1 | 5/2012 | Geier et al. |
| 2012/0129819 A1 | 5/2012 | Vancaillie et al. |
| 2012/0136013 A1 | 5/2012 | Wennogle et al. |
| 2012/0142645 A1 | 6/2012 | Marx |
| 2012/0148670 A1 | 6/2012 | Lee et al. |
| 2012/0149748 A1 | 6/2012 | Shanler et al. |
| 2012/0172343 A1 | 7/2012 | Schuermann et al. |
| 2012/0184515 A1 | 7/2012 | Schwede et al. |
| 2012/0231052 A1 | 9/2012 | Brinton et al. |
| 2012/0232011 A1 | 9/2012 | Kneissel et al. |
| 2012/0232042 A1 | 9/2012 | Krenz et al. |
| 2012/0263679 A1 | 10/2012 | Wallace et al. |
| 2012/0269721 A1 | 10/2012 | Weng et al. |
| 2012/0277249 A1 | 11/2012 | Tarrand et al. |
| 2012/0277727 A1 | 11/2012 | Doshi et al. |
| 2012/0283671 A1 | 11/2012 | Shibata et al. |
| 2012/0295911 A1 | 11/2012 | Mannion et al. |
| 2012/0301517 A1 | 11/2012 | Warner et al. |
| 2012/0301538 A1 | 11/2012 | Latere et al. |
| 2012/0302535 A1 | 11/2012 | Caufriez et al. |
| 2012/0316130 A1 | 12/2012 | Hendrix |
| 2012/0316496 A1 | 12/2012 | Horres et al. |
| 2012/0321579 A1 | 12/2012 | Edelson et al. |
| 2012/0322779 A9 | 12/2012 | Voskuhl |
| 2012/0328549 A1 | 12/2012 | Edelson et al. |
| 2012/0329738 A1 | 12/2012 | Liu |
| 2013/0004619 A1 | 1/2013 | Goh et al. |
| 2013/0011342 A1 | 1/2013 | Hazot et al. |

(56) References Cited

U.S. PATENT DOCUMENTS

| | | |
|---|---|---|
| 2013/0017239 A1 | 1/2013 | Fernandez et al. |
| 2013/0022674 A1 | 1/2013 | Dudley et al. |
| 2013/0023505 A1 | 1/2013 | Garfield et al. |
| 2013/0023823 A1 | 1/2013 | Volland et al. |
| 2013/0028850 A1 | 1/2013 | Hazot et al. |
| 2013/0029947 A1 | 1/2013 | Nachaegari et al. |
| 2013/0029957 A1 | 1/2013 | Venkateshwaran et al. |
| 2013/0045266 A1 | 2/2013 | Kang et al. |
| 2013/0045953 A1 | 2/2013 | Grenier et al. |
| 2013/0059795 A1 | 3/2013 | Lo et al. |
| 2013/0064897 A1 | 3/2013 | Binay |
| 2013/0072466 A1 | 3/2013 | Choi et al. |
| 2013/0084257 A1 | 4/2013 | Ishida et al. |
| 2013/0085123 A1 | 4/2013 | Zhao et al. |
| 2013/0089574 A1 | 4/2013 | Stock et al. |
| 2013/0090318 A1 | 4/2013 | Gainer et al. |
| 2013/0102781 A1 | 4/2013 | Ely et al. |
| 2013/0108551 A1 | 5/2013 | Gruell et al. |
| 2013/0116215 A1 | 5/2013 | Lleo et al. |
| 2013/0116222 A1 | 5/2013 | Altomari et al. |
| 2013/0122051 A1 | 5/2013 | Gullapalli et al. |
| 2013/0123175 A1 | 5/2013 | Mckee et al. |
| 2013/0123220 A1 | 5/2013 | Queiroz |
| 2013/0123351 A1 | 5/2013 | Dewitt |
| 2013/0129818 A1 | 5/2013 | Bernick et al. |
| 2013/0131027 A1 | 5/2013 | Schmitz et al. |
| 2013/0131028 A1 | 5/2013 | Snyder et al. |
| 2013/0131029 A1 | 5/2013 | Baltussen et al. |
| 2013/0149314 A1 | 6/2013 | Bullerdiek et al. |
| 2013/0164225 A1 | 6/2013 | Besonov et al. |
| 2013/0164346 A1 | 6/2013 | Son et al. |
| 2013/0165744 A1 | 6/2013 | Carson et al. |
| 2013/0178452 A1 | 7/2013 | King |
| 2013/0183254 A1 | 7/2013 | Cochran et al. |
| 2013/0183325 A1 | 7/2013 | Sforzini et al. |
| 2013/0189193 A1 | 7/2013 | Besonov et al. |
| 2013/0189196 A1 | 7/2013 | Tamarkin et al. |
| 2013/0189230 A1 | 7/2013 | Kooy et al. |
| 2013/0189368 A1 | 7/2013 | Mosqueira et al. |
| 2013/0210709 A1 | 8/2013 | Covic et al. |
| 2013/0216550 A1 | 8/2013 | Penninger et al. |
| 2013/0216596 A1 | 8/2013 | Fernandez et al. |
| 2013/0224177 A1 | 8/2013 | Kim et al. |
| 2013/0224257 A1 | 8/2013 | Sah et al. |
| 2013/0224268 A1 | 8/2013 | Jaikaria et al. |
| 2013/0224300 A1 | 8/2013 | Maggio |
| 2013/0225412 A1 | 8/2013 | Sardari et al. |
| 2013/0225542 A1 | 8/2013 | Frick et al. |
| 2013/0226113 A1 | 8/2013 | Langguth et al. |
| 2013/0243696 A1 | 9/2013 | Wang et al. |
| 2013/0245253 A1 | 9/2013 | Mook et al. |
| 2013/0245570 A1 | 9/2013 | Jackson |
| 2013/0261096 A1 | 10/2013 | Merian et al. |
| 2013/0266645 A1 | 10/2013 | Schoenecker et al. |
| 2013/0267485 A1 | 10/2013 | Da Silva |
| 2013/0273167 A1 | 10/2013 | Kim et al. |
| 2013/0274211 A1 | 10/2013 | Prusthy et al. |
| 2013/0280213 A1 | 10/2013 | Voskuhl |
| 2013/0316374 A1 | 11/2013 | Menon et al. |
| 2013/0317065 A1 | 11/2013 | Seto et al. |
| 2013/0317315 A1 | 11/2013 | Tsang et al. |
| 2013/0324565 A1 | 12/2013 | Zhao et al. |
| 2013/0331363 A1 | 12/2013 | Zhao et al. |
| 2013/0338122 A1 | 12/2013 | Bernick et al. |
| 2013/0338123 A1 | 12/2013 | Bernick et al. |
| 2013/0338124 A1 | 12/2013 | Zhao et al. |
| 2013/0345187 A1 | 12/2013 | Rodriguez |
| 2014/0018335 A1 | 1/2014 | Seto et al. |
| 2014/0024590 A1 | 1/2014 | Taylor et al. |
| 2014/0031289 A1 | 1/2014 | Kim et al. |
| 2014/0031323 A1 | 1/2014 | Perez |
| 2014/0066416 A1 | 3/2014 | Leunis et al. |
| 2014/0072531 A1 | 3/2014 | Oh et al. |
| 2014/0079686 A1 | 3/2014 | Prouty et al. |
| 2014/0088051 A1 | 3/2014 | Bernick et al. |
| 2014/0088058 A1 | 3/2014 | Maurizio |
| 2014/0088059 A1 | 3/2014 | Santha et al. |
| 2014/0094426 A1 | 4/2014 | Drummond et al. |
| 2014/0094440 A1 | 4/2014 | Bernick et al. |
| 2014/0094441 A1 | 4/2014 | Bernick et al. |
| 2014/0099362 A1 | 4/2014 | Bernick et al. |
| 2014/0100159 A1 | 4/2014 | Conrad |
| 2014/0100204 A1 | 4/2014 | Bernick et al. |
| 2014/0100205 A1 | 4/2014 | Bernick et al. |
| 2014/0100206 A1 | 4/2014 | Cacace et al. |
| 2014/0113889 A1 | 4/2014 | Haine et al. |
| 2014/0127185 A1 | 5/2014 | Sayeed et al. |
| 2014/0127280 A1 | 5/2014 | Jukarainen et al. |
| 2014/0127308 A1 | 5/2014 | Opara et al. |
| 2014/0128798 A1 | 5/2014 | Malanchin et al. |
| 2014/0148491 A1 | 5/2014 | Valia et al. |
| 2014/0186332 A1 | 7/2014 | Ezrin et al. |
| 2014/0187487 A1 | 7/2014 | Shoichet et al. |
| 2014/0193523 A1 | 7/2014 | Henry |
| 2014/0194396 A1 | 7/2014 | Wennogle et al. |
| 2014/0206616 A1 | 7/2014 | Ko et al. |
| 2014/0213565 A1 | 7/2014 | Bernick et al. |
| 2014/0329783 A1 | 11/2014 | Bernick et al. |
| 2014/0370084 A1 | 12/2014 | Bernick et al. |
| 2014/0371182 A1 | 12/2014 | Bernick et al. |
| 2014/0371183 A1 | 12/2014 | Bernick et al. |
| 2014/0371184 A1 | 12/2014 | Bernick et al. |
| 2014/0371185 A1 | 12/2014 | Bernick et al. |
| 2015/0031654 A1 | 1/2015 | Amadio |
| 2015/0045335 A1 | 2/2015 | Bernick et al. |
| 2015/0133421 A1 | 5/2015 | Bernick et al. |
| 2015/0148323 A1 | 5/2015 | Bernick et al. |
| 2015/0164789 A1 | 6/2015 | Bernick et al. |
| 2015/0224117 A1 | 8/2015 | Bernick et al. |
| 2015/0224118 A1 | 8/2015 | Bernick et al. |
| 2015/0297733 A1 | 10/2015 | Oberegger et al. |
| 2015/0302435 A1 | 10/2015 | Bernick et al. |
| 2015/0342963 A1 | 12/2015 | Bernick et al. |
| 2015/0352126 A1 | 12/2015 | Bernick et al. |
| 2015/0359737 A1 | 12/2015 | Bernick et al. |
| 2016/0030449 A1 | 2/2016 | Persicaner et al. |
| 2016/0213685 A1 | 7/2016 | Bernick et al. |
| 2017/0056418 A1 | 3/2017 | Thorsteinsson et al. |
| 2017/0216310 A1 | 8/2017 | Mirkin et al. |
| 2017/0281645 A1 | 10/2017 | Shadiack et al. |
| 2017/0281646 A1 | 10/2017 | Inskeep et al. |
| 2017/0281647 A1 | 10/2017 | Shadiack et al. |
| 2017/0281776 A1 | 10/2017 | Shadiack et al. |
| 2018/0161343 A1 | 6/2018 | Mirkin et al. |
| 2018/0161344 A1 | 6/2018 | Mirkin et al. |
| 2018/0161345 A1 | 6/2018 | Bernick et al. |
| 2018/0221389 A1 | 8/2018 | Amadio et al. |

FOREIGN PATENT DOCUMENTS

| | | |
|---|---|---|
| CA | 2612380 | 12/2006 |
| CN | 102258455 A | 11/2011 |
| EP | 0261429 A1 | 3/1988 |
| EP | 0275716 A1 | 7/1988 |
| EP | 0279977 A2 | 8/1988 |
| EP | 0622075 A1 | 11/1994 |
| EP | 0785211 A1 | 7/1997 |
| EP | 0785212 A1 | 7/1997 |
| EP | 0811381 A1 | 12/1997 |
| EP | 0904064 A1 | 3/1999 |
| EP | 0813412 B1 | 12/1999 |
| EP | 0750495 B1 | 12/2002 |
| EP | 1300152 A1 | 4/2003 |
| EP | 1094781 B1 | 7/2008 |
| EP | 2191833 A1 | 6/2010 |
| GB | 452238 A | 8/1936 |
| GB | 720561 A | 12/1954 |
| GB | 848881 A | 9/1960 |
| GB | 874368 A | 8/1961 |
| GB | 1589946 A | 5/1981 |
| IN | 2005KOL00053 | 8/2005 |
| IN | 216026 | 3/2008 |
| IN | 244217 | 11/2010 |
| JP | H4-503810 | 9/1990 |

(56) References Cited

FOREIGN PATENT DOCUMENTS

| | | |
|---|---|---|
| JP | H2-264725 A | 10/1990 |
| JP | H 10-251116 A | 9/1998 |
| JP | 2002 510336 A | 4/2002 |
| JP | 2006 513182 A | 4/2006 |
| RU | 2155582 C2 | 9/2000 |
| RU | 2449796 C2 | 2/2006 |
| WO | 199010425 A1 | 9/1990 |
| WO | 1990011064 | 10/1990 |
| WO | 1993017686 | 9/1993 |
| WO | 1994022426 | 10/1994 |
| WO | 1995005807 | 3/1995 |
| WO | 1995030409 | 11/1995 |
| WO | 1996009826 | 4/1996 |
| WO | 1996019975 | 7/1996 |
| WO | 1996030000 | 10/1996 |
| WO | 1997005491 | 2/1997 |
| WO | 1997043989 | 11/1997 |
| WO | 1998010293 | 3/1998 |
| WO | 1998032465 | 7/1998 |
| WO | 1998041217 A1 | 9/1998 |
| WO | 1998051280 | 11/1998 |
| WO | 1999022680 A1 | 5/1999 |
| WO | 1999032072 | 7/1999 |
| WO | 1999039700 | 8/1999 |
| WO | 1999042109 | 8/1999 |
| WO | 1999043304 | 9/1999 |
| WO | 1999048477 | 9/1999 |
| WO | 1999052528 A1 | 10/1999 |
| WO | 1999053910 | 10/1999 |
| WO | 1999055333 A1 | 11/1999 |
| WO | 1999062497 A1 | 12/1999 |
| WO | 1999063974 | 12/1999 |
| WO | 2000001351 | 1/2000 |
| WO | 2000006175 | 2/2000 |
| WO | 2000038659 | 6/2000 |
| WO | 2000045795 | 8/2000 |
| WO | 2000050007 | 8/2000 |
| WO | 2000059577 | 10/2000 |
| WO | 2000076522 | 12/2000 |
| WO | 2001037808 | 5/2001 |
| WO | 2001054699 | 8/2001 |
| WO | 2001060325 | 8/2001 |
| WO | 2001087276 | 11/2001 |
| WO | 2001091757 | 12/2001 |
| WO | 2002007700 | 1/2002 |
| WO | 2002011768 | 2/2002 |
| WO | 2002022132 | 3/2002 |
| WO | 2002040008 | 5/2002 |
| WO | 2002041878 | 5/2002 |
| WO | 2002053131 | 7/2002 |
| WO | 2002078602 | 10/2002 |
| WO | 2002078604 | 10/2002 |
| WO | 2003028667 | 4/2003 |
| WO | 2003041718 | 5/2003 |
| WO | 2003041741 | 5/2003 |
| WO | 2003068186 | 8/2003 |
| WO | 2003077923 | 9/2003 |
| WO | 2003082254 | 10/2003 |
| WO | 2003092588 | 11/2003 |
| WO | 2004014397 A1 | 2/2004 |
| WO | 2004014432 | 2/2004 |
| WO | 2004017983 | 3/2004 |
| WO | 2004032897 | 4/2004 |
| WO | 2004032942 A1 | 4/2004 |
| WO | 2004052336 | 6/2004 |
| WO | 2004054540 | 7/2004 |
| WO | 2004054576 A1 | 7/2004 |
| WO | 2004080413 | 9/2004 |
| WO | 2004105694 A2 | 12/2004 |
| WO | 2004110402 A1 | 12/2004 |
| WO | 2004110408 A2 | 12/2004 |
| WO | 2005027911 | 3/2005 |
| WO | 2005030175 | 4/2005 |
| WO | 2005081825 | 9/2005 |
| WO | 2005087194 | 9/2005 |
| WO | 2005087199 | 9/2005 |
| WO | 2005105059 | 11/2005 |
| WO | 2005115335 | 12/2005 |
| WO | 2005120470 | 12/2005 |
| WO | 2005120517 | 12/2005 |
| WO | 2006013369 | 2/2006 |
| WO | 2006034090 | 3/2006 |
| WO | 2006036899 | 4/2006 |
| WO | 2006053172 | 5/2006 |
| WO | 2006105615 | 10/2006 |
| WO | 2006113505 | 10/2006 |
| WO | 2006138686 | 12/2006 |
| WO | 2006138735 | 12/2006 |
| WO | 2007045027 | 4/2007 |
| WO | 2007076144 A2 | 7/2007 |
| WO | 2007103294 | 9/2007 |
| WO | 2007120868 | 10/2007 |
| WO | 2007123790 | 11/2007 |
| WO | 2007124250 | 11/2007 |
| WO | 2007144151 | 12/2007 |
| WO | 2008049516 | 5/2008 |
| WO | 2008152444 | 12/2008 |
| WO | 2009002542 | 12/2008 |
| WO | 2009036311 | 3/2009 |
| WO | 2009040818 | 4/2009 |
| WO | 2009069006 | 6/2009 |
| WO | 2009098072 | 8/2009 |
| WO | 2009133352 | 11/2009 |
| WO | 2010033188 | 3/2010 |
| WO | 2010146872 | 12/2010 |
| WO | 2011000210 | 1/2011 |
| WO | 2011073995 | 6/2011 |
| WO | 2011120084 | 10/2011 |
| WO | 2011128336 | 10/2011 |
| WO | 2012009778 | 1/2012 |
| WO | 2012024361 | 2/2012 |
| WO | 2012055814 A1 | 5/2012 |
| WO | 2012055840 A1 | 5/2012 |
| WO | 2012065740 | 5/2012 |
| WO | 2012098090 A1 | 7/2012 |
| WO | 2012116277 A1 | 8/2012 |
| WO | 2012118563 A2 | 9/2012 |
| WO | 2012120365 A1 | 9/2012 |
| WO | 2012127501 A2 | 9/2012 |
| WO | 2012156561 A1 | 11/2012 |
| WO | 2012156822 A1 | 11/2012 |
| WO | 2012158483 A2 | 11/2012 |
| WO | 2012166909 A1 | 12/2012 |
| WO | 2012170578 A1 | 12/2012 |
| WO | 2013011501 A1 | 1/2013 |
| WO | 2013025449 A1 | 2/2013 |
| WO | 2013028639 A1 | 2/2013 |
| WO | 2013035101 A1 | 3/2013 |
| WO | 2013044067 A1 | 3/2013 |
| WO | 2013045404 A2 | 4/2013 |
| WO | 2013059285 A1 | 4/2013 |
| WO | 2013063279 A1 | 5/2013 |
| WO | 2013064620 A1 | 5/2013 |
| WO | 2013071281 A1 | 5/2013 |
| WO | 2013078422 A2 | 5/2013 |
| WO | 2013088254 | 6/2013 |
| WO | 2013102665 A1 | 7/2013 |
| WO | 2013106437 A1 | 7/2013 |
| WO | 2013112947 A1 | 8/2013 |
| WO | 2013113690 | 8/2013 |
| WO | 2013124415 A1 | 8/2013 |
| WO | 2013127727 A1 | 9/2013 |
| WO | 2013127728 A1 | 9/2013 |
| WO | 2013144356 A1 | 10/2013 |
| WO | 2013149258 A2 | 10/2013 |
| WO | 2013158454 A2 | 10/2013 |
| WO | 2013170052 A1 | 11/2013 |
| WO | 2013178587 A1 | 12/2013 |
| WO | 2013181449 A1 | 12/2013 |
| WO | 2013192248 | 12/2013 |
| WO | 2013192249 | 12/2013 |
| WO | 2013192250 | 12/2013 |
| WO | 2013192251 | 12/2013 |
| WO | 2014001904 A1 | 1/2014 |

(56) References Cited

FOREIGN PATENT DOCUMENTS

| | | |
|---|---|---|
| WO | 2014004424 A1 | 1/2014 |
| WO | 2014009434 A1 | 1/2014 |
| WO | 2014018569 A1 | 1/2014 |
| WO | 2014018570 A1 | 1/2014 |
| WO | 2014018571 A2 | 1/2014 |
| WO | 2014018856 A1 | 1/2014 |
| WO | 2014018932 A2 | 1/2014 |
| WO | 2014031958 A1 | 2/2014 |
| WO | 2014041120 A1 | 3/2014 |
| WO | 2014052792 A1 | 4/2014 |
| WO | 2014056897 A1 | 4/2014 |
| WO | 2014066442 A2 | 5/2014 |
| WO | 2014074846 A1 | 5/2014 |
| WO | 2014076231 A1 | 5/2014 |
| WO | 2014076569 A2 | 5/2014 |
| WO | 2014081598 A1 | 5/2014 |
| WO | 2014086739 A1 | 6/2014 |
| WO | 2014093114 A1 | 6/2014 |
| WO | 2014104784 A1 | 7/2014 |
| WO | 2015179782 A1 | 11/2015 |
| WO | 2016018993 A1 | 2/2016 |

OTHER PUBLICATIONS

Chambin et al, "Interest of Multifunctional Lipid Excipients: Case of Gelucire® 44/14," Drug Development and Industrial Pharmacy, vol. 31, No. 6, pp. 527-534 (Year: 2005).*
Abbas et at, Regression of endometrial implants treated with vitamin $D_3$ in a rat model of endometriosis, European J of Pharma, 715 (2013) 72-75, Elsevier.
Abitec, CapmulMCM, EP, Technical Data Sheet, version 10, 2014, Columbus, OH.
Abitec, CapmulMCM, NF, Technical Data Sheet, version 6, 2014, Columbus, OH.
Abitec, CapmulMCM, Saftey Data Sheet, 2011, Janesville, WI.
Abitec, CapmulMCM, Technical Data Sheet, version 17, 2014, Columbus, OH.
Abitec, CapmulPG8, CAS No. 31565-12-5, version 11, 2006, Columbus, OH.
Abitec, Excipients for the Pharmaceutical Industry—Regulatory and Product Information, 2013, 2 pages.
Acarturk, Fusun, Mucoadhesive Vaginal Drug Delivery System, Recent Patents on Drug Delivery & Formulation, 2009, vol. 3, pp. 193-195.
Alabi, K. A., et al., Analysis of Fatty Acid Composition of Thevetia peruviana and Hura crepitans Seed oils using GC-FID, Fountain Journal of Nat. and Appl. Sciences, vol. 2(2), pp. 32-37, 2013, Osogbo.
Alexander, KS, Corn Oil, CAS No. 8001-30-7, Jan. 2009.
Alvarez et al., Ectopic uterine tissue as a chronic pain generator, Neuroscience, Dec. 6, 2012, 225: 269-272.
Application Note FT-IR: JI-Ap-FT0508-008, CD spectra of pharmaceuticals substances—Steroids (2), Jasco International Co., Ltd., 2 pages.
Araya-SIB1JA et al., Crystallization of progesterone polymorphs using polymer-induced heteronucleation (PIHn) method, Drug Development and Industrial Pharmacy, Early Online, pp. 1-8, 2014, Informa Healthcare.
Araya-SIB1JA, Andrea M.A., Morphology Study of Progesterone Polymorphs Prepared by Polymer-Induced Heteronucleation (PIHn), Scanning vol. 35 pp. 213-221, 2013, Wiley Period., Inc.
Araya-SIB1JA, Andrea Manela, et al., Chemical Properties of Progesterone Selected Refer., SciFinder, 2014, American Chemical Society & US Natl. Lib. of Med.
Araya-SIB1JA, Andrea Manela, et al., Polymorphism in Progesterone Selected References, SciFinder, Feb. 24, 2014, pp. 1-12, American Chem. Society & Natl. Lib. of Med.
Araya-SIB1JA, Andrea Manela, et al., Polymorphism in Progesterone, SciFinder, pp. 1-46, Feb. 24, 2014, American Chem. Society & Natl. Lib. of Med.

Archer et al., Effects of ospemifene on the female reproductive and urinary tracts: translation from preclinical models into clinical evidence, Menopause: The Journal of the North American Menopause Society, vol. 22, No. 77, pp. 1-11 (2015).
Archer et al., Estrace® vs Premarin® for Treatment of Menopausal Symptoms: Dosage Comparison Study, Advances in Therapy®, vol. 9 No. 1, Jan./Feb. 1992.
Ashburn et al., Cardiovascular, Hepatic and Renal Lesions in Mice Receiving Cortisone, Estrone and Progesterone, Yale J Bilogy and Medicine, vol. 35, Feb. 1963, pp. 329-340.
Azeem, Adnan et al., Microemulsions as a Surrogate Carrier for Dermal Drug Delivery, Drug Development and Industrial Pharmacy, May 2000, vol. 35, No. 5, pp. 525-547 (abstract only). http://informahealthcare.com/doi/abs/10.1080/03639040802448646.
Azure Pharma, Inc., Elestrin™—Estradiol Gel, Drug Info, http://dailymed.nlm.nih.gov/dailymed/archives/fdaDrugInfo.cfm?archiveid=11885, 26 pages, Aug. 2009.
Bakhmutova-Albert, Ekaterina, et al., Enhancing Aqueous Dissolution Rates of Progesterone via Cocrystallization, SSCI, Division of Aptuit, Poster No. R6247, West Lafayette.
Banerjee, Sila, et al., On the Stability of Salivary Progesterone Under Various Conditions of Storage, Steroids, vol. 46(6), pp. 967-974, Dec. 1985.
Barnett, Steven M, Pressure-tuning infared and solution Raman spectroscopic studies of 17B-estradiol and several A-ring . . . , Vibrational Spectroscopy 8, Elsevier, pp. 263, 1995.
Bartosova, Transdermal Drug Delivery In Vitro Using Diffusion Cells, Current Medicinal Chemistry, 2012, 19, 4671-4677, Bentham Science Publishers.
Benbow et al., Distribution and Metabolism of Maternal Progesterone in the Uterus, Placenta, and Fetus during Rat Pregnancy, Biology of Reproduction 52, 1327-1333 (1995).
Bernabei, M.T., et al., Release of progesterone polymorphs from dimethylpolysiloxane polymeric matrixes, Bollettino Chimico Farmaceutico, vol. 122(1) pp. 20-26, 1983 SciFinder.
Bhavnani Bhagu R. et al., "Misconception and Concerns about Bioidentical Hormones Used for Custom-Compounded Hormone Therapy," J Clin Endocrinol Metab, Mar. 2012, 97(3):756-759.
Bhavnani et al., Structure Activity Relationships and Differential Interactions and Functional Activity of Various Equine Estrogens Mediated via Estrogen Receptors (ERs) ERα and ERβ, Endocrinology, Oct. 2008, 149(10):4857-4870.
Bhavnani, B.R., Stanczyk, F.Z., Pharmacology of conjugated equine estrogens: Efficacy, safety and mechanism of action, J. Steroid Biochem. Mol. Biol. (2013), Elsevier.
Bhavnani, B.R., Stanczyk, F.Z., Use of medroxyprogesterone acetate for hormone therapy in postmenopausal women: Is it safe? J. Steroid Biochem. Mol. Biol. (2013), Elsevier.
BioMed Central, Solubility of Progesterone in Organic Solvents, Online PDF, http://www.biomedcentral.com/content/supplementary/1475-2859-11-106-S2.pdf.
Blake et al., Single and multidose pharmacokinetic study of a vaginal micronized progesterone insert (Endometrin) compared with vaginal gel in healthy reproductiveaged female subjects, Fertility and Sterility# vol. 94, No. 4, Sep. 2010, Elsevier.
Borka, Laszlo, Crystal Polymorphism of Pharmaceuticals, Acta Pharm. Jugosl., vol. 40 pp. 71-94, 1990.
Brinton, L.A., Felix, A.S., Menopausal hormone therapy and risk of endometrial cancer, J. Steroid Biochem. Mol. Biol. (2013), Elsevier.
British Pharmacocopoeia 2014 Online, Refined Maize Oil, Ph. Eur. Monograph 1342, vol. I & II, Monographs: Medicinal and Pharmaceutical Substances, http://www.pharmacopoeia.co.uk/bp2014/ixbin/bp.cgi?a=print&id=7400&tab=a-z%20index [Feb. 3, 2014 1:37:50 PM].
Burry, Kenneth A, Percutaneous absorption of progesterone in postmenopausal women treated with transdermal estrogen, Am J Obstet Gynecol, vol. 180(6) part 1, pp. 1504-1511, 1999.
Busetta, Par Bernard, Structure Cristalline et Moleculair de l'Oestradiol Hemihydrate, Acta Cryst., B28 pp. 560, 1972, Bis(dimethyl-o-thiolophenylarsine)palladium(II).

(56) References Cited

OTHER PUBLICATIONS

Busetta, Par Bernard, Structure Cristalline et Moleculaire du Complexe Oestradiol-Propanol, Acta Cryst., B28 pp. 1349, 1972, J.A. Kanters and J. Kroon.

Campsteyn, Par H, et al., Structure Cristalline et Molcculaire de la Progesterone C21H30O2, Acta Cryst., B28 pp. 3032-3042, 1972.

Castelo-Branco Camil et al., "Treatment of atrophic vaaginitis," Therapy, 2007, vol. 4, No. 3, pp. 349-353.

Cendejas-Santana, G, et al., Growth and characterization of progesterone crystallites, Revista Mexicana de Fisica, 50, Suplemento 1 pp. 1-3, 2004.

ChemPro, Top-Notch Technology in Production of Oils and Fats, Chempro-Edible-Oil-Refining-ISO-TUV-Austria.

Cho, Y.A. et al., Transdermal Delivery of Ketorolac Tromethamine: Effects of Vehicles and Penetration Enhancers, Drug Development and Industrial Pharmacy, 30(6):557-564, Jun. 2004.

Christen et al., Phase I/Pharmacokinetic Study of High-Dose Progesterone and Doxorubicin, J Clin Oncol 11:2417-2426, 1993.

Christensson et al., Limonene hydroperoxide analogues differ in allergenic activity, Contact Dermatitis 2008: 59: 344-352.

Christensson et al., Limonene hydroperoxide analogues show specific patch test reactions, Contact Dermatitis, 70, 291-299, 2014.

Christensson et al., Positive patch test reactions to oxidized limonene: exposure and relevance , Contact Dermatitis, 71, 264-272, 2014.

Chun et al., Transdermal Delivery of Estradiol and Norethrindrone Acetate: Effect of Vehicles . . . , J. Kor. Pharm. Sci., vol. 35, No. 3, pp. 173-177 (2005).

Cicinelli et al., Direct Transport of Progesterone From Vagina to Uterus, Obstetrics & Gynecology, vol. 95, No. 3, March 2000, pp. 403-406.

Cicinelli et al., "First uterine pass effect" is observed when estradiol is placed in the upper but not lower third of the vagina, Fertility and Sterility, Vol. 81, No. 5, May 2004, pp. 1414-1416.

Cicinelli, Intravaginal oestrogen and progestin administration: advantages and disadvantages, Best Practices & Research Clinical Obstetrics and Gynaecology vol. 22, No. 2, 2008, pp. 391-405.

Cole, Wayne & Julian, Percy L, Sterols. I. A Study of the 22-Ketosteroids, Cont. of the Research Lab. of the Glidden Co., Soya Prod. Div., vol. 67 pp. 1369-1375, Aug. 1945, Chicago.

Committee Opinion, Incidentally Detected Short Cervical Length, Committee of Obstetric Practice, Obstetrics & Gynecology, ACOG, vol. 119, No. 4, Apr. 2012, pp. 879-882.

Commodari, Fernando, Comparison of 17β-estradiol structures from x-ray diffraction and solution NMR, Magn. Reson. Chem., vol. 43, pp. 444-450, 2005, Wiley InterScience.

Cooper, A, et al., Systemic absorption of progesterone from Progest cream in postmenopausal women, The Lancet, vol. 351, pp. 1255-1256, Research Letters, Apr. 25, 1998.

Corbett et al., "Trends in Pharmacy Compounding for Women's Health in North Carolina: Focus on Vulvodynia," Southern Medical Journal, vol. 107, No. 7, Jul. 2014, pp. 433-436.

Corn Refiners Association, Corn Oil, 5th Edition, Washington, D.C., 2006.

Crandall, Carolyn, "Vaginal Estrogen Preparations: A Review of Safety and Efficacy for Vaginal Atrophy," Journal of Women's Health, 2002, vol. 11, No. 10, pp. 857-877.

Cremer Care, ""Miglyol® 810, 812 INCI: Caprylic/Capric Triglyceride,"" Cremer Oleo GmbH & Co. KG, pp. 1-7, available at http://s3.amazonaws.com/petercremerna/products/spec_sheets/159/339/301 /originai/M IGL YOL_81 0_812_ TDS.pdf?1389204445 (Mar. 2013) accessed on Dec. 30, 2016.

Critchley et al., Estrogen Receptor β, But Not Estrogen Receptor α, Is Present in the Vascular Endothelium of the Human and Nonhuman Primate Endometrium, The Journal of Clinical Endocrinology & Metabolism, 2001, vol. 86, No. 3, pp. 1370-1378.

Dauqan, Eqbal M. A., et al., Fatty Acids Composition of Four Different Vegetable Oils (Red Palm Olein, Palm Olem, Corn Oil, IPCBEE, vol. 14, 2011, IACSIT Press, Singapore.

Dideberg, O, et al., Crystal data on progesterone (C21H30O2), desoxycorticosterone (C21H30O3), corticosterone (C21H30O4) and aldosterone . . . , J. Appl. Cryst. vol. 4 pp. 80, 1971.

Diramio, Jackie A., Polyethylene Glycol Methacrylate/ Dimetacrylate Hydrogels for Controlled Release of Hydrophobic Drugs, Masters of Science Thesis, University of Georgia, Athens, Georgia, 2002, 131 pages.

Drakulic, Branko J, Role of complexes formation between drugs and penetration enhancers in transdermal . . . , Inter. Journal of Pharmaceutics, Elsevier, vol. 363, pp. 40-49, 2009.

Du et al., Percutaneous progesterone delivery via cream or gel application in postmenopausal women: a randomized cross-over study of progesterone levels in serum, whole blood, saliva, and capillary blood, Menopause: The Journal of the North American Menopause Society, 2013, vol. 20, No. 11, pp. 1-7.

Duax, William L, et al., Conformation of Progesterone Side Chain: Conflict between X-ray Data and Force-Field Calculations, J. Am. Chem. Soc., vol. 103 pp. 6705-6712, Jun. 1981.

Duclos, R, et al., Polymorphism of Progesterone: Influence of the carrier and of the solid dispersion manufacturing . . . , J. Thermal Anal., vol. 37 pp. 1869-1875, 1991, Wiley.

Ebian, A.R., Ebian Article: Polymorphism and solvation of ethinyl estradiol, SciFinder, Pharmaceutica Acta Helvetiae, vol. 54(4), pp. 111-114, 1979, Alexandria, Egypt.

Eisenberger, A., Westhoff, C., Hormone replacement therapy and venous thromboembolism, J. Steroid Biochem. Mol. Biol. (2013), Elsevier.

Engelhardt et al., Conceptus Influences the Distribution of Uterine Leukocytes During Early Porcine Pregnancy, Biology of Reproduction 66, 1875-1880 (2002).

Estradiol, The Merck Index Online, Royal Society of Chemistry, https://www.rsc.org/Merck-Index/monograph/mono1500003758/estradiol?q=unauthorize.

Ettinger et al., Comparison of endometrial growth produced by unopposed conjugated estrogens or by micronized estradiol in postmenopausal women, Am J Obstet Gynecol 1997; 176:112-117.

Excipients for Pharmaceuticals, Sasol Olefins & Surfactants GMBH, 2010, 28 pages.

Faassen, Fried, Physicochemical Properties and Transport of Steroids across Caco-2 Cells, Pharmaceutical Research, vol. 20(2), 2003, Plenum Pub. Corp.

FDA, Draft Guidance on Progesterone, Recommended Apr. 2010, Revised Feb. 2011 http://www.fda.gov/downloads/Drugs/GuidanceComplianceRegulatoryInformation/Guidances/UCM209294.pdf.

Ferrari, Roseli AP., et al., Oxidative Stability of Biodiesel From Soybean Oil Fatty Acid Ethyl Esters, Sci. Agric., vol. 62(3), pp. 291-295, 2005, PiracicaB1, Braz.

Filipsson et al., Concise International Chemical Assessment Document 5: Limonene, first draft, World Health Organization, Geneva, 1998, 36 pages.

Final Report on the Safety Assessment of BHT, International Journal of Toxicology, 21(Suppl. 2):19-94, 2002/.

Flyvholm, Sensitizing risk of butylated hydroxytoluene B1sed on exposure and effect data, Contact Dermatitis 1990: 23: 341-345.

Fotherby, K., Bioavailability of Orally Administered Sex Steroids Used in Oral Contraception and Hormone Replacement Therapy, Contraception, 1996; 54:59-69.

Franklin et al., Characterization of immunoglobulins and cytokines in human cervical mucus: influence of exogenous and endogenous hormones, Journal of Reproductive Immunology 42 (1999) 93-106, Elsevier.

Franz et al., Use of Excised Human Skin to Assess the Bioequivalence of Topical Products, Skin Pharmacol Physiol 2009;22:276-286.

Freedman, R.R., Menopausal hot flashes: Mechanisms, endocrinology, treatment, J. Steroid Biochem. Mol. Biol.(2013), Elsevier.

Fuchs et al., The Effects of an Estrogen and Glycolic Acid Cream on the Facial Skin of Postmenopausal Women: A Randomized Histologic Study, Cutis. Jun. 2003;71(6):481-8.

Fugh-Berman, Adriane, Bioidentical Hormones for Menopausal Hormone Therapy: Variation on a Theme, Journal of General Internal Medicine, vol. 22, pp. 1030-1034, 2007.

(56) References Cited

OTHER PUBLICATIONS

Furness et al., Hormone therapy in postmenopausal women and risk of endometrial hyperplasia (Review), 2012, pp. 1-204, The Cochrane Collaboration. Published by JohnWiley & Sons, Ltd.
Gäfvert et al., Free radicals in antigen formation: reduction of contact allergic response to hydroperoxides by epidermal treatment with antioxidants, British Journal of Dermatology 2002; 146: 649-656.
Ganam-Quintanar et al., Evaluation of the transepidermal permeation of diethylene glycol monoethyl ether and skin water loss, International Journal of Pharmaceutics, vo. 147, No. 2, Feb. 28, 1997, pp. 165-171 (abstract only).
Garad S. et al., "Preclinical Development for Suspensions," A.K. Kulshreshtha et al. (eds.), *Pharmaceutical Suspensions: From Formulation Development to Manufacturing*, Springer, New York 2010, pp. 127-176.
Gattefossé SAS, Material Safety Data Sheet, Gelot 64, 2012, 8 pages.
Gattefossé SAS, Regulatory Data Sheet, Gelot 64, 2012, 6 pages.
Gattefossé SAS, Regulatory Data Sheet, Lauroglycol 90, 2012, 5 pages.
Gattefossé, "Excipients for Safe and Effective Topical Delivery, Drug Development and Delivery" Jul./Aug. 2012, http://drug-dev.com/Main/B1ck-Issues/Transdermal-Topical-Subcutaneous-NonInvasive-Deliv-5.aspx#.
Geelen, Math J.H. et al., "Dietary medium-chain fatty acids raise and (n-3) polyunsaturated fatty acids lower hepatic triacylglycerol synthesis in rats," The Journal of Nutrition, 1995, 125(10):2449-2456.
Gillet et al., Induction of amenorrhea during hormone replacement therapy: optimal micronized progesterone dose. A multicenter study, Maturitas 19 (1994) 103-115.
Giron-Forest, D, et al., Thermal analyis methods for pharmacopoeial materials, J. Pharmaceutical & Biomedical Anal., vol. 7(12) pp. 1421-1433, 1989, Pergamon Press, Gr. Britain.
Giron-Forest, D, Thermal analysis and calorimetric methods in the characterisation of polymorphs and solvates, Thermochimica Acta, vol. 248 pp. 1-59, 1995, Elsevier.
Glaser et al, Pilot Study: Absorption and Efficacy of Multiple Hormones Delivered in a Single Cream Applied to the Mucous Membranes of the Labia and Vagina, Gynecol Obstet Invest 2008;66:111-118.
Golatowski et al., Comparative evaluation of saliva collection methods for proteome analysis, Clinica Chimica Acta 419 (2013) 42-46.
Graham et al, Physiological Action of Progesterone in Target Tissues, Endocrine Reviews, 1997, vol. 18, No. 4, pp. 502-519.
Groothuis et al., Estrogen and the endometrium: lessons learned from gene expression profiling in rodents and human, Human Reproduction Update, vol. 13, No. 4 pp. 405-417, 2007.
Gunstone, Frank D, et al., Vegetable Oils in Food Technology: Composition, Properties and Uses, Blackwell Publishing, CRC Press, 2002.
Gurney, E.P. et al., The Women's Health Initiative trial and related studies: 10 years later: A clinician's view, J. Steroid Biochem. Mol. Biol. (2013), Elsevier.
Hamid et al., The effects of common solubilizing agents on the intestinal membrane B1rrier functions and membrane toxicity in rats, International Journal of Pharmaceutics 379 (2009) 100-108, Elsevier.
Haner, Barbara, Crystal data (I) for some pregnenes and pregnadienes, Acta Cryst., vol. 17 pp. 1610, 1964.
Hapgood, J.P., et al., Potency of progestogens used in hormonal therapy: Toward understanding differential actions, J. Steroid Biochem. Mol. Biol. (2013), Elsevier.
Hargrove et al., Menopausal Hormone Replacement Therapy with Continuous Daily Oral Micronize Estradiol and Progesterone, Obstet Gynecol, vol. 73, No. 4, Apr. 1989, pp. 606-612.
Hatton et al., "Safety and efficacy of a lipid emulsion containing medium-chain triglycerides," Clinical Pharmacy, 1990, vol. 9, No. 5, pp. 366-371.
He et al., Apoptotic Signaling Pathways in Uteri of Rats with Endometrial Hyperplasia Induced by Ovariectomy Combined with Estrogen, Gynecol Obstet Invest 2013;76:51-56.
Helbling, Ignacio M, et al., The Optimization of an Intravaginal Ring Releasing Progesterone Using a Mathematical Model, Pharm Res, vol. 31 pp. 795-808, 2014, Springer Science.
Helmy et al., Estrogenic Effect of Soy Phytoestrogens on the Uterus of Ovariectomized Female Rats, Clinic Pharmacol Biopharmaceut, 2014, S2, 7 pages.
Henderson, V.W., Alzheimer's disease: Review of hormone therapy trials and implications for treatment and prevention after . . . , J. Steroid Biochem. Mol. Biol. (2013), Elsevier.
Henriksen, Thormod, et al., An ENDOR Sturdy of Radiation-Induced Molecular Damage to Progesterone, Jour. of Mag. Resonance, vol. 63, pp. 333-342, 1985, Acedemic Press, Inc.
Herman, Anna et al., "Essential oils and their constituents as skin penetration enhancer for transdermal drug delivery: a review," 2014 Royal Pharmaceutical Society, Journal of Pharmacy and Pharmacology, pp. 1-13.
Hodis, H.N., Mack, W.J., Hormone replacement therapy and the association with heart disease and overall mortality: Clinical . . . , J. Steroid Biochem. Mol. Biol. (2013), Elsevier.
Holm et al., "Examination of oral absorption and lymphatic transport of halofantrine in a triple-cannulated canine model after administration in self-microemulsifying drug delivery systems (SMEDDS) containing structured triglycerides," European Journal of Pharmaceutical Sciences 20 (2003) 91-97.
Hospital, Michel, et al., X-ray Crystallography of Estrogens and Their Binding to Receptor Sites, Mol. Pharmacology, vol. 8 pp. 438-445, Acedemic Press, Inc., 1972.
Hostynek, JJ, Predictinga bsorptiono f fragrancec hemicalst hrough human skin, j. Soc.C osmeCt. hem.,4 6, 221-229 (Jul./Aug. 1, 1995).
Hulsmann, Stefan, Stability of Extruded 17B-Estradiol Solid Dispersions, Pharmaceutical Development and Tech., vol. 6(2) pp. 223-229, 2001, Marcel Dekker, Inc.
Humberstone, Andrew et al., "Lipid-based vehicles for the oral delivery of poorly water soluble drugs," Advanced Drug Delivery Reviews, 25 (1997) 103-128.
Hurn et al., Estrogen as a Neuroprotectant in Stroke, Journal of Cerebral Blood Flow and Metabolism 20:631-652, 2000, Lippincott Williams & Wilkins, Inc., Philadelphia.
Hyder et al., Synthetic Estrogen 17α-Ethinyl Estradiol Induces Pattern of Uterine Gene Expression Similar to Endogenous Estrogen 17β-Estradiol, JPET 290(2):740-747, 1999.
Idder, Salima, et al., Physicochemical properties of Progesterone, SciFinder, pp. 1-26, Feb. 24, 2014, American Chem. Society & US Natl. Lib. of Med.
Johanson, Gunnar, Toxicity Review of Ethylene Glycol Monomethyl Ether and its Acetate Ester, Critical Reviews in Toxicology, 2000, vol. 30, No. 3 , pp. 307-345 (abstract only). http://informahealthcare.com/doi/abs/10.1080/10408440091159220.
Johnson, William S, et al., Racemic Progesterone, Tetrahedron Letters No. 4, pp. 193-196, 1963, Pergamon Press Ltd., Great Britain.
Joshi et al., Detection and synthesis of a progestagen-dependent protein in human endometrium, J Reprod Fert (1980) 59, 273-285.
Kanno et al., The OECD Program to Validate the Rat Uterotrophic Bioassay to Screen Compounds for in Vivo Estrogenic Responses: Phase 1, Environmental Health Perspectives • vol. 109 | No. 8 | Aug. 2001, pp. 785-794.
Karande, et al. Enhancement of transdermal drug delivery via synergistic action of chemicals, Biochimica et Biophysica Acta, 1788:2362-2373, Sep. 2009.
Karlberg et al., Air oxidation of d-limonene (the citrus solvent) creates potent allergens, Contact Dermatitis, 1992: 26: 332-340.
Karlberg et al., Influence of an anti-oxidant on the formation of allergic compounds during auto-oxication of d-limonene, Ann. Occup. Hyg., vol. 38, No. 2, pp. 199-207, 1994.

(56) References Cited

OTHER PUBLICATIONS

Kaunitz, Andrew M., Extended duration use of menopausal hormone therapy, Menopause: The Journal of the North American Menopause Society, 2014, vol. 21, No. 6, pp. 1-3.
Khalil, Sah, Stability and Dissolution Rates of Corticosteroids in Polyethylene Glycol Solid Dispersions, Drug Dev. & Indus. Pharm., vol. 10(5) pp. 771-787, 1984, Marcel Dekker.
Kharode et al., The Pairing of a Selective Estrogen Receptor Modulator, B 1zedoxifene, with Conjugated Estrogens as a New Paradigm for the Treatment of Menopausal Symptoms and Osteoporosis Prevention, Endocrinology 149(12):6084-6091, 2008.
Kim et al., Safety Evaluation and Risk Assessment of d-Limonene, Journal of Toxicology and Environmental Health, Part B: Critical Reviews, 2013, 16:1, 17-38 http://dx.doi.org/10.1080/10937404.2013.769418.
Kincl et al., Increasing Oral Bioavailability of Progesterone by Formulation, Journal of Steroid Biochemistry, 1978, vol. 9, pp. 83-84.
Knuth et al., Hydrogel delivery systems for vaginal and oral applications: Formulation and biological considerations, Advanced Drug Delivery Reviews, vol. 11, No. 1-2, Jul.-Aug. 1993, pp. 137-167.
Koga et al., Enhancing mechanism of Labrasol on intestinal membrane permeability of the hydrophilic drug gentamicin sulfate, European Journal of Pharmaceutics and Biopharmaceutics 64 (2006) 82-91.
Komm et al., B 1zedoxifene Acetate: A Selective Estrogen Receptor Modulator with Improved Selectivity, Endocrinology 146(9):3999-4008, 2005.
Korkmaz, Filiz, Byophysical Studies of Progesterone-Model Membrane Interactions, Thesis, Grad. School of Nat. and App. Sci. of The Middle East Tech. University, Sep. 2003.
Kotiyan, P.N. Stability indicating HPTLC method for the estimation of estradiol, Journal of Pharmaceutical and Biomedical Analysis, vol. 22 pp. 667-671, 2000, Elsevier.
Krzyminiewski, R, et al., EPR Study of the Stable Radical in a y-Irradiated Single Crystal of Progesterone, Jour. of Mag. Resonance, vol. 46 pp. 300-305, 1982, Acedemic Press.
Kubli-Garfias, C, et al., Ab initio calculations of the electronic structure of glucocorticoids, Jour. of Mol. Structure, Theochem, vol. 454 pp. 267-275, 1998, Elsevier.
Kubli-Garfias, Carlos, Ab initio study of the electronic structure of progesterone and related progestins, Jour. of Mol. Structure, Theochem vol. 425, pp. 171-179, 1998, Elsevier (abstract only).
Kuhnert-Brandstaetter and Grimm. Zur Unterscheidung von losungsmittelhaltigen pseudopolymorphen Kristallformen und polymorphen Modifikationen bei Steroidhormonen.II, Mikrochimica Acta, vol. 1, pp. 127-139, 1968.
Kuhnert-Brandstaetter and Junger and Kofler. Thermo-microscopic and spectrophotometric: Determination of steroid hormones, Microchemical Journal 9, pp. 105-133, 1965.
Kuhnert-Brandstaetter and Kofler. Zur mikroskopischen Identitatsprufung und zur Polymorphie der Sexualhormone, Mikrochimica Acta, vol. 6, pp. 847-853, 1959.
Kuhnert-Brandstaetter and Linder. Zur Hydratbildung bei Steroidhormonen, Sci. Pharm, vol. 41(2), pp. 109-116, 1973.
Kumasaka et al., Effects of Various Forms of Progestin on the the Estrogen-Primed, Ovariectomized Rat, Endocrine Journal 1994, 41(2), 161-169.
Kuon et al., A Novel Optical Method to Assess Cervical Changes during Pregnancy and Use to Evaluate the Effects of Progestins on Term and Preterm Labor, Am J Obstet Gynecol. Jul. 2011 ; 205(1): 82.e15-82.e20.
Kuon et al., Actions of progestins for the inhibition of cervical ripening and uterine contractions to prevent preterm birth, FVV in OBGYN, 2012, 4 (2): 110-119.
Kuon et al., Pharmacological actions of progestins to inhibit cervical ripening and prevent delivery depend upon their properties, the route of administration and the vehicle, Am J Obstet Gynecol. May 2010 ; 202(5): 455.e1-455.e9.

Labrie, et al., Intravaginal prasterone (DHEA) provides local action without clinically significant changes in serum concentrations of estrogens or androgens, Journal of Steroid Biochemistry & Molecular Biology, vol. 138, pp. 359-367, 2013, Elsevier.
Lacey, J.V. Jr., The WHI ten year's later: An epidemiologist's view, J. Steroid Biochem. Mol. Biol. (2013), Elsevier.
Lahiani-Skiba, Malika, Solubility and Dissolution Rate of Progesterone-Cyclodextrin . . . , Drug Development and Industrial Pharmacy, Informa Healthcare vol. 32, pp. 1043-1058, 2006.
Lancaster, Robert W, et al., The Polymorphism of Progesterone: Stabilization of a 'Disappearing' Polymorph by . . . , Jour. of Pharm. Sci., vol. 96(12) pp. 3419-3431, 2007, Wiley-Liss.
Land, Laura M, The influence of water content of triglyceride oils on the solubility of steriods, Pharmaceutical Research, vol. 22(5) May 2005, Springer Science+Business Media.
Lane, Majella E., "Skin penetration enhancers," International Journal of Pharmaceutics 447 (2013) 12-21.
Lauer et al., "Evaluation of the hairless rat as a model for in vivo percutaneous absorption," Journal of Pharmaceutical Sciences, vol. 86, No. 1, Jan. 1997, pp. 13-18.
Leonetti et al., Transdermal progesterone cream as an alternative progestin in hormone therapy, Alternative Therapies, Nov./Dec. 2005, vol. 11, No. 6, pp. 36-38.
Leonetti, Helene B, et al., Topical progesterone cream has an antiproliferative effect on estrogen-stimulated endometrium, Fertility and Sterility, vol. 79(1), Jan. 2003.
Lewis, John G. et al., Caution on the use of saliva measurements to monitor absorption of progesterone from transdermal creams in postmenopausal women, Maturitas, The European Menopause Journal, vol. 41, pp. 1-6, 2002.
Li, Guo-Chian, Solid-state NMR analysis of steroidal conformation of 17a- and 17B-estradiol in the absence and presence of lipi . . . , Steroids, Elsevier, vol. 77, pp. 185-192, 2012.
Lindmark, Tuulikki et al., "Absorption Enhancement through Intracellular Regulation of Tight Junction Permeability by Medium Chain Fatty Acids in Caco-2 Cells," JPET 284(1):362-369, 1998.
Lindmark, Tuulikki et al., "Mechanisms of Absorption Enhancement by Medium Chain Fatty Acids in Intestinal Epithelial Caco-2 Cell Monolayers," JPET 275(2):958-964, 1995.
Lobo, R.A., Foreword, J. Steroid Biochem. Mol. Biol. (2014), Elsevier.
Lopes, Luciana B. et al., Enhancement of transdermal delivery of progesterone using medium-chain mono and diglycerides as skin penetration enhancers, Pharmaceutical Development and Technology, 14:5, 524-529, Mar. 2009.
López-Belmonte, Corrigendum to "Comparative uterine effects on ovariectomized rats after repeated treatment with different vaginal estrogen formulations" [Maturitas 72 (2012) 353-358], Maturitas 74 (2013) 393, Elsevier.
Lucy et al., Gonadotropin-releasing hormone at estrus: lutenizing hormone, estradiol, and progesterone during . . . Biol Reprod Sep. 1986;35(2):300-311 (abstract only).
Lvova, M. SH., et al., Thermal Analysis in the Quality Control and Standardization of Some Drugs, J Thermal Anal., vol. 40 pp. 405-411, 1993, Wiley.
Mac Bride, Maire B. et al., "Vulvovaginal Atrophy," Mayo Clin Proc, Jan. 2010, 85(1):87-94.
Madishetti et al., Development of domperidone bilayered matrix type transdermal patches: physicochemical, in vitro and ex vivo characterization, DARU vol. 18, No. 3, 2010, pp. 221-229.
Magness, R.R., et al., Estrone, Estradiol-17β and Progesterone Concentrations in Uterine Lymph and Systematic Blood throughout the Porcine Estrone Estrous Cycle, Journal of Animal Science, vol. 57, pp. 449-455, ISU, 1983.
Manson, JoAnn E. et al., "Menopausal hormone therapy and health outcomes during the intervention and extended poststoping phases of the women's health initiative randomized trials," JAMA, Oct. 2, 2013, vol. 310, No. 13, pp. 1353-1368.
Martelli, Mary Elizabeth, "Vaginal Medicine Administration," The Gale Encyclopedia of Nursing and Allied Health, Gale Group, 2002, pp. 2542-2543.

(56) References Cited

OTHER PUBLICATIONS

Mcguffy, Irena, Softgel Technology as a Lipid-Blsed Delivery Tool for Bioavailability Enhancement, Catalent Pharma Solutions, Somerset, NJ, Mar. 2011.
Mesley, R.J., Clathrate Formation from Steroids, Chemistry and Industry, vol. 37 pp. 1594-1595, Sep. 1965.
Miao, Wenbin, et al., Chemical Properties of Progesterone, SciFinder, 2014, American Chemical Society & US Natl. Lib. of Med.
Miles et al., Pharmacokinetics and endometrial tissue levels of progesterone after administration bv'Intramuscular and vaginal routes: a comparative study, Fertility and Sterility, vol. 62, No. 3, Sep. 1994, pp. 485-490.
Miller et al., Safety and Feasibility of Topical Application of Limonene as a Massage Oil to the Breast, Journal of Cancer Therapy, 2012, 3, 749-754.
Monti, D. et al., Effect of different terpene-containing essential oils on permeation of estradiol through hairless mouse skin, International Journal of Pharmaceutics, 237:209-24, 2002.
Mueck, A.O. et al., Genomic and non-genomic actions of progestogens in the breast, J. Steroid Biochem. Mol.Biol. (2013), Elsevier.
Muramatsu, Mitsuo, Thermodynamic Relationship between a- and B-Forms of Crystalline Progesterone, J. Pharmaceutical Sciences, vol. 68(2) pp. 175-178, 1979, Amer. Pharm. Assoc.
Ng, Jo-Han et al., Advances in biodiesel fuel for application in compression ignition engines, Clean Techn Environ Policy, vol. 12, pp. 459-493, 2010, Springer-Verlag.
Nicklas, Martina, Preparation and characterization of marine sponge collagen nanoparticles and employment for the trans . . . , Drug Devel. & Indust. Pharmacy,35(9) pp. 1035, 2009.
Nilsson et al., Analysis of Contact Allergenic Compounds in Oxidized d-Limonene, Chromatographia vol. 42, No. 3/4, Feb. 1996, pp. 199-205.
Notelovitz, Morris, et al., Initial 17-b-Estradiol Dose for Treating Vasomotor Symptoms, Obstetrics & Gynecology, vol. 95(5), pp. 726-731, part 1, May 2000, Elsevier.
NuGen, What is NuGen HP Hair Growth System.
NuGest900, NuGest 900™.
O'Leary, Peter, Salivary, but not serum or urinary levels of progesterone are elevated after topical application of pregersterone cream to pre-and post-menopausal women, Clinical Endocrinology, vol. 53 pp. 615-620, Blackwell Science 2000.
Opinion on the Diethylene Glycol Momoethyl Ether (DEGEE), Scientific Committee on Consumer Products, Dec. 19, 2006, 27 pages.
Outterson, K., The Drug Quality and Security Act—Mind the Gaps, n engl j med 370;2 nejm.org Jan. 9, 2014, pp. 97-99.
Pachman et al., "Management of menopause-associated vasomotor symptoms: current treatment options, challenges and future directions," International Journal of Women's Health, May 7, 2010.
Palamakula et al., Preparation and In Vitro Characterization of Self-Nanoemulsified Drug Delivery Systems of Coenzyme Q10 Using Chiral Essential Oil Components, Pharmaceutical Technology Oct. 2004, pp. 74-88.
Panay et al., The 2013 British Menopause Society & Women's Health Concern recommendations on hormone replacement therapy, Menopause International: The Integrated Journal of Postreproductive Health, published online May 23, 2013, Sage Publications. http://min.sagepub.com/content/early/2013/05/23/1754045313489645. 1.
Panchangnula et al., Development and evaluation of an intracutaneous depot formulation of corticosteroids using Transcutol . . . , J Pharm Pharmacol. Sep. 1991;43(9):609-614 (abstract only).
Parasuraman et al., Blood sample collection in small laboratory animals, Journal of Pharmacology & Pharmacotherapeutics | Jul.-Dec. 2010 | vol. 1 | Issue 2, pp. 87-93.
Park, Jeong-Sook, Solvent effects on physicochemical behavior of estradiols recrystalized for transdermal delivery, Arch Pharm Res, vol. 31(1), pp. 111-116, 2008.
Park, Jeong-Sook, Use of CP/MAS solid-state NMR for the characterization of solvate . . . , European Journal of Pharmaceutics and Biopharmaceutics, vol. 60, pp. 407-412, 2005.
Parrish, Damon A., A new estra-1,3,5(10)-triene-3,17b-diol solvate: estradiol-methanol-water, Crystal Structure Comm., Intn'l Union of Crystallography, ISSN 0108-2701, 2003.
Patel et al., Transdermal Drug Delivery System: A Review, www.thepharmajournal.com, vol. 1, No. 4, 2012, pp. 78-87.
Payne, R.S., et al., Examples of successful crystal structure prediction: polymorphs of primidone and progesterone, Intl. Jour. of Pharma., vol. 177 pp. 231-245, 1999, Elsevier.
PCCA, Apothogram, PCCA, May 2014, Houston, TX.
Persson, Linda C, et al., Physicochemical Properties of Progesterone Selecte, SciFinder, pp. 1-5, Feb. 24, 2014, American Chem. Society & US Natl. Lib. of Med.
Pfaus et al., Selective facilitation of sexual solicitation in the female rat by a melanocortin receptor agonist, PNAS, Jul. 6, 2004, vol. 101, No. 27, pp. 10201-10204.
Pheasant, Richard, Polymorphism of 17-Ethinylestradiol, Schering Corporation, Bloomfield, NJ, May 1950.
Pickles, VR, Cutaneous reactions to injection of progesterone solutions into the skin, Br Med Journal, Aug. 16, 1952, pp. 373-374.
Pinkerton et al., What are the concerns about custom-compounded "bioidentical" hormone therapy? Menopause: The Journal of the North American Menopause Society, vol. 21, No. 12, 2014,pp. 1-3.
Pinkerton, J.V., Thomas, S., Use of SERMs for treatment in postmenopausal women, J. Steroid Biochem. Mol. Biol. (2014), Elsevier.
Pisegna, Gisia L, A High-pressure Vibrational Spectroscopic Study of Polymorphism in Steroids . . . , Thesis, McGill University, Dept. of Chem, Nov. 1999, Natl. Lib. of Canada.
Portman, David et al., One-year treatment persistence with local estrogen therapy in postmenopausal women diagnosed as having vaginal atrophy, Menopause, vol. 22, No. 11, 2015, pp. 000/000 (8 pages).
Position Statement, Management of symptomatic vulvovaginal atrophy: 2013 position statement of the North American Menopause Society (NAMS), Menopause, vol. 20, No. 9, pp. 888-902.
Potluri, Praveen and Gum V. Betageri, "Mixed-micellar proliposomal systems for enhanced oral delivery of progesterone," Drug Delivery, 2006, vol. 13, No. 3, pp. 227-232.
Practice Bulletin No. 141, Management of Menopausal Symptoms, Obstetrics & Gynecology, ACOG, vol. 123, No. 1, Jan. 2014, pp. 202-216.
Prajapati Hetal N. et al., "A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development," Pharm Res. Jan. 2012; 29(1): 285-305. Published online Aug. 23, 2011. doi: 10.1007/s11095-011-0541-3.
Prajapati Hetal N. et al., "Effect of Difference in Fatty Acid Chain Lengths of Medium-Chain Lipids on Lipid/Surfactant/Water Phase Diagrams and Drug Solubility," J. Excipients and Food Chem. 2 (3) 2011:73-88.
Prajapati, Hetal N, et al., A comparative Evaluation of Mono-, Di- and Triglyceride of Medium Chain Fatty Acids by Lipid/Surfactant/Water, Springerlink.com, pp. 1-21, Apr. 2011.
Prausnitz et al., Transdermal drug delivery, Nat Biotechnol. Nov. 2008 ; 26(11): 1261-1268.
Price, Sarah L, The computational prediction of pharmaceutical crystal structures and polymorphism, Adv. Drug Delivery Reviews, vol. 56 pp. 301-319, 2004, Elsevier.
Product Information Sheet, Body Bllance Cream, Tahitian Noni International, 2013, 1 page.
Product Safety Assessment: Diethylene Glycol Monoethyl Ether, Created: Sep. 24, 2007 The Dow Chemical Company Page, 5 pages.
Progesterone, The Merck Index Online, Royal Society of Chemistry, 2013, search Feb. 17, 2014 https://www.rsc.org/Merck-Index/monograph/print/mono1500007889/progesterone?q=authorize.
Progynova TS 100, available online at file :///C:/Users/Call%20Family/Desktop/Progynova%20TS%20100%2012%20Patches_Pack%20%28Estradiol%20Hemihydrate%29.html, 2010.
Provider Data Sheet, About Dried Blood Spot Testing, ZRT Laboratory, 2014, 3 pages.

(56) References Cited

OTHER PUBLICATIONS

Rahn et al., Vaginal Estrogen for Genitourinary Syndrome of Menopause A Systematic Review, Obstet Gynecol 2014;124(6):1147-56.
Rao, Rajeswara et al., "Intra Subject Variability of Progesterone 200 mg Soft Capsules in Indian Healthy Adult Postmenopausal Female Subjects under Fasting Conditions," J Bioequiv Availab. 2014, 6: 139-143.
Rao, R. et al., "The Affect of Capmul, Labrafil and Transcutol on Progesterone 100 Mg Soft Capsules Bioavailability in Indian Healthy Adult Postmenopausal Female Subjects Under Fasting Conditions," Bioequivalence & Bioavailability, 7(2):095-107, 2015.
Regidor, P., "Progesterone in Peri- and Postmenopause: A Review," Geburtshilfe Frauenheilkd, Nov. 2014 74(11):995-1002.
Reisman et al., Topical Application of the Synthetic Triterpenoid RTA 408 Protects Mice from Radiation-Induced Dermatitis, Radiation Research 181, 512-520 (2014).
Rosilio, V, et al., Physical Aging of Progesterone-Loaded Poly(D,L,-lactide-co-glycolide) Microspheres, Pharmaceutical Research, vol. 15(5) pp. 794-799,1998, Plenum Pub. Corp.
Ross et al., Randomized, double-blind, dose-ranging study of the endometrial effects of a vaginal progesterone gel in estrogen-treated postmenopausal women, AnnJ Obstet Gynecol, Oct. 1997, vol. 177, No. 4, pp. 937-941.
Ruan et al., Systemic progesterone therapy—Oral, vaginal, injections and even transdermal? Maturitas 79 (2014) 248-255, Elsevier.
Salem, HF, Sustained-release progesterone nanosuspension following intramuscular injection in ovariectomized rats, International Journal of Nanomedicine 2010:5 943-954, Dove Press.
Sallee, Verney L. et al., "Determinants of intestinal mucosal uptake of short- and medium-chain fatty acids and alcohols," Journal of Lipid Research, 1973, vol. 14, 475-484.
Salole, Eugene G., Estradiol, Analytical Profiles of Drug Substances, vol. 15, pp. 283-318, 1986.
Salole, Eugene G., The physicochemical properties of oestradiol, Journal of Pharmaceutical & Biomedical Analysis, vol. 5, No. 7, pp. 635-648, 1987.
Santen, R.J., Menopausal hormone therapy and breast cancer, J. Steroid Biochem. Mol. Biol. (2013), Elsevier.
Santen, RJ, Vaginal administration of estradiol: effects of dose, preparation and timing on plasma estradiol levels, Climacteric 2014;17:1-14.
Sarkar, B1SU, et al., Chemical Stability of Progesterone in Compounded Topical Preparations using PLO Transdermal Cream™ and HRT Cream™ B1se . . . , J Steroids Horm Sci, 4:2, 2013.
Sarpal, K. et al., "Self emulsifying drug delivery systems: a strategy to improve oral bioavailability," Current Research & Information on Pharmaceuticals Sciences (CRIPS), 2010, vol. 11, No. 3, pp. 42-49.
Sarrel, et al., The Mortality Toll of Estrogen Avoidance: An Analysis of Excess Deaths Among Hysterectomized Women Aged 50 to 59 Years, American Journal of Public Health, Research and Practice, e1-e6. Published online ahead of print Jul. 18, 2013.
Satyanarayana, D, et al., Aqueous Solubility Predictions of Aliphatic Alcohols, Alkyl Substituted Benzoates and Steroids, Asian J. Chem., vol. 9 (3) pp. 418-426, 1997.
Scavarelli, Rosa Maria, et al., Progesterone and Hydrate or Solvate, SciFinder, pp. 1-2, Feb. 24, 2014, American Chem. Society.
Schindler, A.E., The "newer" progestogens and postmenopausal hormone therapy (HRT), J. Steroid Biochem.Mol. Biol. (2013), Elsevier.
Schindler, Aldof E. et al., Classification and pharmacology of progestins, Maturitas 46S1 (2003) S7-S16.
Schutte et al., A tissue engineered human endometrial stroma that responds to cues for secretory differentiation, decidualization and menstruation, Fertil Steril. Apr. 2012 ; 97(4): 997-1003, Elsevier.
Schweikart et al., Comparative Uterotrophic Effects of Endoxifen and Tamoxifen in Ovariectomized Sprague-Dawley Rats, Toxicologic Pathology, 42: 1188-1196, 2014.
SciFinder Scholar Prednisone Chemical Properties, SciFinder, 2014, pp. 1-7, National Library of Medicine.
SciFinder Scholar Prednisone Physical Properties, SciFinder, 2014, pp. 1-10, Natioinal Library of Medicine.
SciFinder Scholar Progesterone Experimental Properties, SciFinder, pp. 1-9, Feb. 24, 2014, American Chem. Society.
Search Report, Extended European Search Report for EP13741053.6, dated Jul. 1, 2015.
Search Report, Extended European Search Report for EP13807188.1, dated Nov. 23, 2015.
Search Report, International Search Report and Written Opinion for PCT/US12/66406, dated Jan. 24, 2013.
Search Report, International Search Report and Written Opinion for PCT/US13/23309, dated Apr. 9, 2013.
Search Report, International Search Report and Written Opinion for PCT/US13/46442, dated Nov. 1, 2013.
Search Report, International Search Report and Written Opinion for PCT/US13/46443, dated Oct. 31, 2013.
Search Report, International Search Report and Written Opinion for PCT/US13/46444, dated Oct. 31, 2013.
Search Report, International Search Report and Written Opinion for PCT/US13/46445, dated Nov. 1, 2013.
Search Report, International Search Report and Written Opinion for PCT/US14/61811, dated Jan. 21, 2015.
Search Report, International Search Report and Written Opinion for PCT/US15/23041, dated Jun. 30, 2015.
Search Report, International Search Report and Written Opinion for PCT/US15/42621, dated Oct. 29, 2015.
Serantoni, Foresti, et al., 4-Pregnen-3,20-dione (progesterone, form II), Crystal Structure Comm., vol. 4(1) pp. 189-192, 1975, CAPLUS Database.
Shao et al., Review Open Access Direct effects of metformin in the endometrium: a hypothetical mechanism for the treatment of women with PCOS and endometrial carcinoma, Journal of Experimental & Clinical Cancer Research 2014, 33(1):41, 11 pages.
Sharma, H.C., et al., Physical Properties of Progesterone Selected Refer, SciFinder, pp. 1-5, Feb. 24, 2014, American Chem. Society & US Natl. Lib. of Med.
Shrier et al., "Mucosal Immunity of the Adolescent Female Genital Tract," Journal of Adolescent Health, 2003; 32:183-186.
Shufelt et al., Hormone therapy dose, formulation, route delivery, and risk of cardiovascular events in women: findings from the Women's Health Initiative Observational Study, Menopause: The Journal of the North American Menopause Society, vol. 21, No. 3, 2014, pp. 1-7, 2013.
Siew, Adeline, moderator, Bioavailability Enhancement with Lipid-Based Drug-Delivery Systems, Pharmaceutical Technology, Aug. 2014, pp. 28, 30-31.
Sigma-Aldrich, Progesterone-Water Soluble: powder, BioReagent, suitable for cell culture), MSDS available online: http://www.sigmaaldrich.com/catalog/product/sigma/p7556.
Simon et al., Effective Treatment of Vaginal atrophy with an Ultra-low-dose estradiol vaginal tablet, Obstetrics & Gynocology, vol. 112, No. 5, Nov. 2008, pp. 1053-1060.
Simon, James A., What if the Women's Health Initiative had used transdermal estradiol and oral progesterone instead? Menopause: The Journal of the North American Menopause Society, 2014, vol. 21, No. 7, pp. 1-15.
Sitruk-Ware et al., Progestogens in hormonal replacement therapy: new molecules, risks, and benefits, Menopause: The Journal of the North American Menopause Society. vol. 9, No. 1, pp. 6-15, 2002.
Sitruk-Ware, Regine, "Pharmacological profile of progestins," Maturitas 47 (2004) 277-283.
Sitruk-Ware, Regine, Oral Micronized Progesterone—Bioavailability pharmacokinetics, pharmacological and therapeutic implications—A review, Contraception, Oct. 1987, vol. 36, No. 4, pp. 373-402.
Smith et al., Lower Risk of Cardiovascular Events in Postmenopausal Women Taking Oral Estradiol Compared with Oral Conjugated Equine Estrogens, JAMA Internal Medicine, Published online Sep. 30, 2013, E1-E7. jamainternalmedicine.com.
Smyth et al., Summary of Toxicological Data, A 2-yr Study of Diethylene Glycol Monoethyl Ether in Rats, Fd Cosmet. Toxicol. vol. 2, pp. 641-642, 1964.

(56) References Cited

OTHER PUBLICATIONS

Stanczyk et al., Thereaputically equivalent pharmacokinetic profile across three application sistes for AG200-15, a novel low-estrogen dose contraceptive patch, Contraception, 87 (2013) pp. 744-749.
Stanczyk, F.Z. et al., "Percutaneous administration of progesterone: blood levels and endometrial protection," Menopause: The Journal of the North American Menopause Society, 2005, vol. 12, No. 2, pp. 232-237.
Stanczyk, F.Z. et al., Ethinyl estradiol and 17β-estradiol in combined oral contraceptives: pharmacokinetics, pharmacodynamics and risk assessment, Contraception 87 (Jun. 2013) vol. 87, No. 6, pp. 706-727.
Stanczyk, F.Z., "All progestins are not created equal," Steroids 68 (2003) 879-880.
Stanczyk, F.Z., "Treatment of postmenopausal women with topical progesterone creams and gels: are they effective?" Climacteric 2014;17 (Suppl 2):8-11.
Stanczyk, F.Z., Bhavnani, B.R., Current views of hormone therapy for the management and treatment of postmenopausal women, J. Steroid Biochem. Mol. Biol. (2014), Elsevier.
Stein, Emily A, et al., Progesterone Physical Properties, SciFinder, pp. 1-46, Feb. 24, 2014, American Chem. Society & US Natl. Lib. of Med.
Stephenson et al., "Transdermal progesterone: Effects on Menopausal symptoms and on thrombotic, anticoagulant, and inflammatory factors in postmenopausal women," Int J Pharmaceutical Compounding, vol. 12, No. 4, Jul./Aug. 2008, pp. 295-304.
Strickley, Robert T., Solubilizing excipients in oral and injectable formulations, Pharmaceutical Research Feb. 2004, vol. 21, Issue 2, pp. 201-230 (abstract only).
Strocchi, Antonino, Fatty Acid Composition, and Triglyceride Structure of Corn Oil, Hydrogenated Corn Oil, and Corn Oil Margarine, Journal of Food Science, vol. 47, pp. 36-39, 1981.
Struhar, M, et al., Estradiol Benzoate: Preparation of an injection suspension . . . , SciFinder, Cesko-Slovenska Farmacie, vol. 27(6), pp. 245-249, 1978, Bratislava, Czech.
Sullivan et al., "A review of the nonclinical safety of Transcutol®, a highly purified form of diethylene glycol monoethyl ether (DEGEE) used as a pharmaceutical excipient," Food and Chemical Toxicology, 72 (2014) pp. 40-50.
Sun, Jidong, D-Limonene: Safety and Clinical Applications, Alternative Medicine Review vol. 12, No. 3, 2007, pp. 259-264.
Tait, Alex D, Characterization of the Prod. from the Oxidation of Progesterone with Osmium Tetroxide, Dept of Investigative Med., Univ. Cambridge, Gt. Britain pp. 531-542, 1972.
Takacs M. et al., The light sensitivity of corticosteroids in crystalline form, Pharmaceutica acta Helvetiae, vol. 66 (5-6) pp. 137-140, 1991, Hardin Library.
Tan, Melvin S. et al., A Sensitive Method for the Determination of Progesterone in Human Plasma by LC-MS-MS, M1025, Cedra Corporation, Austin, Texas.
Tang et al., Effect of Estrogen and Progesterone on the Development of Endometrial Hyperplasia in the Fischer Rat, Biology of Reproduction 31, 399-413 (1984).
Tas et al., Comparison of antiproliferative effects of metformine and progesterone on estrogen-induced endometrial hyperplasia in rats, Gynecol Endocrinol, Early Online: 1-4, 2013. http://informahealthcare.com/gye.
Tella, S.H., Gallagher, J.C., Prevention and treatment of postmenopausal osteoporosis, J. Steroid Biochem. Mol. Biol. (2013), Elsevier.
Thomas, Joshua, et al., The effect of water solubility of solutes on their flux through human skin in vitro: An . . . Intl. J. of Pharmaceut., vol. 339 pp. 157-167, 2007, Elsevier.
Thomas, Peter, Characteristics of membrane progestin receptor alpha (mPRα) and progesterone membrane receptor component 1 (PGMRC1) and their roles in mediating rapid progestin actions, Frontiers in Neuroendocrinology 29 (2008) 292-312.
Tripathi, R, et al., Study of Polymorphs of Progesterone by Novel Melt Sonocrystallization Technique: A Technical Note, AAPS PhamSciTech, vol. 11, No. 3, Sep. 2010.
Trommer et al., Overcoming the stratum Corneum: The modulation of Skin Penetration, Skin Pharmacol Physiol 2006;19:106-121.
Tuleu et al., "Comparative Bioavailability Study in Dogs of a Self-Emulsifying Formulation of Progesterone Presented in a Pellet and Liquid Form Compared with an Aqueous Suspension of Progesterone," Journal of Pharmaceutical Sciences, vol. 93, No. 6, Jun. 2004, pp. 1495-1502.
Ueda et al., Topical and Transdermal Drug Products, Pharmacopeial Forum, vol. 35(3) [May-Jun. 2009], 750-754.
USP, 401 Fats and Fixed Oils, Chemical Tests, Second Suplement to USP36-NF 31, pp. 6141-6151, 2013.
USP, Certificate—Corn Oil, Lot G0L404, Jul. 2013.
USP, Lauroyl Polyoxylglycerides, Safety Data Sheet, US, 5611 Version #02, pp. 1-9, 2013.
USP, Monographs: Progesterone, USP29, www.pharmacopeia.cn/v29240/usp29nf24s0_m69870.html, search done: Feb. 25, 2014.
USP, Official Monographs, Corn Oil, NF 31, pp. 1970-1971, Dec. 2013.
USP, Official Monographs, Lauroyl Polyoxylglycerides, NF 31, pp. 2064-2066, Dec. 2013.
USP, Official Monographs, Medium Chain Triglycerides, NF 31, pp. 2271-2272, Dec. 2013.
USP, Official Monographs, Mono- and Di-glycerides, NF 31, pp. 2101, Dec. 2013.
U.S. Appl. No. 12/561,515, filed Dec. 12, 2011 Non-Final Office Action.
U.S. Appl. No. 12/561,515, filed Oct. 26, 2012 Final Office Action.
U.S. Appl. No. 12/561,515, filed Sep. 11, 2013 Notice of Allowance.
U.S. Appl. No. 13/684,002, filed Mar. 20, 2013 Non-Final Office Action.
U.S. Appl. No. 13/684,002, filed Jul. 16, 2013 Final Office Action.
U.S. Appl. No. 13/684,002, filed Dec. 6, 2013 Notice of Allowance.
U.S. Appl. No. 13/843,362, filed Mar. 16, 2015 Restriction Requirement.
U.S. Appl. No. 13/843,428, filed Apr. 14, 2015 Restriction Requirement.
U.S. Appl. No. 13/843,428, filed Jul. 2, 2015 Non-Final Office Action.
U.S. Appl. No. 14/099,545, filed Feb. 18, 2014_Non_Final_Office_Action.
U.S. Appl. No. 14/099,545, filed Jul. 14, 2014_Notice_of_Allowance.
U.S. Appl. No. 14/099,562, filed Feb. 20, 2014_Restriction_Requirement.
U.S. Appl. No. 14/099,562, filed Mar. 27, 2014_Non-Final_Office_Action.
U.S. Appl. No. 14/099,562, filed Jul. 2, 2014_Final_Office_Action.
U.S. Appl. No. 14/099,562, filed Dec. 10, 2014_Notice_of_Allowance.
U.S. Appl. No. 14/099,571, filed Mar. 28, 2014_Restriction_Requirement.
U.S. Appl. No. 14/099,571, filed Jul. 15, 2014_Notice_of_Allowance.
U.S. Appl. No. 14/099,582, filed Apr. 29, 2014_Restriction_Requirement.
U.S. Appl. No. 14/099,582, filed Jun. 17, 2014_Non-Final_Office_Action.
U.S. Appl. No. 14/099,582, filed Nov. 7, 2014_Notice_of_Allowance.
U.S. Appl. No. 14/099,582, filed Jan. 22, 2015_Notice_of_Allowance.
U.S. Appl. No. 14/099,598, filed May 13, 2014_Restriction_Requirement.
U.S. Appl. No. 14/099,598, filed Jul. 3, 2014_Non-Final_Office_Action.
U.S. Appl. No. 14/099,598, filed Dec. 10, 2014_Notice_of_Allowance.
U.S. Appl. No. 14/099,612, filed Mar. 20, 2014_Restriction_Requirement.
U.S. Appl. No. 14/099,612, filed Oct. 30, 2014_Non-Final_Office_Action.
U.S. Appl. No. 14/099,612, filed Nov. 26, 2014_Notice_of_Allowance.

(56) References Cited

OTHER PUBLICATIONS

U.S. Appl. No. 14/099,623, filed Mar. 5, 2014_Restriction_Requirement.
U.S. Appl. No. 14/099,623, filed Jul. 18, 2014_Non-Final_Office_Action.
U.S. Appl. No. 14/099,623, filed Dec. 15, 2014_Notice_of_Allowance.
U.S. Appl. No. 14/106,655, filed Jul. 3, 2014_Restriction_Requirement.
U.S. Appl. No. 14/106,655, filed Dec. 8, 2014_Non-Final_Office_Action.
U.S. Appl. No. 14/106,655, filed Jun. 19, 2015 Final Office Action.
U.S. Appl. No. 14/125,554, filed Dec. 5, 2014_Restriction_Requirement.
U.S. Appl. No. 14/125,554, filed Apr. 14, 2015_Non-Final_Office_Action.
U.S. Appl. No. 14/136,048, filed Nov. 4, 2014_Restriction_Requirement.
U.S. Appl. No. 14/136,048, filed Mar. 12, 2015_Non-Final_Office_Action.
U.S. Appl. No. 14/475,814, filed Oct. 1, 2014_Non-Final_Office_Action.
U.S. Appl. No. 14/475,814, filed Feb. 13, 2015_Notice_of_Allowance.
U.S. Appl. No. 14/475,864, filed Oct. 2, 2014_Non-Final_Office_Action.
U.S. Appl. No. 14/475,864, filed Feb. 11, 2015_Notice_of_Allowance.
U.S. Appl. No. 14/521,230, filed Dec. 5, 2014_Restriction_Requirement.
U.S. Appl. No. 14/521,230, filed Feb. 18, 2015_Non-Final_Office_Action.
U.S. Appl. No. 14/624,051, filed Apr. 7, 2015_Non-Final_Office_Action.
U.S. Appl. No. 14/690,955, filed Feb. 1, 2016_Non-Final_Office_Action.
Utian, Wulf H, et al., Relief of vasomotor symptoms and vaginal atrophy with lower doses of conjugated equine estrogens, Fertility and Sterility, vol. 75(6) pp. 1065, Jun. 2001.
Voegtline et al., Dispatches from the interface of salivary bioscience and neonatal research, Frontiers in Endocrinology, Mar. 2014, vol. 5, article 25, 8 pages.
Waddell et al., Distribution and metabolism of topically applied progesterone in a rat model, Journal of Steroid Biochemistry & Molecular Biology 80 (2002) 449-455.
Waddell et al., The Metabolic Clearance of Progesterone in the Pregnant Rat: Absence of a Physiological Role for the Lung, Biology of Reproduction 40, 1188-1193 (1989).
Walter et al., The role of progesterone in endometrial angiogenesis in pregnant and ovariectomised mice, Reproduction (2005) 129 765-777.
Weber, E.J., Corn Lipids, Cereal Chem., vol. 55(5), pp. 572-584, The American Assoc of Cereal Chem, Sep.-Oct. 1978.
Weber, M.T., et al., Cognition and mood in perimenopause: A systematic review and meta-analysis, J. Steroid Biochem. Mol. Biol. (2013), Elsevier.
Weintraub, Arlene, "Women fooled by untested hormones from compounding pharmacies," Forbes, Feb. 20, 2015; retrieved online at http://onforb.es/1LlUm1V_on Feb. 23, 2015, 3 pages.
Whitehead et al., Absorption and metabolism of oral progesterone, The British Medical Journal, vol. 280, No. 6217 (Mar. 22, 1980), pp. 825-827, BMJ Publishing Group.
Wiranidchapong, Chutima, Method of preparation does not affect the miscibility between steroid hormone and polymethacrylate, Thermochimica Acta 485, Elsevier, pp. 57, 2009.
Wood et al., Effects of estradiol with micronized progesterone or medroxyprogesterone acetate on risk markers for breast cancer in postmenopausal monkeys, Breast Cancer Res Treat (2007) 101:125-134.
Wren et al., Effect of sequential transdermal progesterone cream on endometrium, bleeding pattern, and plasma progesterone and salivary progesterone levels in postmenopausal women, Climacteric, 2000, 3(3), pp. 155-160. http://dx.doi.org/10.1080/13697130008500109.
Wu et al., Gene Expression Profiling of the Effects of Castration and Estrogen Treatment in the Rat Uterus, Biology of Reproduction 69, 1308-1317 (2003).
Yalkowsky, Samuel H, & Valvani, Shri C, Solubility and Partitioning I: Solubility of Nonelectrolytes in Water, J. of Pharmaceutical Sciences, vol. 69(8) pp. 912-922, 1980.
Yalkowsky, Samuel H, Handbook of Acqueous Solubility Data, Solutions, 2003, pp. 1110-1111, CRC Press, Boca Raton, London, New York, Wash. D.C.
Yue, W., Genotoxic metabolites of estradiol in breast: potential mechanism of estradiol induced carcinogenesis, Journal of Steroid Biochem & Mol Biology, vol. 86 pp. 477-486, 2003.
Zava, David T. et al., Percutaneous absorption of progesterone, Maturitas 77 (2014) 91-92, Elsevier.
Zava, David T., Topical Progesterone Delivery and Levels in Serum, Saliva, Capillary Blood, and Tissues, Script, ZRT Laboratory, pp. 4-5. http://www.zrtlab.com/component/docman/cat_view/10-publications?Itemid.
Ettinger et al., "Measuring symptom relief in studies of vaginal and vulvar atrophy: the most bothersome symptom approach," Menopause, vol. 15, No. 5, 2008, pp. 885-889.
Eugster-Hausmann et al., "Minimized estradiol absorption with ultra-low-dose 10 μg 17β-estradiol vaginal tablets," Climacteric 2010;13:219-227.
Hitchcock, Christine L. et al., "Oral micronized progesterone for vasomotor symptoms—a placebo-controlled randomized trial in healthy postmenopausal women," Menopause: The Journal of the North American Menopause Society. 19(8):886-893, Aug. 2012.
March, Charles M. et al., "Roles of Estradiol and Progesterone in Eliciting the Midcycle Luteinizing Hormone and Follicle-Stimulating Hormone Surges," The Journal of Clinical Endocrinology & Metabolism, vol. 49, Issue 4, Oct. 1, 1979, pp. 507-513.
Simon, James A. et al., "A vaginal estradiol softgel capsule, TX-004HR, has negligible to very low systemic absorption of estradiol: Efficacy and pharmacokineticdata review," Maturitas 99 (2017) 51-58.
Sofi, Showkat Hussain et al., "Gelucire: A Versatile Formulation Excipient," Ijppr.Human, 2017; vol. 10 (3): 55-73.
Stefanick, "Estrogens and progestins: background and history, trends in use, and guidelines and regimens approved by the US Food and Drug Administration," The American Journal of Medicine (2005) vol. 118 (12B), 64S-73S.
U.S. Appl. No. 16/104,101, filed Aug. 16, 2018.
U.S. Appl. No. 16/125,201, filed Sep. 7, 2018.
Hosmer, Jaclyn et al., "Microemulsions Containing Medium-Chain Glycerides as Transdermal Delivery Systems for Hydrophilic and Hydrophobic Drugs," AAPS PharmSciTech, 2009, vol. 10, No. 2, pp. 589-596.
U.S. Appl. No. 13/684,002, filed Nov. 21, 2012, U.S. Pat. No. 8,633,178, Jan. 21, 2014.
U.S. Appl. No. 13/843,362, filed Mar. 15, 2013.
U.S. Appl. No. 13/843,428, filed Mar. 15, 2013, U.S. Pat. No. 9,301,920, Apr. 5, 2016.
U.S. Appl. No. 14/099,545, filed Dec. 6, 2013, U.S. Pat. No. 8,846,648, Sep. 30, 2014.
U.S. Appl. No. 14/099,562, filed Dec. 6, 2013, U.S. Pat. No. 8,987,237, Mar. 24, 2015.
U.S. Appl. No. 14/099,571, filed Dec. 6, 2013, U.S. Pat. No. 8,846,649, Sep. 30, 2014.
U.S. Appl. No. 14/099,582, filed Dec. 6, 2013, U.S. Pat. No. 9,012,434, Apr. 21, 2015.
U.S. Appl. No. 14/099,598, filed Dec. 6, 2013, U.S. Pat. No. 8,987,238, Mar. 24, 2015.
U.S. Appl. No. 14/099,612, filed Dec. 6, 2013, U.S. Pat. No. 8,933,059, Jan. 13, 2015.
U.S. Appl. No. 14/099,623, filed Dec. 6, 2013, U.S. Pat. No. 9,006,222, Apr. 14, 2015.
U.S. Appl. No. 14/106,655, filed Dec. 13, 2013.

(56) References Cited

OTHER PUBLICATIONS

U.S. Appl. No. 14/125,554, filed Jan. 25, 2013, U.S. Pat. No. 9,248,136, Feb. 2, 2016.
U.S. Appl. No. 14/136,048, filed Dec. 20, 2013, U.S. Pat. No. 9,180,091, Nov. 10, 2015.
U.S. Appl. No. 14/475,814, filed Sep. 3, 2014, U.S. Pat. No. 8,993,548, Mar. 31, 2015.
U.S. Appl. No. 14/475,864, filed Sep. 3, 2014, U.S. Pat. No. 8,993,549, Mar. 31, 2015.
U.S. Appl. No. 14/475,946, filed Sep. 3, 2014, U.S. Pat. No. 9,114,145, Aug. 25, 2015.
U.S. Appl. No. 14/476,040, filed Sep. 3, 2014, U.S. Pat. No. 9,114,146, Aug. 25, 2015.
U.S. Appl. No. 14/512,046, filed Oct. 10, 2014.
U.S. Appl. No. 14/521,002, filed Oct. 22, 2014.
U.S. Appl. No. 14/521,230, filed Oct. 22, 2014.
U.S. Appl. No. 14/624,051, filed Feb. 17, 2015, U.S. Pat. No. 9,289,382, Mar. 22, 2016.
U.S. Appl. No. 14/649,818, filed Jun. 18, 2013.
U.S. Appl. No. 14/690,913, filed Apr. 20, 2015.
U.S. Appl. No. 14/690,955, filed Apr. 20, 2015.
U.S. Appl. No. 14/719,933, filed May 22, 2015.
U.S. Appl. No. 14/812,179, filed Jul. 29, 2015.
U.S. Appl. No. 14/830,398, filed Aug. 19, 2015.
U.S. Appl. No. 15/372,385, filed Dec. 7, 2016.
U.S. Appl. No. 15/420,019, filed Jan. 30, 2017.
U.S. Appl. No. 15/475,052, filed Mar. 30, 2017.
U.S. Appl. No. 15/475,068, filed Mar. 30, 2017.
U.S. Appl. No. 15/781,840, filed Jun. 6, 2018.
U.S. Appl. No. 15/832,750, filed Dec. 5, 2017.
U.S. Appl. No. 15/832,757, filed Dec. 5, 2017.
U.S. Appl. No. 15/893,542, filed Feb. 9, 2018.
U.S. Appl. No. 15/893,546, filed Feb. 9, 2018.
U.S. Appl. No. 15/893,550, filed Feb. 9, 2018.
U.S. Appl. No. 15/975,723, filed May 9, 2018.
U.S. Appl. No. 15/975,733, filed May 9, 2018.
U.S. Appl. No. 16/004,338, filed Jun. 8, 2018.
U.S. Appl. No. 16/006,721, filed Jun. 12, 2018.

* cited by examiner

NATURAL COMBINATION HORMONE REPLACEMENT FORMULATIONS AND THERAPIES

CROSS REFERENCE TO RELATED APPLICATIONS

This application claims priority to the following U.S. patent applications: U.S. application Ser. No. 13/843,428, entitled "NATURAL COMBINATION HORMONE REPLACEMENT FORMULATIONS AND THERAPIES," which was filed Mar. 15, 2013; U.S. application Ser. No. 13/684,002, entitled "NATURAL COMBINATION HORMONE REPLACEMENT THERAPIES," which was filed on Nov. 21, 2012; U.S. Provisional Application Ser. No. 61/661,302, entitled "ESTRADIOL FORMULATIONS," which was filed on Jun. 18, 2012; and U.S. Provisional Application Ser. No. 61/662,265, entitled "PROGESTERONE FORMULATIONS," which was filed on Jun. 20, 2012. All aforementioned applications are hereby incorporated by reference herein in their entirety.

BACKGROUND

Field

This disclosure relates to natural estrogen and progesterone replacement therapies, with formulations provided for each estradiol and progesterone alone and in combination for the treatment of pre, peri-menopausal, menopausal and post-menopausal females in relation to the treatment of Estrogen- and Progesterone-deficient States, each as herein below defined.

Discussion of the Related Art

Hormone replacement therapy (HRT) is a medical treatment that involves the use of one or more of a group of medications designed to increase hormone levels in women who lack adequate hormone production. HRT can mitigate and prevent symptoms caused by diminished circulating estrogen and progesterone hormones regardless as to whether the subject is pre-menopausal, peri-menopausal, menopausal or post-menopausal. However, specific disease states can exist during each stage of menopausal progression.

HRT is presently available in various forms. One therapy involves administration of low dosages of one or more estrogens. Another involves administration of progesterone or a chemical analogue, called a progestin. Progesterone administration acts, among treating other disease states, to mitigate certain undesirable side effects from estrogen administration including, for example, endometrial hyperplasia (thickening), reducing the incidence of endometrial cancer.

Timing for dosage administration is often varied cyclically, with estrogens taken daily and progesterone taken for approximately two weeks of every month; a method often referred to as "Cyclic-Sequential" or "Sequentially-Combined HRT." This method is intended to mimic the natural menstrual cycle and typically causes menstruation similar to a period after the progesterone is stopped. This regimen is most typically used in peri-menopausal or newly menopausal women as the alternative continuous method often results in irregular bleeding in such women. An alternate method, a constant dosage with both estrogen and progesterone taken daily, is called "continuous-combined HRT." This method usually results in no menstruation and is used most often after a woman has been menopausal for some time.

Estrogen, in its various forms, and progesterone, in its various forms, are used in HRT via a variety of administered dosage forms including, for example, via tablets, capsules and patches.

"Bio-identical" hormones, which are identical in chemical structure to the hormones naturally produced by human bodies can be used and are often referred to as natural hormone replacement therapy, or NHRT.

These natural or bio-identical hormones are formulated from various ingredients to match the chemical structure and effect of estradiol, estrone, or estriol (the 3 primary estrogens) as well as progesterone that occur naturally in the human body (endogenous).

Currently, bio-identical estradiol is available in both branded and generic FDA approved versions. FDA-approved bio-identical progesterone for HRT is available as the branded stand-alone drug commercially identified as Prometrium® (Abbott Laboratories, Abbott Park, Ill.), with a generic authorized by the innovator, and generic products provided by Teva (Israel) and Sofgen Americas, Inc (New York). Prometrium was approved for sale in the United States on May 14, 1998 under NDA # N019781. According to the prescribing information approved for this product (Rev June 2009) ("Prometrium prescribing information"), Prometrium comprises synthetic progesterone that is chemically identical to progesterone of human ovarian origin. Capsules comprise 100 mg or 200 mg of micronized progesterone. The inactive ingredients include peanut oil, gelatin, glycerin, lecithin, titanium dioxide, and yellow and red dyes.

Other products such as Prempro® and Premphase® (Wyeth Laboratories, a division Pfizer, Inc., New York) provide both continuous-combined and cyclic-sequential products containing Premarin (estrogen derived from mare's urine) and synthetic medroxyprogesterone acetate. Other products are available. However, no FDA approved product exists on the market today with combination bio-identical estradiol and bio-identical progesterone.

SUMMARY

According to various embodiments of the disclosure, natural hormone replacement therapies are provided comprising cyclic/sequential and continuous-combined delivery via pharmaceutical formulations of solubilized estradiol and micronized and/or partially or completely solubilized progesterone. Estradiol and micronized and/or partially or completely solubilized progesterone delivered together daily can be combined in either a single unit dose or in separate unit doses, typically in a soft capsule. A 28-day or monthly regimen of tablets or capsules can be packaged in a single blister pack having delivery days identified to improve compliance. Various examples formulations of natural hormones, and the use of these formulations for hormone replacement therapies, each in accordance with the invention are set forth below.

BRIEF DESCRIPTION OF THE DRAWINGS/FIGURES

The accompanying drawings, which are incorporated herein and form a part of the specification, illustrate the present disclosure and, together with the description, further serve to explain the principles of the disclosure and to enable a person skilled in the pertinent art to make and use the disclosed embodiments.

DETAILED DESCRIPTION OF THE ILLUSTRATED EMBODIMENTS

Figure 1:
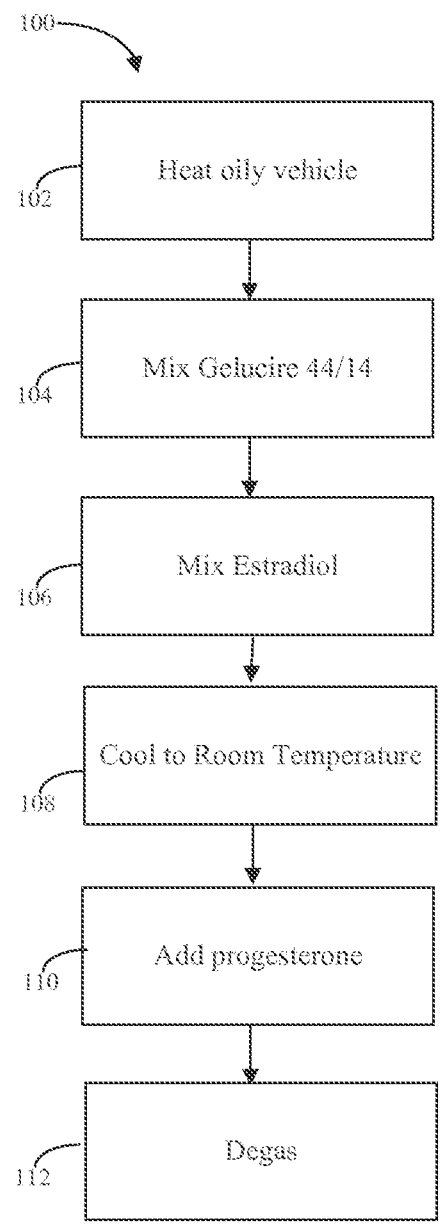
FIG. 1 illustrates an exemplary manufacturing process of a fill material in accordance with various embodiments.

Frequently, higher recommended oral dosages of pharmaceuticals are necessary to treat a given disease state because many active ingredients are not completely absorbed by a patient in need of treatment. In other words, a better-absorbed dosage form of a medicament such as, for example, progesterone, or dosage forms that provide greater consistency of absorption of progesterone among subjects, alone or in combination with estradiol, may be able to be administered at dosage strengths lower than presently recommended, potentially resulting in a reduced or minimized side effect profile, among other potential benefits.

Definitions

The term "micronized progesterone," as used herein, includes micronized progesterone having an X50 particle size value below about 15 microns and/or having an X90 particle size value below about 25 microns.

The term "X50," as used herein, means that one-half of the particles in a sample are smaller in diameter than a given number. For example, micronized progesterone having an X50 of 5 microns means that, for a given sample of micronized progesterone, one-half of the particles have a diameter of less than 5 microns. Similarly, the term "X90" means that ninety percent (90%) of the particles in a sample are smaller in diameter than a given number.

The term "medium chain," as used herein means any medium chain carbon-containing substance, including C4-C18, and including C6-C12 substances, fatty acid esters of glycerol, fatty acids, and mono-, di-, and tri-glycerides of such substances.

The term "uniform distribution" means at least one of uniform dispersion, solubility, or lack of agglomeration of progesterone in a dissolution test compared to Prometrium at a similar dosage strength and the same USP dissolution apparatus.

The term "bioavailability," as used herein means the concentration of an active ingredient (e.g., progesterone or estradiol or estrone) in the blood (serum or plasma). The relative bioavailability may be measured as the concentration in the blood (serum or plasma) versus time. Other pharmacokinetic (pK) indicators may be used to measure and assess bioavailability, determined by suitable metrics including AUC, Cmax, and optionally, Tmax.

The term "AUC," as used herein, refers to the area under the curve that represents changes in blood concentration of progesterone, estradiol or estrone over time.

The term, "Cmax" as used herein, refers to the maximum value of blood concentration shown on the curve that represents changes in blood concentrations of progesterone, estradiol or estrone over time.

The term, "Tmax" as used herein, refers to the time that it takes for progesterone, estradiol or estrone blood concentration to reach the maximum value.

Collectively AUC, Cmax and, optionally, Tmax are the principle pharmacokinetic parameters that can characterize the pharmacokinetic responses of a particular drug product such as progesterone in an animal especially a mammal, including human, subject.

The term "solubilizer," as used herein, means any substance or mixture of substances that may be used to enhance the solubility of estradiol, including, for example and without limitation, appropriate pharmaceutically acceptable excipients, such as solvents, co-solvents, surfactants, emulsifiers, oils and carriers.

The term "excipients," as used herein, refer to non-active pharmaceutical ingredients ("API") substances such as carriers, solvents, oils, lubricants and others used in formulating pharmaceutical products. They are generally safe for administering to animals, especially mammals, including humans, according to established governmental standards, including those promulgated by the United States Food and Drug Administration.

The term "oil" as used herein may be any pharmaceutically acceptable substance, such as an organic oil other than peanut oil, that would suspend and/or solubilize any suitable progesterone, starting material, or precursor, including micronized progesterone as described herein. More specifically, oils may include, for example and without limitation, medium chain fatty acids, generally of the group known as medium chain fatty acids consisting of at least one mono-, di-, and triglyceride, or derivatives thereof, or combinations thereof.

"Fully solubilized progesterone" as used herein means progesterone which is about 100% in solution, i.e., at least 98% in solution.

"Partially solubilized progesterone" as used herein means progesterone which is in any state of solubilization up to but not including about 100%, i.e., up to but not including 98% in solution.

As used herein, unless specified, estradiol includes estradiol in anhydrous and hemihydrate forms.

DESCRIPTION

Provided herein are the following formulations: solubilized estradiol without progesterone; micronized progesterone without estradiol; micronized progesterone with partially solubilized progesterone; solubilized estradiol with micronized progesterone; solubilized estradiol with micronized progesterone in combination with partially solubilized progesterone; and solubilized estradiol with solubilized progesterone. The underlying formulation concepts provided herein may be used with other natural or synthetic forms of estradiol and progesterone. Micronization specifications, aspects and embodiments are further defined herein.

Generally, the pharmaceutical formulations described herein are prepared and administered as filled capsules, typically soft capsules of one or more materials well known in the art including, for example and without limitation, soft gelatin capsules. Micronized progesterone, as described herein, may also be prepared for administration in tablets or other well-known orally administered dosage forms using standard techniques.

Another aspect of the present disclosure includes a pharmaceutical formulation of micronized progesterone, micronized progesterone with partially solubilized progesterone and fully solubilized progesterone, wherein said formulation may provide increased progesterone bioavailability in a treated subject compared to the bioavailability provided by Prometrium® when administered at equal dosage strengths.

In accordance with various aspects and embodiments, the solubility proportion (i.e., the proportion of a solute that enters solution) is notable. The weight ratio of estradiol to the weight of the entire solution is also notable due to the intended dose amounts, discussed herein. In particular, it is desirable to obtain a target dosage of estradiol in an amount of solution that may be readily administered via a capsule. For example, if it is desired to have a dose of estradiol in a capsule of between about 0.125 mg to about 2 mg, it would also be desirable to have a total solution weight to be between about 250 mg to about 400 mg, preferably about 300 mg to about 350 mg and more preferably about 325 mg. In various embodiments, the following weight ratios of estradiol to total solution is from about 0.125/50 mg to about 0.125/1000 mg, from about 1 mg:500 mg to about 1 mg:50 mg; from about 1 mg:250 mg to about 1 mg:60 mg; from about 1 mg:100 mg to about 1 mg:66 mg; from about 2 mg/50 mg to about 2 mg/1000 mg. In various embodiments, the target for single dose product is 325 mg, and a target fill weight for a combination product (e.g., two or more sterol APIs) is 650 mg.

In illustrative embodiments, total progesterone, i.e., dissolved and micronized, is 20 to 50 wt %, e.g., 30 to 35 wt %; estradiol is 0.1 to 0.8 wt %, e.g., 0.15 to 0.35 wt %.

Other aspects of the present disclosure further provide: more uniform dissolution of progesterone, and reduced intra- and inter-patient blood level variability in formulations of progesterone of the present disclosure, typically in combinations with solubilized estradiol, when compared to equal dosages of Prometrium. Blood level variability is also compared at equal sampling times following administration. Not to be limited by theory, these aspects are believed to be influenced by the percentage of solubilized progesterone in a respective formulation wherein such more uniform dissolution of progesterone, and lower intra- and inter-patient blood level variability, are influenced by a greater proportion of solubilized progesterone relative to total progesterone. A reduced food effect with the present formulations comprising progesterone may also be implicated.

According to the Prometrium prescribing information, clinical trials have shown significant patient variability. For example, a clinical trial involving postmenopausal women who were administered Prometrium once a day for five days resulted in the mean PK parameters listed in the following table:

|  | Prometrium Capsules Daily Dose | | |
| --- | --- | --- | --- |
| Parameter | 100 mg | 200 mg | 300 mg |
| $C_{max}$ (ng/ml) | 17.3 +/− 21.9 | 38.1 +/− 37.8 | 60.6 +/− 72.5 |
| $T_{max}$ (hr) | 1.5 +/− 0.8 | 2.3 +/− 1.4 | 1.7 +/− 0.6 |
| $AUC_{0-10}$ (ng × hr/ml) | 43.4 +/− 30.8 | 101.2 +/− 66.0 | 175.7 +/− 170.3 |

In a particular illustrative aspects and embodiments of this invention, it is possible, though not necessary, to reduce the standard deviations in one or more of these PK parameters.

More uniform dissolution of progesterone in a formulation of the present disclosure compared to the dissolution of Prometrium at equal dosage strengths and using the same USP apparatus can be determined using standard techniques established for API dissolution testing, including that which is described in the examples below.

Reduced intra- and inter-patient variability of progesterone formulated pursuant to the present disclosure compared to Prometrium can be demonstrated via a fed bio-study such as that described below.

Other aspects of the present disclosure includes the use of formulations as described herein wherein progesterone is at least one API in said formulation for the treatment of an animal, especially a mammal, including humans: for endometrial hyperplasia; for secondary amenorrhea; as a method of treatment for preterm birth, when said animal has a shortened cervix, and other disease states or conditions treated with supplemental progesterone (collectively, "Progesterone-deficient States"); and the use of formulations as described herein wherein estradiol is at least one API in said formulation for the treatment of an animal, especially a mammal, including humans, having menopause-related symptoms including, for example, vasomotor symptoms; in relation to treatment of hypoestrogenism related symptoms including, for example and without limitation, hot flashes and night sweats (vasomotor symptoms), sleep disturbances, mood changes and vulvo-vaginal atrophy; and osteoporosis and other non-menopausal disease states or conditions treated with supplemental estrogen. (collectively, "Estrogen-deficient States"), each in a subject in need of treatment, and each with a non-toxic effective amount of said formulations. As used herein, the term "treatment", or a derivative thereof, contemplates partial or complete inhibition of the stated disease state when a formulation as described herein is administered prophylactically or following the onset of the disease state for which such formulation is administered. For the purposes of the present disclosure, "prophylaxis" refers to administration of the active ingredient(s) to an animal especially a mammal, to protect the animal from any of the disorders set forth herein, as well as others.

Unless otherwise specified, "natural," as used herein with reference to hormones discussed herein, means bio-identical hormones formulated to match the chemical structure and effect of those that occur naturally in the human body (endogenous). An exemplary natural estrogen is estradiol (also described as 17β-estradiol and E2) and a natural progestin is progesterone. An exemplary cyclic/sequential regimen comprises delivery of from about 0.125 mg to about 2.0 mg of estradiol daily for 14-18 days, followed by delivery of from about 0.125 mg to about 2 mg of estradiol and about 25 mg to about 200 mg of progesterone daily for 10-14 days. Cyclic/sequential regimens may be especially useful for menopausal females. Other exemplary dosage strengths for estradiol for use in the formulations described herein include, without limitation, 0.125, 0.25, 0.375, 0.50, 0.625, 0.75, 1.00, 1.125, 1.25, 1.375, 1.50, 1.625, 1.75 and 2.00 mg. Other exemplary dosage strengths for progesterone for use in the formulations described herein include, without limitation, 25, 50, 75, 100, 125, 150, 175, 200 mg, 250 mg, 300 mg, 350 mg and 400 mg. These dosage strengths for each of estradiol and progesterone can be administered in formulations described herein either alone or in combination.

Progesterone active pharmaceutical ingredient may be micronized via any one of the multiple methods typically utilized by the ordinarily skilled artisan. In various embodiments, micronized progesterone has an X50 particle size value of less than about 15 microns, less than about 10 microns, less than about 5 microns and/or less than about 3 microns. In various embodiments, micronized progesterone has an X90 particle size value of less than about 25 microns, less than about 20 microns, and/or less than about 15 microns.

Particle size may be determined in any suitable manner. For example, a Beckman Coulter LS 13 320 Laser Diffraction Particle Size Analyzer (the "Beckman Device") may be used to determine particle size. As described above, particle size may be represented by various metrics, for example, through an X50 particle size, and/or X90 particle size, or similar descriptions of particle size.

The Beckman Device may be used with various modules for introducing a sample for analysis. The Beckman Device may be used with the LS 13 320 Universal Liquid Module ("ULM"). The ULM is capable of suspending samples in the size range of 0.017 µm to 2000 µm. The ULM is a liquid based module that allows for delivery of the sample to the sensing zone. The ULM recirculates the sample through the Beckman Device. The ULM comprises two hoses, one for fluid delivery and another for waste. The total volume used may be 125 mL or less. A sample mass of from about 1 mg to about 10 g may be used. The ULM may interact with the Beckman Device via pins that fit into slots on the ULM. The ULM may use a variety of suspension fluids, for example, water, butonol, ethanol, chloroform, heptanes, toluene, propanol, COULTER Type 1B Dispersant ("Coulter 1B"), and a variety of other suspension fluids. Surfactants may also be used, though pump speed should be adjusted to prevent excessive bubbling. Coulter 1B may comprise one or more of acetaldehyde, ethylene oxide, and/or 1,4-dioxane. The Beckman Device may be configured to use a variety of optical theories, including the Fraunhofer optical model and the Mie Theory.

The Beckman Device may comprise software to control the Beckman Device while the ULM is in use. The software may control, for example, pump speed, use of de-bubble routine, rinse routine, sonicate routine, and fill routine, among others. Parameters regarding the sample run may also be configured. For example, run length may be set. Though any suitable run length may be used, in various embodiments, a time period of 30 seconds to 120 seconds, and preferably between 30 seconds and 90 seconds may be used.

The Beckman Device may be used with the LS 13 320 Micro Liquid Module ("MLM"). The MLM is capable of suspending samples in the size range of 0.4 µm to 2000 µm. The MLM is a liquid based module that allows for delivery of the sample to the sensing zone. The MLM includes a stirrer. The total volume used may be 12 mL or less. The MLM may use a variety of suspension fluids, both aqueous and non-aqueous.

Each of estradiol and progesterone as described herein can be formulated alone pursuant to the teachings below. These formulations can be prepared for oral administration or can be combined, based on compatibility, for co-administration of estradiol and progesterone in a single oral unit dosage form.

Progesterone formulations of the present disclosure are prepared via blending with a pharmaceutically acceptable oil; generally, the oil comprises at least one medium chain fatty acid such as medium chain fatty acids consisting of at least one mono-, di-, or triglyceride, or derivatives thereof, or combinations thereof. Optionally added are other excipients including, for example and without limitation, antioxidants, lubricants and the like. Sufficient oil is used to form a suspension of micronized progesterone or, in the alternative, solubilize progesterone.

Pharmaceutically acceptable oils include, without limitation, the use of at least one of caproic fatty acid; caprylic fatty acid; capric fatty acid; tauric acid; myristic acid; linoleic acid; succinic acid; glycerin; mono-, di-, or triglycerides and combinations and derivatives thereof a polyethylene glycol; a polyethylene glycol glyceride (Gelucire®; GATTEFOSSE SAS, Saint-Priest, France); a propylene glycol; a caprylic/capric triglyceride (Miglyol®; SASOL Germany GMBH, Hamburg; Miglyol includes Miglyol 810, 812, 816 and 829); a caproic/caprylic/capric/lauric triglyceride; a caprylic/capric/linoleic triglyceride; a caprylic/capric/succinic triglyceride; propylene glycol monocaprylate; propylene glycol monocaprate; (Capmul® PG-8 and 10; the Capmul brands are owned by ABITEC, Columbus Ohio); propylene glycol dicaprylate; propylene glycol dicaprylate; medium chain mono- and diglycerides (Capmul MCM); a diethylene glycol mono ester (including 2-(2-Ethoxyethoxy) ethanol: Transcutol); diethylene glycol monoethyl ether; esters of saturated coconut and palm kernel oil and derivatives thereof; triglycerides of fractionated vegetable fatty acids, and combinations and derivatives thereof.

In other aspects and embodiments, progesterone is fully solubilized using, for example and without limitation, sufficient amounts of: Transcutol and Miglyol; Transcutol, Miglyol and Capmul PG 8 and/or PG 10; Capmul MCM; Capmul MCM and a non-ionic surfactant; and Capmul MCM and Gelucire.

Various ratios of these oils can be used for full solubilization of progesterone. Capmul MCM and a non-ionic surfactant, e.g., Gelucire 44/14, can be used at ratios of about 99:1 to 2:1, including, for example and without limitation: 60:40, 65:35, 70:30, 75:25, 80:10, 80:15, 85:20, 90:10, and 98:1. The ratios of oil (e.g., medium chain fatty acid esters of monoglycerides and diglycerides) to non-ionic surfactant can be significantly higher. For example, in certain examples, below, Capmul MCM and Gelucire were used in ratios of up to about 65:1, e.g., 8:1, 22:1, 49:1, 65:1 and 66:1. See, e.g., Tables 13-17, below. Thus, useful ratios can be 8:1 or greater, e.g., 60 to 70:1. Among other combinations, these oils and/or solubilizers, as defined herein, and combinations thereof, can be used to form combination estradiol and progesterone formulations of the present disclosure.

Combinations of these oils can produce partially solubilized progesterone, depending upon the desired unit dosage amount of progesterone. The greater the amount of progesterone per unit dosage form, the less progesterone may be solubilized. The upward limit of dosage strength per unit dose it generally limited only by the practical size of the final dosage form.

In illustrative embodiments of the invention, oils used to solubilize estradiol and to suspend, partially solubilize, or fully solubilize progesterone include medium chain fatty acid esters, (e.g., esters of glycerol, polyethylene glycol, or propylene glycol) and mixtures thereof. In illustrative embodiments, the medium chain fatty acids are C6 to C14 or C6 to C12 fatty acids. In illustrative embodiments, the medium chain fatty acids ore saturated, or predominantly saturated, e.g., greater than about 60% or greater than about 75% saturated. In illustrative embodiments, estradiol or progesterone (or both) is soluble in the oils at room temperature, although it may be desirable to warm the oils up until they are in a liquid state. In illustrative embodiments, the oil or oil/surfactant is liquid at between room temperature and about 50 C, e.g., at or below 50 C, at or below 40 C, or at or below 50 C. In illustrative embodiments, Gelucire 44/14 is heated to about 65 C and Capmul MCM is heated to about 40 C to facilitate mixing of the oil and non-surfactant, although such heating is not necessary to dissolve the estradiol or progesterone. In illustrative embodiments, the solubility of estradiol in the oil (or oil/surfactant) is at least about 0.5 wt %, e.g., 0.8 wt % or higher, or 1.0 wt % or higher.

Illustrative examples of mono- and diglycerides of medium chain fatty acids include, among others, Capmul MCM, Capmul MCM C10, Capmul MCM C8, and Capmul MCM C8 EP. These oils are C8 and C10 fatty acid mono- and diglycerides. Illustrative examples of oils that are triglycerides of medium chain fatty acids include, among others, Miglyol 810 and Miglyol 812.

Illustrative examples of oils that are medium chain fatty acid esters of propylene glycol include, among others, Capmul PG-8, Capmul PG-2L EP/NF, Capmul PG-8 NF, Capmul PG-12 EP/NF and Capryol. Other illustrative examples include Miglyol 840.

Illustrative examples of oils that are medium chain fatty acid esters of polyethylene glycol include, among others, Gelucire 44/14 (PEG-32 glyceryl laurate EP), which is polyethylene glycol glycerides composed of mono-, di- and triglycerides and mono- and diesters of polyethylene glycol. Without intending to be bound to any particular mechanism, it appears that at least in formulations comprising small amounts of Gelucire, e.g., 10 wt % or less, the primary function of this oil is as a non-ionic surfactant.

These illustrative examples comprise predominantly medium chain length, saturated, fatty acids, specifically predominantly C8 to C12 saturated fatty acids. Specifically, a product information sheet for Myglyol by SASOL provides as the composition of fatty acids as follows:

| Tests | 810 | 812 | 818 | 829 | 840 |
|---|---|---|---|---|---|
| Caproic acid (C6:0) | max. 2.0 | max. 2.0 | max. 2 | max. 2 | max. 2 |
| Caprylic acid (C8:0) | 65.0-80.0 | 50.0-65.0 | 45-65 | 45-55 | 65-80 |
| Capric acid (C10:0) | 20.0-35.0 | 30.0-45.0 | 30-45 | 30-40 | 20-35 |
| Lauric acid (C12:0) | max. 2 | max. 2 | max. 3 | max. 3 | max. 2 |
| Myristic acid (C14:0) | max. 1.0 | max. 1.0 | max. 1 | max. 1 | max. 1 |
| Linoleic acid (C18:2) | — | — | 2-5 | — | — |
| Succinic acid | — | — | — | 15-20 | — |

It will be understood that oils are often mixtures. So, for example, when an oil is described herein as a saturated C8 fatty acid mono- or diester of glycerol, it will be understood that the predominant component of the oil, i.e., >50 wt % (e.g., >75 wt %, >85 wt % or >90 wt %) are caprylic monoglycerides and caprylic diglycerides. For example, the Technical Data Sheet by ABITEC for Capmul MCM C8 describes Capmul MCM C8 as being composed of mono and diglycerides of medium chain fatty acids (mainly caprylic) and describes the alkyl content as <=1% C6, >=95% C8, <=5% C10, and <=1.5% C12 and higher, Mixtures of medium chain fatty acid glycerides, e.g., C6-C12, C8-C12, or C8-C10 fatty acid mono- and diglycerides or mono-, di-, and triglycerides are very well suited for dissolving estradiol; good results have been obtained with an oil that is predominantly a mixture of C8-C10 saturated fatty acid mono- and diglycerides. Longer chain glycerides appear to be not as well suited for dissolution of estradiol. On the other hand, high solubility of progesterone has been obtained in mixtures that are predominantly medium chain fatty acid triglycerides.

High solubility of estradiol has been obtained in 2-(2-Ethoxyethoxy)ethanol, e.g., Transcutol and in Propylene glycol monocaprylate, e.g., Capryol™ 90 (Gattefosse).

In illustrative embodiments of the invention, the selected oil does not require excessive heating in order to solubilize progesterone or estradiol. For example, when the formulation comprises medium chain fatty acid mono- and diglycerides (e.g., Capmul MCM) and polyethylene glycol glycerides (e.g., Gelucire) as a surfactant, the oil and/or the surfactant can be warmed up, e.g., to about 65 C in the case of the surfactant and less in the case of the oil, to facilitate mixing of the oil and surfactant. The estradiol can be added at this temperature or at lower temperatures as the mixture cools or even after it has cooled as temperatures above room temperature, e.g., about 20 C, are not required to solubilize the estradiol in preferred oils. The progesterone can also be added as the mixture cools, e.g., to below about 40 C or to below about 30 C, even down to room temperature.

In various embodiments, estradiol is solubilized. Solubilized estradiol may include estradiol that is approximately: 90% soluble in a solvent; 93% soluble in a solvent; 95% soluble in a solvent; 97% soluble in a solvent; 99% soluble in a solvent; and 100% soluble in a solvent. Solubility may be expressed as a mass fraction (% w/w, also referred to as wt %).

In various embodiments, the solubilizing agent is selected from at least one of a solvent or co-solvent. Suitable solvents and co-solvents include any mono-, di- or triglyceride and glycols, and combinations thereof.

In addition to the oils referenced above for progesterone, which can also be used as solubilizers for estradiol, other solubilizers include, for example and without limitation, glyceryl mono- and di-caprylates, propylene glycol and 1,2,3-propanetriol (glycerol, glycerin, glycerine).

Anionic and/or non-ionic surfactants can be used in other embodiments of the presently disclosed formulations containing estradiol, progesterone or a combination thereof. In certain embodiments, a non-ionic surfactant is used. Exemplary non-ionic surfactants may include, for example and without limitation, one or more of oleic acid, linoleic acid, palmitic acid, and stearic acid esters or alcohols. In further embodiments, the non-ionic surfactant may comprise polyethylene sorbitol esters, including polysorbate 80, which is commercially available under the trademark TWEEN 80® (Sigma Aldrich, St. Louis, Mo.). Polysorbate 80 comprises approximately 60%-70% oleic acid with the remainder comprising primarily linoleic acids, palmitic acids, and stearic acids. Polysorbate 80 may be used in amounts ranging from about 5 to 50%, and in certain embodiments, about 30% of the formulation total mass.

In various other embodiments, the non-ionic surfactant is selected from one or more of glycerol and polyethylene glycol esters of fatty acids, for example, lauroyl macrogol-32 glycerides and/or lauroyl polyoxyl-32 glycerides, commercially available as Gelucire, including, for example, Gelucire 44/11 and Gelucire 44/14. These surfactants may be used at concentrations greater than about 0.01%, and typically in various amounts of about 0.01%-10.0%, 10.1%-20%, and 20.1%-30%. In certain examples, below, Gelucire 44/14 is used as a surfactant in amounts of 1 to 10 wt %. See, e.g., Tables 13-17, below. Other non-ionic surfactants include, e.g., Labrasol® PEG-8 Caprylic/Capric Glycerides (Gattefosse) and Labarafil® corn/apricot oil PEG-6 esters (Gattefosse).

In other embodiments, a lubricant is used. Any suitable lubricant may be used, such as for example lecithin. Lecithin may comprise a mixture of phospholipids.

In additional embodiments, an antioxidant is used. Any suitable anti-oxidant may be used such as, for example and without limitation butylated hydroxytoluene.

For example, in various embodiments, a pharmaceutical formulation comprises about 20% to about 80% carrier by weight, about 0.1% to about 5% lubricant by weight, and about 0.01% to about 0.1% antioxidant by weight.

The choice of excipient will, to a large extent, depend on factors such as the particular mode of administration, the effect of the excipient on solubility and stability, and the nature of the dosage form. Excipients used in various embodiments may include colorants, flavoring agents, preservatives and taste-masking agents. Colorants, for example, may comprise about 0.1% to about 2% by weight. Preservatives may comprise methyl and propyl paraben, for example, in a ratio of about 10:1, and at a proportion of about 0.005% and 0.05% by weight.

As is with all oils, solubilizers, excipients and any other additives used in the formulations described herein, each is to be non-toxic and pharmaceutically acceptable.

As referenced above, the formulations of the present disclosure are generally orally administered, typically via, for example, capsules such as soft capsules. The present formulations can also be used to form transdermal patches using standard technology known in the art. Solubilized formulations of the present invention can also be formulated for intraperitoneal administration using techniques well known in the art.

In accordance with various embodiments, formulations do not include peanut oil. The lack of peanut oil obviates the risk posed to those having peanut-based allergies.

Thus, an illustrative embodiment of a pharmaceutical composition of the invention comprises solubilized estradiol, progesterone at least 75% of the progesterone being solubilized (the balance being micronized as discussed elsewhere herein), and an oil, wherein the oil is medium chain fatty acid mono- and diesters of glycerol, with or without surfactant. In certain embodiments, a specification for progesterone is set at >80% solubilized, <20% micronized or >85% solubilized, <15% micronized. Specific examples of such illustrative embodiments, with Gelucire as surfactant, in which at least about 85% of the progesterone can be solubilized, include, e.g., the following four formulations:

| Formulation A- P: 50/EE: 0.25: | | |
|---|---|---|
| Ingredient(s) | Amount (% w/w) | Qty/Capsule (mg) |
| Progesterone, USP, micronized | 33.33 | 50.00 |
| Estradiol Hemihydrate | 0.17 | 0.26 |
| Capmul MCM, NF | 65.49 | 98.24 |
| Gelucire 44/14, NF | 1.00 | 1.50 |
| Total | 100.00 | 150.00 |

| Formulation B- P: 50/EE: 0.5: | | |
|---|---|---|
| Ingredient(s) | Amount (% w/w) | Qty/Capsule (mg) |
| Progesterone, USP, micronized | 33.33 | 50.00 |
| Estradiol Hemihydrate | 0.35 | 0.52 |
| Capmul MCM, NF | 65.32 | 97.98 |
| Gelucire 44/14, NF | 1.00 | 1.50 |
| Total | 100.00 | 150.00 |

| Formulation C - P: 100/EE: 0.5: | | |
|---|---|---|
| Ingredient(s) | Amount (% w/w) | Qty/Capsule (mg) |
| Progesterone, USP, micronized | 33.33 | 100.00 |
| Estradiol Hemihydrate | 0.17 | 0.52 |
| Capmul MCM, NF | 65.49 | 196.48 |
| Gelucire 44/14, NF | 1.00 | 3.00 |
| Total | 100.00 | 300.00 |

| Formulation D - P: 100/EE: 1: | | |
|---|---|---|
| Ingredient(s) | Amount (% w/w) | Qty/Capsule (mg) |
| Progesterone, USP, micronized | 33.33 | 100.00 |
| Estradiol Hemihydrate | 0.34 | 1.03 |
| Capmul MCM, NF | 65.32 | 195.97 |
| Gelucire 44/14, NF | 1.00 | 3.00 |
| Total | 100.00 | 300.00 |

| Formulation E- P: 200/EE: 2: | | |
|---|---|---|
| Ingredient(s) | Amount (% w/w) | Qty/Capsule (mg) |
| Progesterone, USP, micronized | 33.33 | 200.00 |
| Estradiol Hemihydrate | 0.34 | 2.06 |
| Capmul MCM, NF | 65.32 | 391.94 |
| Gelucire 44/14, NF | 1.00 | 6.00 |
| Total | 100.00 | 600.00 |

*Note: 1.00 mg Estradiol equivalent to 1.03 mg Estradiol Hemihydrate.

In general terms, the above formulations comprise 30 to 35 wt % progesterone, 0.1 to 0.4 wt % estradiol (or estradiol hemihydrate), 55 to 75 wt % of an oil that is predominantly medium chain fatty acid mono- and diglycerides, such as Capmul MCM, and 0.5 to 10 wt % non-ionic surfactant, such as Gelucire 44/14. The above formulations may be modified to comprise excipients, e.g., gelatin such as Gelatin 200 Bloom, glycerin, coloring agents such as Opatint red and white, and, optionally, Miglyol 812.

Estradiol solubilization helps ensure high content uniformity and enhanced stability. Fully solubilized progesterone formulations or partially solubilized progesterone formulations in which at least about 50% of the progesterone, e.g., 75%, 80%, 85%, 90%, or >95%, is solubilized appear to provide improved PK-related properties.

According to various embodiments described herein, a 28-day or monthly regimen of capsules can be packaged in a single kit (e.g., a blister pack) having administration days identified to improve compliance and reduce associated symptoms, among others. One or more of the capsules may contain no estradiol, for example, and/or no progesterone. Capsules that comprise no estrogen or progesterone API may be referred to as placebos. A blister pack can have a plurality of scores or perforations separating blister pack into 28 days. Each day may further comprise a single blister or a plurality of blisters. In various embodiments, each unit dose may contain micronized and/or partially solubilized, or fully solubilized progesterone and/or solubilized estradiol in amounts as set forth herein above, although other dose ranges may be contemplated. In addition, kits having other configurations are also contemplated herein. For example, without limitation, kits having such blister packs may contain any number of capsules.

Orally administered formulations of the present disclosure containing micronized and/or partially solubilized, or fully solubilized, progesterone are also used for the treatment of endometrial hyperplasia, secondary amenorrhea and other disease states treated with supplemental progesterone. Generally, progesterone-containing formulations described herein are used to treat the effects of the administration of supplemental estrogen whether administered alone or in combination with solubilized estradiol of the present disclosure or other estrogen-containing formulations. In various other embodiments, a capsule containing formulations of the present disclosure, for example a softgel capsule, may be applied in or around the vagina.

Formulations of the present disclosure containing solubilized estradiol are used to treat Estrogen-deficient States, including vasomotor symptoms, for example, in relation to treatment of hypoestrogenism related symptoms including, for example and without limitation, hot flashes and night sweats (vasomotor symptoms), sleep disturbances, mood changes, vulvo-vaginal atrophy, and osteoporosis and other non-menopausal disease states treated with supplemental estrogen.

Formulations of the present disclosure containing solubilized estradiol may be used to treat or prevent atrophic vaginitis or vulvo-vaginal atrophy. In various embodiments, a capsule, for example a softgel capsule, may be applied in or around the vagina.

Additional objects of the present disclosure includes: providing increased patient compliance secondary to ease of use; providing increased physician adoption secondary to ease of use/instruction with less worry of side effects from inappropriate usage; providing decreased side-effects from erroneous use (decreased irregular bleeding); providing better efficacy/control of symptoms secondary to appropriate use; reducing the metabolic and vascular side effects of the commonly used synthetic progestins when administered alone or in combination with an estrogen (norethindrone acetate, medroxyprogesterone acetate, etc.) including, for example, stroke, heart attacks, blood clots and breast cancer.

EXAMPLES

Example 1

Estradiol Solubility

In various experiments, suitable solvents were determined for providing sufficient solubility to make 2 mg of estradiol in a 100 mg fill mass, with a desired goal of achieving ~20 mg/g solubility for estradiol. Initial solubility experiments were done by mixing estradiol with various solvents, saturate the solution with the estradiol, equilibrate for at least 3 days and filter the un-dissolved particles and analyzing the clear supernatant for the amount of estradiol dissolved by HPLC.

Estradiol solubility experiments were performed. From this list at least one item (e.g. propylene glycol) is known to be unsuitable for encapsulation.

TABLE 1

| Ingredient | Solubility (mg/g) |
|---|---|
| PEG 400 | 105* |
| Propylene Glycol | 75* |
| Polysorbate 80 | 36* |
| Transcutol HP | 141 |
| Capmul PG8 | 31.2 |

*Literature reference -Salole, E. G. (1987) The Physicochemical Properties of Oestradiol, J Pharm and Biomed Analysis, 5, 635-640.

In further solubility studies, estradiol was soluble at at least 6 mg/gm Miglyol Transcutol in ratios of 81:19 to 95:5, in Miglyol;ethanol at 91:11, and in Miglyol:Capmul PG8 at 88:11, but not in Miglyol:Transcutol at 96:4, Miglyol:Labrasol at 70:30 to 80:20, or Miglyol:Capmul PG8 at 86:14.

Example 2

It was desired to achieve 50 mg of progesterone suspended in a medium that can also solubilize 2 mg estradiol in a total capsule fill mass of 200 mg. In order to achieve this formulation, the required solubility of estradiol needs to be ~10 mg/g. A total fill weight of 200 mg was considered suitable for a size 5 oval soft gelatin capsule.

Additional solubility studies were performed to find solvent mixtures that might possibly be more suitable for soft gelatin encapsulation. Solubility studies were conducted with Capmul PG8 and Capmul MCM by mixing estradiol with various solvent systems and as before by analyzing for the amount of estradiol dissolved by HPLC after filtration. Results of these experiments are presented in Table 2. It can be seen from these results that mixtures containing Miglyol:Capmul PG8 at 50%; and also Capmul MCM alone or in combination with 20% Polysorbate 80 can achieve sufficient solubility to meet the target of 10 mg/g. Capmul PG8 mixed with Miglyol at the 15 and 30% level did not provide sufficient solubility.

TABLE 2

| Ingredient | Solubility (mg/g) |
|---|---|
| Miglyol:Capmul PG8 (85:15) | 4.40 |
| Miglyol:Capmul PG8 (70:30) | 8.60 |

TABLE 2-continued

| Ingredient | Solubility (mg/g) |
|---|---|
| Transcutol:Miglyol 812:Capmul PG8 (5:65:28) | >12 |
| Transcutol:Miglyol 812:Capmul PG8 (5:47:47) | >12 |
| Miglyol:Capmul PG8 (50:50) | 14.0 |
| Capmul MCM | 19.8 |
| Polysorbate 80:Capmul MCM (20:80) | 15.0 |

Example 3

Additional studies were performed to assess the stability of estradiol (4-6 mg) in solvent mixtures, as reported in Table 3. Miglyol 812 with 4% Transcutol precipitated on Hot/Cold cycling after 96 hours, while estradiol solubilized in Miglyol:Capmul blends at 30 and 50% or in Capmul MCM alone, did not precipitate under the same conditions for a minimum of 14 days.

TABLE 3

| Formulation | Estradiol mg/g | Results Hot/Cold Cycling |
|---|---|---|
| Transcutol:Miglyol 812 (4:96) | 4 | Crystallizes after 96 hours |
| Miglyol 812:Capmul PG8 (70:30) | 6 | Clear, after 14 days |
| Miglyol 812:Capmul PG8 (50:50) | 6 | Clear, after 14 days |
| Transcutol:Miglyol 812:Capmul PG8 (5:80:15) | 6 | Clear, after 14 days |
| Capmul MCM | 6 | Clear after 14 days |

12 mg estradiol solubilized in Miglyol:Capmul PG8 50:50, Capmul MCM, and in mixtures of Transcutol: Miglyol: Capmul PG8 are stable and do not precipitate for at least 12 days.

TABLE 4

| Formulation | Estradiol mg/g | Results Hot/Cold Cycling |
|---|---|---|
| Miglyol 812:Capmul PG8 (50:50) | 12 | Clear, after 12 days |
| Transcutol:Miglyol 812:Capmul PG8 (5:65:28) | 12 | Clear, after 12 days |
| Transcutol:Miglyol 812:Capmul PG8 (5:47:47) | 12 | Clear, after 12 days |
| Capmul MCM | 12 | Clear after 12 days |

Example 4

In addition to determining physical stability of the estradiol solutions over time, it is necessary to determine if the fill material will be stable during the encapsulation process. One way to test these preparations is with the addition of water to the fill mass. As can be seen in Table 5, estradiol solutions at a concentration of 6 mg/g in Polyethylene Glycol 400 and Capmul MCM are able to absorb a minimum of 7% water without recrystallization, whereas the same concentration in Miglyol 812:Capmul PG8 (75:25) precipitates.

Estradiol solutions at a concentration of 12 mg/g in Polyethylene Glycol 400 and Capmul MCM are able to absorb a minimum of 7% water without recrystallization. All Capmul PG8 containing formulations turned hazy on the addition of water. However, it should be noted that estradiol recrystallization was not observed, and the addition of water to Capmul PG 8 alone (without any estradiol) also turns hazy on the addition of water.

TABLE 5

| Formulation | Estradiol mg/g | Results after addition of 7% water |
|---|---|---|
| Miglyol 812:Capmul PG8 (75:25) | 6 | Precipitated |
| Miglyol 812:Capmul PG8 (50:50) | 12 | Hazy |
| Transcutol:Miglyol 812:Capmul PG8 (5:65:28) | 12 | Hazy |
| Capmul MCM | 12 | Clear |
| Transcutol:Miglyol 812:Capmul PG8 (5:47:47) | 12 | Hazy |
| Polyethylene Glycol 400 | 12 | Clear |

Example 5

In an exemplary embodiment, a capsule is provided containing a fill material comprising:

TABLE 6

| Ingredient | Mg/Capsule |
|---|---|
| Estradiol Hemihydrate | 2.00 |
| Mono-, di- or triglyceride (Miglyol 812) | qs |
| Diethylene Glycol Monoethylether (Transcutol HP) | 65.00 |
| Liquid lecithin | 1.63 |
| Butylated Hydroxytoluene | 0.13 |
| Total Fill Weight | 325 |

Example 6

In an exemplary embodiment, a capsule is provided containing a fill material comprising:

TABLE 7

| Ingredient | Mg/Capsule |
|---|---|
| Estradiol Hemihydrate | 2.00 |
| Monoglycerides/diglycerides/triglycerides of caprylic/capric acid (Capmul MCM) | qs |
| Liquid lecithin | 1.63 |
| Polysorbate 80 | 97.5 |
| Total Fill Weight | 325 |

In an exemplary embodiment, a capsule is provided containing a fill material comprising:

TABLE 8

| Ingredient | Mg/Capsule | % w/w | Amount/Batch |
|---|---|---|---|
| Estradiol Hemihydrate | 2.03 | 0.62 | 20.2 g |
| Monoglycerides/diglycerides/triglycerides of caprylic/capric acid (Capmul MCM) | 322.97 | 99.38 | 3.23 kg |
| Total | | 100 | 3.25 kg |

The above formulation is prepared as follows: estradiol is added to Capmul MCM and mixed until dissolved.

Example 7

Progesterone Solubility

In various embodiments, both estradiol and progesterone may be dissolved in a solvent. In various embodiments, the solubility of both estradiol and progesterone will be such that a therapeutically effective dose may be obtained in a reasonably sized mass, generally considered to be between 1 mg and 1200 mg, preferably suitable for encapsulation in a size 3 to 22 oval or oblong capsule. For example, in various embodiments, 50 mg to 100 mg of progesterone may be dissolved in a volume of solvent; i.e., the solubility would be 50 mg to 100 mg per capsule. Miglyol was attempted, and while it can be considered a good carrier for progesterone, it alone did not provide a desirable level of solubilization of estradiol (e.g., solubility of 12 mg/g may be desirable in various embodiments). Thus, Miglyol may be used in embodiments comprising a suspension of progesterone, though Miglyol, standing alone, is not desirable for use in embodiments having fully solubilized progesterone and/or estradiol.

As can be seen in Table 9, the solubility of progesterone in Capmul MCM is ~73 mg/g. Therefore, by suspending 200 mg progesterone in 400 mg of solvent, part of the dose (~14%) is already dissolved and the remaining is still a suspension. In some aspects and embodiments, it is desired to minimize the partial solubility of progesterone in the formulation in order to minimize the possibility of recrystalization.

Based on 73 mg/g solubility, the capsule size required to make a capsule of 50 mg solubilized progesterone would be 685 mg. Therefore, it was shown that it would be feasible to make a 50 mg progesterone and 2 mg estradiol solubilized formulation. Myglyol had the lowest solubility, but that solvent is unable to dissolve the estradiol, therefore under further experiments, it was decided to proceed with the second lowest or Capmul MCM. It has also been found that 2 mg of estradiol may also be dissolved in 685 mg of Capmul MCM.

TABLE 9

| Ingredient | Progesterone Solubility (mg/g) |
| --- | --- |
| Capmul MCM | 73.4 |
| Capmul PG8 | 95 |
| Miglyol 812 | 27.8 |
| Capmul MCM:Gelucire 44/14 (9:1) | 86.4 |
| Capmul MCM:Gelucire 44/14 (7:3) | 70.5 |
| Capmul MCM:Gelucire 44/14 (6:3) | 57.4 |

In addition, it has been found that the solubility of progesterone in a solvent of Capmul MCM in combination with Gelucire 44/14 in a 9:1 ratio increases the solubility to approximately 86 mg/g. Therefore, in various embodiments, progesterone and/or estradiol may be dissolved in a Capmul MCM and Gelucire 44/14 system, wherein the ratio of Capmul MCM to Gelucire 44/14 is 9:1.

TABLE 10

| Ingredient | Progesterone Solubility (mg/g) |
| --- | --- |
| Capmul MCM:Gelucire 44/14 (9:1) | 86.4 |
| Capmul MCM:Gelucire 44/14 (7:3) | 70.5 |
| Capmul MCM:Gelucire 44/14 (6:4) | 57.4 |

Example 7-1

In an exemplary embodiment, a capsule is provided containing a fill material having fully solubilized progesterone and estradiol comprising:

TABLE 11

| Ingredient | Mass (mg) | % w/w | Qty/Capsule (mg) |
| --- | --- | --- | --- |
| Progesterone, USP, micronized | 50.00 | 7.14 | 50.00 |
| Estradiol Hemihydrate, USP | 2.03 | 0.29 | 2.03 |
| Capmul MCM, NF | | 82.57 | 577.97 |
| Gelucire 44/14, NF | | 10.0 | 70.00 |
| TOTAL | | 100.00 | 700.00 |

A capsule such as that shown in TABLE 11 may be manufactured in any suitable manner. For the purposes of this Example, mixing may be facilitated by an impellor, agitator, or other suitable means. Also for the purposes of this Example, heating and/or mixing may be performed under an inert or relatively inert gas atmosphere, such as nitrogen gas N2. Mixing and/or heating for the purposes of this Example may be performed in any suitable vessel, such as a stainless steel vessel.

For example, Campul MCM may be heated to between 30° C. to 50° C., more preferably from 35° C. to 45° C., and more preferably to 40° C.+/−2° C. Gelucire 44/14 may be added to the Campul MCM and mixed until dissolved. The addition may occur all at once or may occur gradually over a period of time. Heat may continue to be applied during the mixing of the Gelucire 44/14 and the Campul MCM.

Heat may be removed from the Gelucire 44/14 and Campul MCM mixture. Estradiol Hemihydrate may be added to the mixture. The addition may occur all at once or may occur gradually over a period of time. Micronized progesterone may then be added to the Gelucire 44/14, Campul MCM and Estradiol Hemihydrate mixture until dissolved. The addition may occur all at once or may occur gradually over a period of time.

Example 8

In an exemplary embodiment, a capsule is provided containing a fill material having suspended progesterone comprising:

TABLE 12

| Ingredient | mg/Capsule | % | Function |
| --- | --- | --- | --- |
| Micronized Progesterone | 200.00 | 30.77 | Active |
| Medium Chain Triglyceride (MIGLYOL 812 or equivalent) | qs | qs | Carrier |
| Lecithin Liquid | 1.63 | 0.25 | Lubricant/Emulsifier |
| Butylated Hydroxytoluene (also referred to as "BHT") | 0.13 | 0.02 | Antioxidant |

The above formulation is prepared as follows: MIGLYOL is heated to about 45° C. GELUCIRE 44/14 is added and mixed until dissolved. BHT is added and mixed until dissolved. Progesterone is suspended and passed through a colloid mill. The resultant fill mass can be used for encapsulation.

In an exemplary embodiment, a capsule is provided containing a fill material having partially solubilized progesterone comprising:

TABLE 13

| Ingredient | Qty/Capsule (mg) | % w/w | Qty/Capsule (mg) | Amount/Batch (kg) |
|---|---|---|---|---|
| Micronized Progesterone, USP | 200.00 | 33.33 | Active | 2.0 |
| Monoglycerides/diglycerides/triglycerides of caprylic/capric acid (Capmul MCM) | 394.0 | 65.67 | Carrier | 3.94 |
| Lauroyl polyoxyl-32-glycerides (Gelucire 44/14 or equivalent) | 6.0 | 1 | Lubricant/Emulsifier | 0.06 |
| Total | 600.00 mg | 100 | | 6.0 kg |

For suspensions of progesterone and partially solubilized progesterone, GELUCIRE 44/14 may be added at 1% to 2% w/w to increase viscosity. The above formulation is prepared as follows: Capmul MCM is heated to about 65° C. GELUCIRE 44/14 is added and mixed until dissolved. Heat is removed. Progesterone is added and the mixture is passed through a colloid mill. The resultant fill mass can be used for encapsulation.

Example 9

In an exemplary embodiment, a capsule is provided containing a fill material having suspended progesterone comprising:

TABLE 14

| Ingredient | % | mg/Capsule | Function |
|---|---|---|---|
| Micronized Progesterone | 30.77 | 200.00 | Active |
| Medium Chain Triglyceride (MIGLYOL 812 or equivalent) | 65.93 | 428.55 | Carrier |
| Lauroyl polyoxyl-32-glycerides (Gelucire 44/14 or equivalent) | 3.00 | 19.50 | Suspending Agent |
| Butylated Hydroxytoluene | 0.03 | 1.95 | Antioxidant |
| Total | 100 | 650 | |

In various embodiments, amounts of MIGLYOL may be present in a range from about 35-95% by weight; GELUCIRE 44/14 from about 0.5-30% by weight; and BHT from about 0.01-0.1% by weight.

Example 10

For the purposes of this Example, a particle size analysis is conducted by using the Beckman Device. A sample API comprising micronized progesterone in accordance with various embodiments is provided for analysis.

Figure 4:
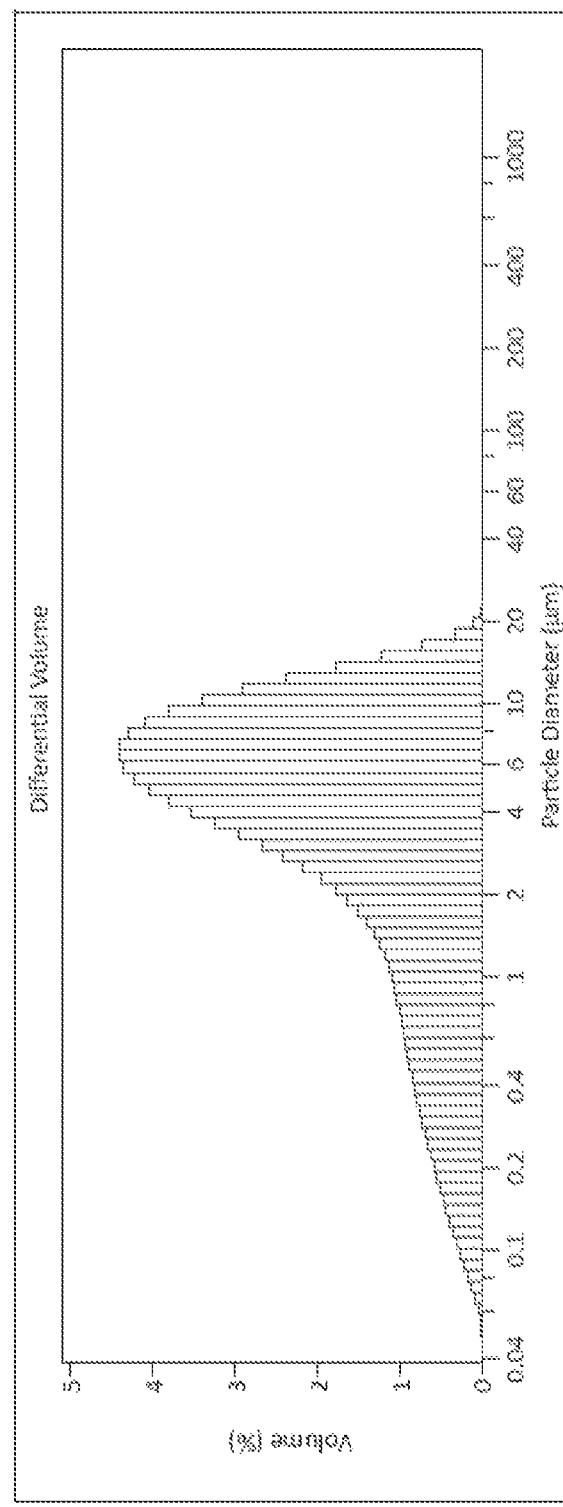
FIG. 4 illustrates a graph of the particle distribution obtained in Example 10.

Approximately 0.01 g of a sample API in accordance with various embodiments was combined with Coulter 1B and 10 mL of deionized water. Sonication was performed for 15 seconds. The Beckman Device, equipped with a ULM, performed analysis for 90 seconds. The Beckman Device was configured to use the Fraunhofer optical model. The Beckman Device yielded that the sample has an X50 of 4.279 µm, an X75 of 7.442 µm, and an X25 of 1.590 µm. The Beckman Device also yielded that the mean particle size is 4.975 µm, the median particle size is 4.279 µm, the mode particle size is 6.453 µm, and the standard deviation is 3.956 µm. A graph of the particle distribution obtained is shown in FIG. 4.

Example 11

A formulation sample having approximately 200 mg of micronized progesterone and 2 mg of estradiol was dispersed with oil. The Beckman Device, equipped with a MLM, performed analysis for 60 seconds. The Beckman Device was configured to use the Fraunhofer optical model. The Beckman Device yielded that the sample has an X50 of 11.0 µm, an X75 of 17.3 µm, and an X25 of 5.3 µm. The Beckman Device also yielded that the mean particle size is 11.8 µm, the median particle size is 11.04 µm, the mode particle size is 13.6 µm, and the standard deviation is 7.8 µm.

Example 12

In order to increase the solubility of progesterone in the final solution, Gelucire 44/14 was added at about 10% w/w.

TABLE 15

Quantitative Formula: Batch Size 10,000 capsules

| Item No. | Ingredient(s) | Label Claim (mg) | % w/w | Qty/Capsule (mg) | Amount/Batch (kg) |
|---|---|---|---|---|---|
| 1. | Progesterone, USP, micronized | 50.00 | 7.14 | 50.00 | 0.50 |
| 2. | Estradiol Hemihydrate, USP | 2.03 | 0.29 | 2.03 | 0.02 |
| 3. | Capmul MCM, NF | | 82.57 | 577.97 | 5.78 |
| 4. | Gelucire 44/14, NF | | 10.0 | 70.00 | 0.70 |
| | Total: | | 100.00 | 700.00 | 7.00 |

An example of the final formulation is provided in Table 15. The manufacturing process is as follows. Capmul MCM is heated to 40° C. Gelucire 44/14 is heated to 65 C and added and mixed until dissolved. Heat is removed. Estradiol is added and mixed until dissolved. Micronized progesterone is then added and mixed until dissolved.

Example 13

In an exemplary embodiment, a capsule is provided containing a fill material having fully solubilized estradiol and partially solubilized progesterone comprising:

TABLE 16

| Item No. | Ingredient(s) | Label Claim (mg) | % w/w | Qty/Capsule (mg) | Amount/Batch (g) |
|---|---|---|---|---|---|
| 1. | Progesterone, USP, micronized | 50.00 | 25.000 | 50.00 | 500.00 |
| 2. | Estradiol Hemihydrate | 0.25 | 0.129 | 0.26 | 2.58 |
| 3. | Capmul MCM, NF | | 73.371 | 146.74 | 1467.42 |
| 4. | Gelucire 44/14, NF | | 1.500 | 3.00 | 30.00 |
| | Total: | | 100.000 | 200.00 mg | 2000.00 |

The manufacturing process is as follows. Capmul MCM is heated to 65° C. Gelucire 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation.

Example 14

In an exemplary embodiment, a capsule is provided containing a fill material having fully solubilized estradiol and partially solubilized progesterone comprising:

TABLE 17

| Item No. | Ingredient(s) | Label Claim (mg) | % w/w | Qty/ Capsule (mg) | Amount/ Batch (g) |
|---|---|---|---|---|---|
| 1. | Progesterone, USP, micronized | 200.00 | 33.33 | 200.0 | 2000.0 |
| 2. | Estradiol Hemihydrate | 2.00 | 0.35 | 2.07 | 20.7 |
| 3. | Capmul MCM, NF | | 65.32 | 391.93 | 3919.3 |
| 4. | Gelucire 44/14, NF | | 1.00 | 6.0 | 60.0 |
| | Total: | | 100.00 | 600.0 mg | 6000.0 |

The manufacturing process is as follows. Capmul MCM is heated to 65° C. Gelucire 44/14 is added and mixed until dissolved. Heat is removed. Estradiol is added and mixed until dissolved. Micronized progesterone is then added and dispersed. The mixture is then passed through a colloid mill. The resultant fill mass can be used for encapsulation. Alternatively, Gelucire 44/14 is heated to 65 C and Capmul MCM is heated to 40 C+/−5 C to achieve mixing of the oil and the surfactant before heat is removed; estradiol is added while the mixture is cooling; progesterone is added when the mixture has dropped below about 40 C; the mixture is then passed through a colloid mill, e.g., three times.

Example 15

Study 352—Progesterone and Estradiol Combination Study Under Fed Conditions

This following study protocol was used to establish bio-availability and bio-equivalence parameters for a combination product of the present disclosure comprising progesterone (200 mg) and estradiol (2.0 mg) as prepared via the process described in Example 14 and compared to 200 mg of PROMETRIUM® (Catalent Pharmaceuticals, St. Petersburg, Fla. (and 2.0 mg of ESTRACE® (Bristol-Myers Squibb Co. Princeton, N.J.), administered to twenty-four (24) normal healthy, adult human post-menopausal female subjects under fed conditions.

The pharmaceutical formulation of the invention used in these PK studies had substantially the following formula:

| Ingredient(s) | Amount (% w/w) | Qty/Capsule (mg) |
|---|---|---|
| Progesterone, USP, micronized | 7.14 | 50.00 |
| Estradiol Hemihydrate, USP Micronized | 0.30 | 2.07 |
| Capmul MCM, NF, USP | 83.27 | 582.93 |
| Gelucire 44/14, NF | 9.29 | 650 |
| Total | 100.00 | 700 |

The Study Design: An open-label, balanced, randomized, two-treatment, two-period, two-sequence, single-dose, two-way crossover study.

The subjects were housed in the clinical facility from at least 11.00 hours pre-dose to at least 48.00 hours post-dose in each period, with a washout period of at least 14 days between the successive dosing days.

Subjects were fasted for at least about 10.00 hours before being served a high-fat, high-calorie breakfast, followed by dosing, then followed by a 04.00 hour, post-dose additional period of fasting.

Standard meals were provided at about 04.00, 09.00, 13.00, 25.00, 29.00, 34.00 and 38.00 hours post-dose, respectively.

Water was restricted at least about 01 hour prior to dosing until about 01 hour post-dose (except for water given during dosing). At other times, drinking water was provided ad libitum.

Subjects were instructed to abstain from consuming caffeine and/or xanthine containing products (i.e. coffee, tea, chocolate, and caffeine-containing sodas, colas, etc.) for at least about 24.00 hours prior to dosing and throughout the study, grapefruit and\or its juice and poppy containing foods for at least about 48.00 hours prior to dosing and throughout the study.

Subjects remained seated upright for about the first 04.00 hours post-dose and only necessary movements were allowed during this period. Thereafter subjects were allowed to ambulate freely during the remaining part of the study. Subjects were not allowed to lie down (except as directed by the physician secondary to adverse events) during restriction period.

Subjects were instructed not to take any prescription medications within 14 days prior to study check in and throughout the study. Subjects were instructed not to take any over the counter medicinal products, herbal medications, etc. within 7 days prior to study check-in and throughout the study.

After overnight fasting of at least about 10.00 hours, a high-fat high-calorie breakfast was served about 30 minutes prior to administration of investigational product(s). All subjects were required to consume their entire breakfast within about 30 minutes of it being served, a single dose of either test product (T) of Progesterone 200 mg & Estradiol 2 mg tablets or the reference product (R) PROMETRIUM® (Progesterone) soft gel Capsule 200 mg and ESTRACE® (Estradiol) Tablets 2 mg (according to the randomization schedule) were administered with about 240 mL of water under fed condition, at ambient temperature in each period in sitting posture. A thorough mouth check was done to assess the compliance to dosing.

All dosed study subjects were assessed for laboratory tests at the end of the study or as applicable.

In each period, twenty-three (23) blood samples were collected. The pre-dose (10 mL) blood samples at −01.00, −00.50, 00.00 hours and the post-dose blood samples (08 mL each) were collected at 00.25, 00.50, 00.67, 00.83, 01.00, 01.33, 01.67, 02.00, 02.50, 03.00, 04.00, 05.00, 06.00, 07.00, 08.00, 10.00, 12.00, 18.00, 24.00 and 48.00 hours in labeled K2EDTA—vacutainers via an indwelling cannula placed in one of the forearm veins of the subjects. Each intravenous indwelling cannula was kept in situ as long as possible by injecting about 0.5 mL of 10 IU/mL of heparin in normal saline solution to maintain the cannula for collection of the post-dose samples. In such cases blood samples were collected after discarding the first 0.5 mL of heparin containing blood. Each cannula was removed after the 24.00 hour sample was drawn or earlier or if blocked.

At the end of the study, the samples were transferred to the bio-analytical facility in a box containing sufficient dry ice to maintain the integrity of the samples. These samples were stored at a temperature of −70° C.±20° C. in the bio-analytical facility until analysis.

Progesterone (Corrected and Uncorrected) and Estradiol (unconjugated) and estrone (total) in plasma samples is assayed using a validated LC-MS/MS method.

The pharmacokinetic parameters Cmax, AUC0-t & AUC0-∞ were calculated on data obtained from 24 subjects for the test product and reference product. In general, bioavailability of progesterone and estradiol were similar but bioequivalence was not established.

Corrected pharmacokinetic profile summaries are presented in Table 18, below, for progesterone.

TABLE 18

Summary of Primary Pharmacokinetic Profile of Test Product (T) versus Reference Product (R) for Progesterone (Corrected)

| Pharmacokinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 47.0 | 43.0 | 81.0 ± 82.8 | 117.7 ± 173.7 |
| $AUC_{0-t}$ | 107.6 | 97.8 | 163.9 ± 136.5 | 191.1 ± 241.7 |
| $AUC_{0-\infty}$ | 110.7 | 110.0 | 173.5 ± 143.0 | 207.1 ± 250.3 |

*Estimate of Least Square Mean used to calculate Geometric Mean

Study 351—Progesterone and Estradiol Combination Study Under Fasting Conditions.

Fasted studies using the above protocol and test and reference products were also conducted. However, rather than the high-fat meal prior to administration of the test and reference drug, each subject fasted for a period of at least twelve (12) hours prior to dose administration.

The pharmacokinetic parameters Cmax, AUC0-t & AUC0-∞ were calculated on data obtained from 23 subjects under fasting conditions for the test product and reference product. In general, bioavailability of progesterone and estradiol were similar but bioequivalence was not established.

Corrected pharmacokinetic profile summaries are presented in Table 19, below for progesterone.

TABLE 19

Summary of Primary Pharmacokinetic Profile of Test Product (T) versus Reference Product (R) for Progesterone (Corrected)

| Pharmacokinetic Parameter | Geometric Mean* | | Arithmetic Mean ± Standard Deviation | |
|---|---|---|---|---|
| | Test Product (T) | Reference Product (R) | Test Product (T) | Reference Product (R) |
| $C_{max}$ | 2.3 | 3.0 | 2.9 ± 2.3 | 3.9 ± 3.4 |
| $AUC_{0-t}$ | 8.4 | 10.9 | 11.2 ± 8.7 | 14.5 ± 11.0 |
| $AUC_{0-\infty}$ | 12.9 | 17.2 | 15.1 ± 9.0 | 19.6 ± 10.2 |

*Estimate of Least Square Mean used to calculate Geometric Mean

The data indicate good (i.e., low) inter-patient and intra-patient variability relative to Prometrium.

Example 16

Figure 2:
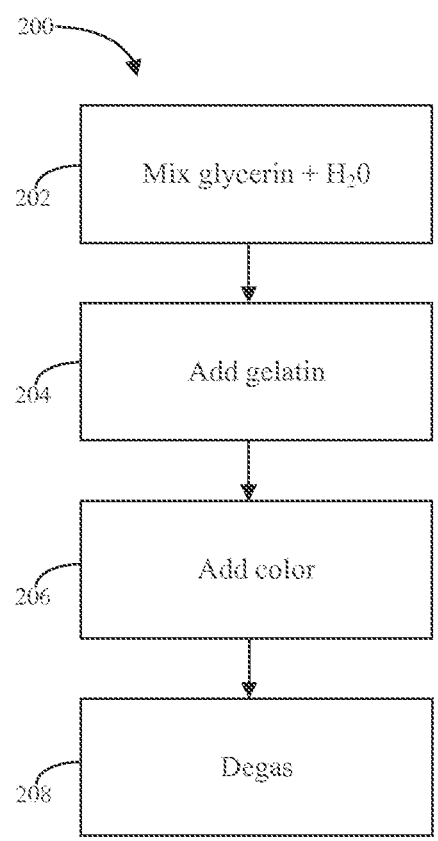
FIG. 2 illustrates an exemplary manufacturing process of a softgel material in accordance with various embodiments.
Figure 3:
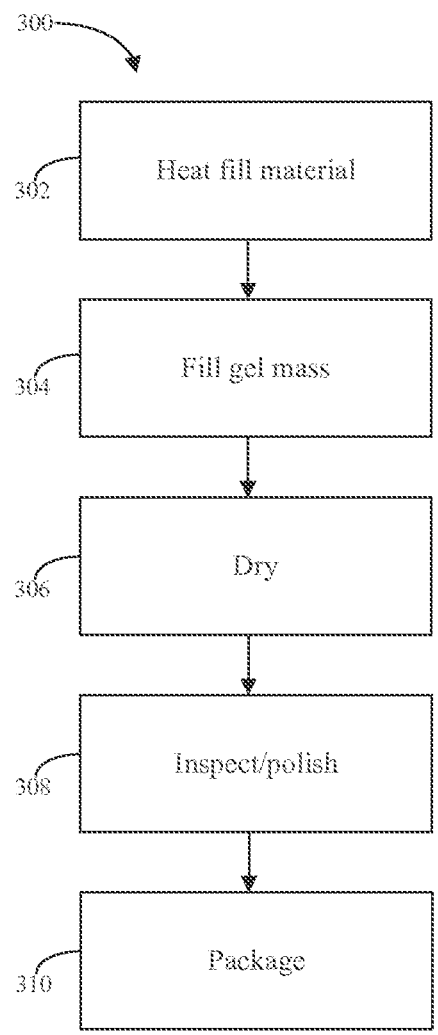
FIG. 3 illustrates an exemplary manufacturing process in accordance with various embodiments.

Method of manufacture in accordance with various embodiments are shown in FIGS. 1-3. With reference to FIG. 1, method of fill material 100 is shown. Step 102 comprises heating an oily vehicle carrier to 40° C.±5° C. Heating may be accomplished through any suitable means. The heating may be performed in any suitable vessel, such as a stainless steel vessel. The oily vehicle may be any oily vehicle described herein, for example, Capmul MCM.

Step 104 comprises mixing Gelucire 44/14 with the oily vehicle. Mixing may be facilitated by an impellor, agitator, or other suitable means. Step 102 may be performed under an inert or relatively inert gas atmosphere, such as nitrogen gas N2. Mixing may be performed in any suitable vessel, such as a stainless steel vessel.

Step 106 comprises mixing estradiol into the mixture of the oily vehicle and Gelucire 44/14. Mixing may occur in a steel tank or vat. Mixing may be facilitated by an impellor, agitator, or other suitable means. Step 106 may be performed under an inert or relatively inert gas atmosphere, such as nitrogen gas N2.

Step 108 comprises cooling to room temperature. Cooling may be allowed to occur without intervention or cooling may be aided by application of a cooling system.

Step 110 comprises mixing micronized progesterone into the mixture of oily vehicle, estradiol and Gelucire 44/14. Mixing may occur in a steel tank or vat. Mixing may be facilitated by an impellor, agitator, or other suitable means. Step 110 may be performed under an inert or relatively inert gas atmosphere, such as nitrogen gas N2. Step 112 comprises degassing. The resulting mixture from step 112 may comprise a fill material suitable for production into a softgel capsule.

With reference to FIG. 2, softgel capsule, i.e. gel mass, production 200 is shown. Step 202 comprises mixing glycerin with water. The water used in step 202 may be purified by any suitable means, such as reverse osmosis, ozonation, filtration (e.g., through a carbon column) or the like. Mixing may be facilitated by an impellor, agitator, or other suitable means. Step 202 may be performed under an inert or relatively inert gas atmosphere, such as nitrogen gas N2. Heating may be performed until the temperature reaches 80° C.±5° C.

Step 204 comprises the addition of gelatin to the glycerin water mixture. Mixing may be facilitated by an impellor, agitator, or other suitable means. Step 204 may be performed under an inert or relatively inert gas atmosphere, such as nitrogen gas N2. A vacuum may be drawn in step 204 to de-aerate.

Step 206 comprises addition of a coloring agent such as a dye. A coloring agent may comprise products sold under the trademark OPATINT or other suitable agent. Step 206 may be performed under an inert or relatively inert gas atmosphere, such as nitrogen gas N2. Step 208 comprises degassing. The resulting mixture from step 208 may comprise a gel capsule material suitable for use as a gel capsule in production of a softgel capsule.

With reference to FIG. 3, softgel capsule assembly process 300 is shown. Step 302 comprises heating the fill material. The fill material may be heated to any suitable temperature. In various embodiments, the fill material is heated to 30° C.+/−3° C. Fill material may be heated in a fill hopper. A fill hopper may comprise a device configured to hold a volume of the fill material and/or to dispense the fill material in controlled volumes.

Step 304 comprises filling a gel mass. A gel mass may be taken from the gel capsule material produced in step 208 of FIG. 2. Filling may be performed by injecting, placing, or otherwise disposing the fill material within a volume defined by the gel capsule material. The filling may occur in an encapsulator. The spreader boxes may be a temperature of 55° C.+/−10° C. The wedge temperature may be 38° C.+/−3° C. The drum cooling temperature may be 4° C.+/−2° C. The encapsulator may be lubricated using MIGLYOL 812 or other suitable lubricant. Step 304 thus produces one or more softgel capsules. Filling may comprise producing a ribbon of thickness 0.85 mm±0.05 mm using spreader box knobs. The fill material may be injected into the gel to produce a fill weight having target weight ±5% (i.e., 650±33 mg and 325±16.3 mg).

Step 306 comprises drying the softgel capsules. Drying may be performed in a tumble dryer, tray dryer, or combinations thereof. For example, drying may be performed in a tumble drying basket for between about 10 minutes and about 120 minutes. Drying may continue in a drying room for about 24 hours to about 72 hours. Step 308 may comprise inspection and/or polishing. Polishing may be performed with isopropyl alcohol. Step 310 may comprise packaging. Packaging may be accomplished through any suitable means. Packaging may comprise packing softgel capsules into a blister pack, bottle, box, pouch, or other acceptable packaging.

Example 17

Solubility of Estradiol in Soy Bean Oil, Peanut Oil, and Safflower Oil

Data was obtained visually by making the mixtures described below, sonicating the mixtures, and then seeing if a clear solution resulted. If a clear solution was achieved, it was an indication of solubility at the level studied.

Procedures and Results:
Step 1.
0.3% of Estradiol suspension in each oil was prepared by adding 30 mg Estradiol to solvent and QS to 10 g. Samples were mixed on vortex for 2 hours, heated @ 50° C. for 30 minutes and then mixed for 1 hour more. All samples were still in suspension form.

Step 2.
Each sample was diluted to 0.24% (by adding 2.5 g more oil) and mixed for 2 hours and heated @ 50° C. for 30 min and mixed again for one hour. All the samples were still cloudy. Samples were kept at room temperature overnight to see if they precipitate or if un-dissolved API settles out. After 20 hours at room temperature, it was observed that all samples still had un-dissolved API.

Step 3.
Each sample was diluted to 0.2% (by adding 2.5 g more oil) and mixed 2 for hours and heated @ 50° C. for 30 min and mixed again for one hour. All the samples were still slightly cloudy, indicating that the estradiol was not completely dissolved.

TABLE 20

| Ingredient | Estradiol Solubility (mg/g) | Estradiol Solubility (% w/w) |
|---|---|---|
| Peanut Oil | <2 | <0.2 |
| Safflower Oil | <2 | <0.2 |
| Soy Bean Oil | <2 | <0.2 |

The solubility of estradiol in all three oils was less than 2 mg/g (0.2% w/w). This level of solubility is significantly below the solubility that the present inventors have discovered can be achieved in other oils, e.g., medium chain fatty acid esters, such as the mono/diglycerides, propylene glycol esters, and polyethylene glycol esters discussed above.

In sum, if no heat is used to dissolve estradiol in safflower oil, it will not go into solution. Given that the estradiol did not dissolve at 50 C, oils such as safflower oil will not be useful in the methods of the invention using medium chain fatty acid esters as described hereinabove.

Example 18

Dissolution

Dissolution studies were performed using a formulation of this invention comparing the dissolution of progesterone to the dissolution of Prometrium and comparing the dissolution of estradiol to the dissolution of Estrace. In one study, a formulation of the invention in capsules comprising 200 mg of progesterone and 2 mg estradiol was used. In a second study, a formulation of the invention in capsules comprising 50 mg of progesterone and 2 mg estradiol was used. The two formulations comprised:

The dissolution study was performed using a USP dissolution apparatus (reciprocating cylinder) ("USP Apparatus 3"). The apparatus was set to 30 dips per minute. 250 mL of a solution of 0.1N HCl with 3% sodium lauryl sulfate was used at 37 C.

Figure 5:
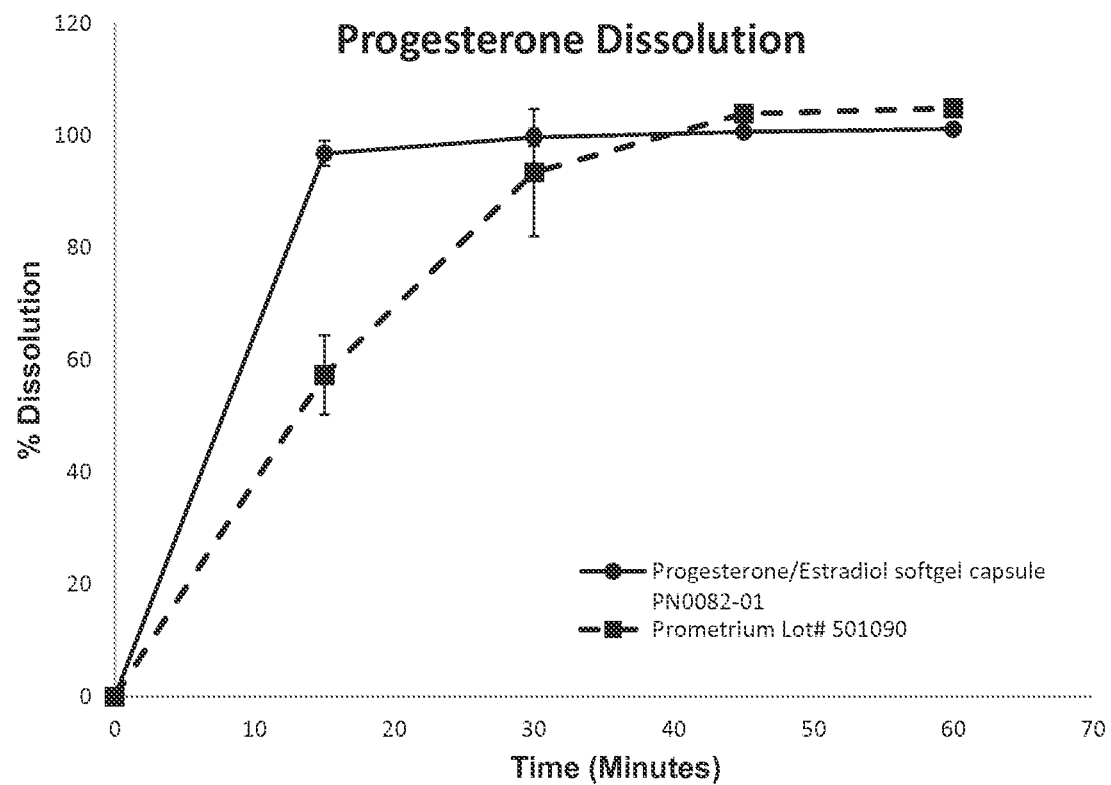
FIG. 5 illustrates a dissolution study of a formulation in accordance with various embodiments of the invention.

In both studies, progesterone was dissolved faster, and with smaller standard deviations, from the capsules of the invention than from Prometrium. Dissolution of estradiol was comparable but marginally slower from the capsules of the invention than from Estrace. For illustrative purposes, a graph showing progestrone dissolution from the 200 mg progesterone capsule of the invention and from Prometrium is attached as FIG. 5.

Both capsules of the invention were stable on storage in white HDPE bottles. Positive stability data were obtained with the 200 mg progesterone formulation over 6 months (>6 months data unavailable) and with the 50 mg progesterone formulation over 3 months (>3 months data unavailable).

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. This disclosure is intended as illustrative only and as such is not intended to be exhaustive. It will be evident to those skilled in the art that various modifications may be made, especially in matters of structure, materials, elements, components, shape, size and arrangement of parts including combinations within the principles of the disclosure, to the full extent indicated by the broad general meaning of the terms in which the appended claims are expressed. To the extent that these various modifications do not depart from the spirit and scope of the appended claims, they are intended to be encompassed therein.

What is claimed is:

1. A method of treating an estrogen-deficient state in a female subject in need of treatment, the method comprising administering to the subject a capsule containing an effective amount of a pharmaceutical formulation comprising:
   0.17 to 0.35 wt % solubilized estradiol,
   30 to 35 wt % progesterone, comprising suspended micronized progesterone and solubilized progesterone,
   55 to 75 wt % of an oil, wherein the oil is predominantly medium chain fatty acid mono- and diglycerides comprising esters of C6 to C12 fatty acids, and
   0.5 to 10 wt % nonionic surfactant;
   wherein the solubilized estradiol, the suspended micronized progesterone, and the solubilized progesterone are present in the oil.

2. The method of claim 1, wherein the oil is predominantly medium chain fatty acid mono- and diglycerides comprising esters of C6 to C10 fatty acids.

3. The method of claim 1, wherein the oil is predominantly medium chain fatty acid mono- and diglycerides comprising esters of C8 to C12 fatty acids.

4. The method of claim 1, wherein the oil is predominantly medium chain fatty acid mono- and diglycerides comprising esters of C8 to C10 fatty acids.

5. The method of claim 1, wherein at least 90% of the total estradiol is solubilized.

6. The method of claim 1, wherein the non-ionic surfactant is lauroyl polyoxyl-32-glycerides.

7. The method of claim 1 wherein the capsule is a gelatin capsule.

8. The method of claim 1, wherein the progesterone is released more rapidly from the pharmaceutical composition than progesterone in peanut oil.

9. The method of claim 1, wherein the estrogen-deficient state is selected from the group consisting of a vasomotor symptom of menopause, sleep disturbances, mood changes, vulvovaginal atrophy, and osteoporosis.

10. The method of claim 1, wherein the estrogen-deficient state is a vasomotor symptom of menopause.

11. The method of claim 1, wherein the vasomotor symptom of menopause is selected from the group consisting of hot flashes and night sweats.

12. The method of claim 1, wherein the female subject is a post-menopausal woman.

13. A method of treating a vasomotor symptom of menopause in a female subject in need of treatment, the method comprising administering to the subject a capsule containing an effective amount of a pharmaceutical formulation comprising:

0.17 to 0.35 wt % solubilized estradiol, 30 to 35 wt % progesterone, comprising suspended micronized progesterone and solubilized progesterone, 55 to 75 wt % of an oil, wherein the oil is predominantly medium chain fatty acid mono- and diglycerides comprising predominantly esters of C6 to C12 fatty acids, and 0.5 to 10 wt % nonionic surfactant;

wherein the solubilized estradiol, the suspended micronized progesterone, and the solubilized progesterone are present in the oil.

14. The method of claim 13, wherein the vasomotor symptom of menopause is selected from the group consisting of hot flashes and night sweats.

15. The method of claim 13, wherein the mammal is a post-menopausal woman.

16. A method of treating vulvovaginal atrophy in a female subject in need of treatment, the method comprising administering to the subject a capsule containing an effective amount of a pharmaceutical formulation comprising:

0.17 to 0.35 wt % solubilized estradiol, 30 to 35 wt % progesterone, comprising suspended micronized progesterone and solubilized progesterone, 55 to 75 wt % of an oil, wherein the oil is predominantly medium chain fatty acid mono- and diglycerides comprising predominantly esters of C6 to C12 fatty acids, and 0.5 to 10 wt % nonionic surfactant;

wherein the solubilized estradiol, the suspended micronized progesterone, and the solubilized progesterone are present in the oil.

* * * * *